United States Patent
Reimann et al.

(10) Patent No.: US 9,416,366 B2
(45) Date of Patent: Aug. 16, 2016

(54) MAIZE ETHYLENE SIGNALING GENES AND MODULATION OF SAME FOR IMPROVED STRESS TOLERANCE IN PLANTS

(71) Applicant: PIONEER HI BRED INTERNATIONAL INC, Johnston, IA (US)

(72) Inventors: Kellie Reimann, Ankeny, IA (US); Shoba Sivasankar, Adel, IA (US)

(73) Assignee: PIONEER HI-BRED INTERNATIONAL INC, Johnston, IA (US)

(*) Notice: Subject to any disclaimer, the term of this patent is extended or adjusted under 35 U.S.C. 154(b) by 328 days.

(21) Appl. No.: 13/956,517

(22) Filed: Aug. 1, 2013

(65) Prior Publication Data

US 2013/0318654 A1 Nov. 28, 2013

Related U.S. Application Data

(63) Continuation of application No. 13/354,882, filed on Jan. 20, 2012, now Pat. No. 8,614,368, which is a continuation of application No. 12/274,527, filed on Nov. 20, 2008, now Pat. No. 8,129,586.

(60) Provisional application No. 60/989,368, filed on Nov. 20, 2007.

(51) Int. Cl.
*C12N 15/82* (2006.01)
*C07K 14/415* (2006.01)

(52) U.S. Cl.
CPC .......... *C12N 15/8271* (2013.01); *C07K 14/415* (2013.01); *C12N 15/8249* (2013.01); *C12N 15/8273* (2013.01)

(58) Field of Classification Search
None
See application file for complete search history.

(56) References Cited

U.S. PATENT DOCUMENTS

| | | |
|---|---|---|
| 2006/0141495 A1 | 6/2006 | Wu |
| 2006/0200875 A1 | 9/2006 | Guo et al. |
| 2007/0192889 A1 | 8/2007 | La Rosa et al. |

FOREIGN PATENT DOCUMENTS

| | | |
|---|---|---|
| WO | 0105953 A2 | 1/2001 |
| WO | 2008070179 A2 | 6/2008 |

OTHER PUBLICATIONS

Fujimoto, S.Y., et al.; "Arabidopsis Ethylene-Responsive Element Binding Factors Act as Transcriptional Activators or Repressors of GCC Box-Mediated Gene Expression"; The Plant Cell (Mar. 2000) 12:393-404; American Society of Plant Physiologists; Rockville, MD US.
Nishiuchi, T., et al.; "Rapid and Transient Activation of Transcription of the ERF3 Gene by Wounding in Tobacco Leaves"; The Journal of Biological Chemistry (Dec. 31, 2004) 279(53):55355-55361; The American Society of Biochemistry and Molecular Biology, Inc.; US.
Ohme-Takagi, M, et al.; "Regulation of Ethylene-Induced Transcription of Defense Genes"; Plant Cell Physiology (2000) 41(11):1187-1192; Oxford University Press; Oxford, UK.
Koyama, T., et al.; "Isolation of tobacco ubiquitin-conjugating enzyme cDNA in a yeast two-hybrid system with tobacco ERF3 as bait and its characterization of specific interaction"; Journal of Experimental Botany (Apr. 2003) 54(385):1175-1181; Oxford University Press; Oxford, UK.
Yanagisawa, S., et al.; "Differential regulation of EIN3 stability by glucose and ethylene signalling in plants"; Nature (Oct. 2, 2003) 425:521-525; Nature Publishing Group; London, UK.
Potuschak, T., et al.; "EIN3-Dependent Regulation of Plant Ethylene Hormone Signaling by Two Arabidopsis F Box Proteins: EBF1 and EBF2"; Cell (Dec. 12, 2003) 115:679-689; Cell Press; Cambridge, MA US.
Binder, B.M., et al.; "The Arabidopsis EIN3 Binding F-Box Proteins EBF1 and EBF2 Have Distinct but Overlapping Roles in Ethylene Signaling"; The Plant Cell (Feb. 2007) 19:509-523; American Society of Plant Biologists; Rockville, MD US.
Tian, Y., and Lu, X.Y.; "The molecular mechanism of ethylene signal transduction"; South African Journal of Botany (2006) 72:487-491; Elsevier, Amsterdam, The Netherland.
Guo, H. and Ecker, J.R.; "Plant Responses to Ethylene Gas are Mediated by SCFEBF1/EBF2-Dependent Proteolysis of EIN3 Transcription Factor"; Cell (Dec. 12, 2003) 115:667-677; Cell Press; Cambridge, MA US.
Li, H. and Guo, H.; "Molecular Basis of the Ethylene Signaling and Response Pathway in Arabidopsis"; J Plant Growth Regul (2007) 26:106-117; Springer Science + Business Media LLC; Berlin/Heidelberg DE.

*Primary Examiner* — Eileen B O Hara
(74) *Attorney, Agent, or Firm* — Pioneer Hi-Bred Int'l, Inc.

(57) ABSTRACT

The invention provides isolated maize EIN3, EBF1 and EIN5 nucleic acids and encoded proteins which are associated with ethylene signaling in plants. The present invention provides methods and compositions relating to altering ethylene sensitivity in plants. The invention further provides recombinant expression cassettes, host cells, transgenic plants and antibody compositions.

11 Claims, 3 Drawing Sheets

MAIZE ETHYLENE SIGNALING GENES AND MODULATION OF SAME FOR IMPROVED STRESS TOLERANCE IN PLANTS

CROSS-REFERENCE TO RELATED APPLICATIONS

This application is a continuation of U.S. Utility patent application Ser. No. 13/354,882 filed Jan. 20, 2012, now U.S. Pat. No. 8,614,368 issued December 24, 2013, which is a continuation of U.S. Utility patent application Ser. No. 12/274,527 filed Nov. 20, 2008, now U.S. Pat. No. 8,129,586 issued Mar. 6, 2012 which claims priority to Provisional Application Ser. No. 60/989,368 filed Nov. 20, 2007, all of which are hereby incorporated by reference in their entirety.

TECHNICAL FIELD

The present invention relates generally to plant molecular biology. More specifically, it relates to nucleic acids and methods for modulating their expression in plants.

BACKGROUND OF THE INVENTION

Plant hormones have been intensively studied for decades for their diverse and complex effects on the plant life. Of the five main hormones-auxins, ethylene, abscisic acid, cytokinins and gibberellins-the molecular signaling and mode of action of ethylene has been the most fully resolved. This progress was made chiefly in the 1990s by the cloning of genes corresponding to mutations in ethylene production and signaling.

Ethylene (C2H4) is a gaseous plant hormone that affects myriad developmental processes and fitness responses in plants, such as germination, flower and leaf senescence, fruit ripening, leaf abscission, root nodulation, programmed cell death and responsiveness to stress and pathogen attack. Over the past decade, genetic screens have identified more than a dozen genes involved in the ethylene response in plants. Ethylene governs diverse processes in plants, and these effects are sometimes affected by the action of other plant hormones, other physiological signals, and the environment, both biotic and abiotic. For example, it is known that cytokinin can cause ethylene like effects through the action of ethylene. In addition, abscisic acid can inhibit ethylene production and signaling. Auxin and ethylene are also known to cooperate in various physiological phenomena. From what is currently known, in general ethylene does not appear to be strictly required for the plant's life cycle, but it does significantly modify development and condition response to stresses.

What is needed in the art is a means to improve agronomic performance in plants, particularly cereal crops such as maize, by modulating ethylene mediated responses in plants.

SUMMARY OF THE INVENTION

This invention involves the identification of maize genes involved in the ethylene signal transduction pathway and the modulation of the same for improving stress tolerance in plants. The invention relates to characterization and modulation of four different maize genes involved in the ethylene pathway including, EIN3, ERF3, EBF1, EBF2 and EIN5 to create plants with an altered response to stress and other ethylene inducing conditions.

Polynucleotides, related polypeptides and all conservatively modified variants of the present maize sequences involved in the ethylene transduction pathway are presented herein. Included are novel and partial maize sequences for the ethylene signaling associated genes including EIN3, ERF3, EBF1, EBF2 and EIN5.

The invention also includes methods to alter the genetic composition of crop plants, especially maize, so that such crops can be more tolerant to stress conditions and other ethylene mediated responses. The utility of this class of invention is then both yield enhancement and stress tolerance.

Ethylene-mediated responses include those involving: crowding tolerance, seed set and development, growth in compacted soils, flooding tolerance, maturation and senescence and disease resistance. This invention provides methods and compositions to effect various alterations in the ethylene-mediated response in a plant that would result in improved agronomic performance, particularly under stress.

Therefore, in one aspect, the present invention relates to an isolated nucleic acid comprising an isolated polynucleotide sequence associated with ethylene signaling in maize. One embodiment of the invention is an isolated polynucleotide comprising a nucleotide sequence selected from the group consisting of: (a) the nucleotide sequence comprising SEQ ID NO: 1 (EIN3), 3 (EBF1), 5 (EBF2), 7 (EIN5) or 9 (ERF3); (b) the nucleotide sequence encoding an amino acid sequence comprising SEQ ID NO: 2, 4, 6, 8 or 10; (c) a polynucleotide having a specified sequence identity to a polynucleotide encoding a polypeptide of the present invention; (d) a polynucleotide which is complementary to the polynucleotide of (a); and, (e) a polynucleotide comprising a specified number of contiguous nucleotides from a polynucleotide of (a) or (b). The isolated nucleic acid can be DNA.

Compositions of the invention include an isolated polypeptide comprising an amino acid sequence selected from the group consisting of: (a) the amino acid sequence comprising SEQ ID NO: 2, 4, 6, 8 or 10 and (b) the amino acid sequence comprising a specified sequence identity to SEQ ID NO: 2, 4, 6, 8 or 10, wherein said polypeptide has ethylene signaling activity.

In another aspect, the present invention relates to a recombinant expression cassette comprising a nucleic acid as described. Additionally, the present invention relates to a vector containing the recombinant expression cassette. Further, the vector containing the recombinant expression cassette can facilitate the transcription and translation of the nucleic acid in a host cell. The present invention also relates to the host cells able to express the polynucleotide of the present invention. A number of host cells could be used, such as but not limited to, microbial, mammalian, plant or insect.

In yet another embodiment, the present invention is directed to a transgenic plant or plant cells, containing the nucleic acids of the present invention. Preferred plants containing the polynucleotides of the present invention include but are not limited to maize, soybean, sunflower, sorghum, canola, wheat, alfalfa, cotton, rice, barley, tomato and millet. In another embodiment, the transgenic plant is a maize plant or plant cells. Another embodiment is a transgenic seed from the transgenic plant.

The plants of the invention can have altered responses to ethylene as compared to a control plant. In some plants, the altered ethylene response is located to a vegetative tissue, a reproductive tissue, or a vegetative tissue and a reproductive tissue. Plants of the invention can have at least one of the following phenotypes including but not limited to: differences in crowding tolerance, seed set and development, growth in compacted soils, flooding tolerance, maturation and senescence and disease resistance compared to non transformed plants.

Another embodiment of the invention would be plants that have been genetically modified at a genomic locus, wherein the genomic locus encodes an ethylene signaling polypeptide of the invention.

Methods for increasing the activity of ethylene signaling polypeptides in a plant are provided. The method can comprise introducing into the plant an ethylene signaling polynucleotide of the invention.

Methods for reducing or eliminating the level of ethylene signaling polypeptide in the plant are also provided. The level or activity of the polypeptide could also be reduced or eliminated in specific tissues, causing alteration in plant growth rate. Reducing the level and/or activity of the ethylene signaling gene will lead to plants with changed responses to the ethylene hormone.

In a further aspect, the present invention relates to a polynucleotide amplified from a *Zea mays* nucleic acid library using primers which selectively hybridize, under stringent hybridization conditions, to loci within polynucleotides of the present invention.

Definitions

Units, prefixes and symbols may be denoted in their SI accepted form. Unless otherwise indicated, nucleic acids are written left to right in 5' to 3' orientation; amino acid sequences are written left to right in amino to carboxy orientation, respectively. Numeric ranges recited within the specification are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical and electronics terms as used herein are as defined in The New IEEE Standard Dictionary of Electrical and Electronics Terms (5th edition, 1993). The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology Principles and Applications, Persing, et al., Ed., American Society for Microbiology, Washington, D.C. (1993). The product of amplification is termed an amplicon.

The term "antibody" includes reference to antigen binding forms of antibodies. The term "antibody" frequently refers to a polypeptide substantially encoded by an immunoglobulin gene or immunoglobulin genes, or fragments thereof which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain FV, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

The term "antigen" includes reference to a substance to which an antibody can be generated and/or to which the antibody is specifically immunoreactive. The specific immunoreactive sites within the antigen are known as epitopes or antigenic determinants. These epitopes can be a linear array of monomers in a polymeric composition-such as amino acids in a protein- or consist of or comprise a more complex secondary or tertiary structure. Those of skill will recognize that all immunogens (i.e., substances capable of eliciting an immune response) are antigens, however some antigens, such as haptens, are not immunogens but may be made immunogenic by coupling to a carrier molecule. An antibody immunologically reactive with a particular antigen can be generated in vivo or by recombinant methods such as selection of libraries of recombinant antibodies in phage or similar vectors. See, e.g., Huse, et al., (1989) *Science* 246:1275-1281; and Ward, et al., (1989) *Nature* 341:544-546 and Vaughan, et al., (1996) *Nature Biotech.* 14:309-314.

As used herein, "antisense orientation" includes reference to a duplex polynucleotide sequence that is operably linked to a promoter in an orientation where the antisense strand is transcribed. The antisense strand is sufficiently complementary to an endogenous transcription product such that translation of the endogenous transcription product is often inhibited.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid.

One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7 or 10 alterations can be made.

Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80% or 90% of the native protein for its native substrate. Conservative substitution tables providing functionally similar amino acids are well known in the art.

The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V) and 6) Phenylalanine (F), Tyrosine (Y), Tryptophan (W). See also, Creighton (1984) Proteins W.H. Freeman and Company.

By "encoding" or "encoded", with respect to a specified nucleic acid, is meant comprising the information for translation into the specified protein. A nucleic acid encoding a protein may comprise intervening sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal and fungal mitochondria, the bacterium *Mycoplasma capricolumn* or the ciliate Macronucleus, may be used when the nucleic acid is expressed therein. When the nucleic acid is prepared or altered synthetically, advantage can be taken of known codon preferences of the intended host where the nucleic acid is to be expressed.

For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray, et al., (1989) *Nucl. Acids Res.* 17:477-498). Thus, the maize preferred codon for a particular amino acid may be derived from known gene sequences from maize. Maize codon usage for 28 genes from maize plants is listed in Table 4 of Murray, et al., supra.

As used herein "full-length sequence" in reference to a specified polynucleotide or its encoded protein means having the entire amino acid sequence of, a native (nonsynthetic), endogenous, biologically active form of the specified protein. Methods to determine whether a sequence is full-length are well known in the art including such exemplary techniques as northern or western blots, primer extension, S 1 protection, and ribonuclease protection. See, e.g., Plant Molecular Biology: A Laboratory Manual, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNN<u>AUG</u>G, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells may be prokaryotic cells such as *E. coli*, or eukaryotic cells such as yeast, insect, amphibian or mammalian cells. Preferably, host cells are monocotyledonous or dicotyledonous plant cells. A particularly preferred monocotyledonous host cell is a maize host cell.

The term "hybridization complex" includes reference to a duplex nucleic acid structure formed by two single-stranded nucleic acid sequences selectively hybridized with each other.

By "immunologically reactive conditions" or "immunoreactive conditions" is meant conditions which allow an antibody, reactive to a particular epitope, to bind to that epitope to a detectably greater degree (e.g., at least 2-fold over background) than the antibody binds to substantially any other epitopes in a reaction mixture comprising the particular epitope. Immunologically reactive conditions are dependent upon the format of the antibody binding reaction and typically are those utilized in immunoassay protocols. See, Harlow and Lane, Antibodies, A Laboratory Manual, Cold Spring Harbor Publications, New York (1988), for a description of immunoassay formats and conditions.

Thus, under designated immunoassay conditions, the specified antibodies bind to an analyte having the recognized epitope to a substantially greater degree (e.g., at least 2-fold over background) than to substantially all analytes lacking the epitope which are present in the sample. Specific binding to an antibody under such conditions may require an antibody that is selected for its specificity for a particular protein. For example, antibodies raised to the polypeptides of the present invention can be selected from to obtain antibodies specifically reactive with polypeptides of the present invention. The proteins used as immunogens can be in native conformation or denatured so as to provide a linear epitope.

A variety of immunoassay formats may be used to select antibodies specifically reactive with a particular protein (or other analyte). For example, solid-phase ELISA immunoassays are routinely used to select monoclonal antibodies specifically immunoreactive with a protein. See, Harlow and Lane, Antibodies, A Laboratory Manual, Cold Spring Harbor Publications, New York (1988), for a description of immunoassay formats and conditions that can be used to determine selective reactivity.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon or transiently expressed (e.g., transfected mRNA). The term "isolated" refers to material, such as a nucleic acid or a protein, which is: (1) substantially or essentially free from components that normally accompany or interact with it as found in its naturally occurring environment. The isolated material optionally comprises material not found with the material in its natural environment or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling, et al., PCT/US93/03868. Likewise, a naturally occurring nucleic acid (e.g., a promoter) becomes isolated if it is introduced by normaturally occurring means to a locus of the genome not native to that nucleic acid. Nucleic acids which are "isolated" as defined herein, are also referred to as "heterologous" nucleic acids.

Unless otherwise stated, the term "EIN3, ERF3, EIN5, EBF1 or EBF2 nucleic acid" is a nucleic acid of the present invention and means a nucleic acid comprising a polynucleotide of the present invention (a "EIN3, ERF3, EIN5, EBF1 or EBF2 polynucleotide") encoding a EIN3, ERF3, EIN5, EBF1 or EBF2 polypeptide. A "EIN3, ERF3, EIN5, EBF1 or EBF2 gene" is a gene of the present invention and refers to a heterologous genomic form of a full-length EIN3, ERF3, EIN5, EBF1 or EBF2 polynucleotide.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes of that pair to be followed. A genotype may be defined by use of one or a plurality of markers.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, Guide to Molecular Cloning Techniques, Methods in Enzymology, Vol. 152, Academic Press, Inc., San Diego, Calif. (Berger); Sambrook, et al., Molecular Cloning-A Laboratory Manual, $2^{nd}$ ed., Vol. 1-3 (1989); and Current Protocols in Molecular Biology, Ausubel, et al., Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen and microspores. The class of plants which can be used in the methods of the invention is generally as broad as the class of higher plants amenable to transformation techniques, including both monocotyledonous and dicotyledonous plants. A particularly preferred plant is Zea mays.

As used herein, "polynucleotide" includes reference to a deoxyribopolynucleotide, ribopolynucleotide or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art.

The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not always entirely linear. For instance, polypeptides may be branched as a result of ubiquitization, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is a plant cell. Exemplary plant promoters include, but are not limited to, those that are obtained from plants, plant viruses and bacteria which comprise genes expressed in plant cells such *Agrobacterium* or *Rhizobium*. Examples of promoters under developmental control include promoters that preferentially initiate transcription in certain tissues, such as leaves, roots, or seeds. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions or the presence of light. Tissue specific, tissue preferred, cell type specific and inducible promoters constitute the class of "non-constitutive" promoters. A "constitutive" promoter is a promoter which is active under most environmental conditions.

The term "EIN3, ERF3, EIN5, EBF1 or EBF2 polypeptide" is a polypeptide of the present invention and refers to one or more amino acid sequences, in glycosylated or non-glycosylated form. The term is also inclusive of fragments, variants, homologs, alleles or precursors (e.g., preproproteins or proproteins) thereof. A "EIN3, ERF3, EIN5, EBF1 or EBF2 protein" is a protein of the present invention and comprises a EIN3, ERF3, EIN5, EBF1 or EBF2 polypeptide.

As used herein "recombinant" includes reference to a cell or vector that has been modified by the introduction of a heterologous nucleic acid, or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "selectively hybridizes" includes reference to hybridization, under stringent hybridization conditions, of a nucleic acid sequence.

The term "stringent conditions" or "stringent hybridization conditions" includes reference to conditions under which a probe will hybridize to its target sequence, to a detectably greater degree than to other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing).

Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA/DNA hybrids, the Tm can be approximated from the equation of Meinkoth and Wahl, (1984) *Anal. Biochem.* 138:267-284: $T_m = 81.5°$ C. $+16.6$ (log M)$+0.41$(% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with >90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3 or 4° C. lower than the thermal melting point (Tm); moderately stringent conditions can utilize a hybridization and/or wash at 6, 7, 8, 9 or 10° C. lower than the thermal melting point (Tm); low stringency conditions can utilize a hybridization and/or wash at 11, 12, 13, 14, 15 or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y. (1993); and Current Protocols in Molecular Biology, Chapter 2, Ausubel, et al., Eds., Greene Publishing and Wiley-Interscience, New York (1995).

A "subject plant" or "subject plant cell" is one in which genetic alteration, such as transformation, has been affected as to a gene of interest or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest or (e) the subject plant or plant cell itself, under conditions in which the gene of interest is not expressed.

In the present case, for example, changes in the ethylene response, including changes in amounts or timing of ethylene production, ethylene activity, ethylene distribution, ethylene signaling or ethylene recognition or changes in plant or plant cell phenotype, such as flowering time, seed set, branching, senescence, stress tolerance or root mass, could be measured by comparing a subject plant or plant cell to a control plant or plant cell.

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between a polynucleotide/polypeptide of the present invention with a reference polynucleotide/polypeptide: (a) "reference sequence", (b) "comparison window", (c) "sequence identity" and (d) "percentage of sequence identity".

(a) As used herein, "reference sequence" is a defined sequence used as a basis for sequence comparison with a polynucleotide/polypeptide of the present invention. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide/polypeptide sequence, wherein the polynucleotide/polypeptide sequence may be compared to a reference sequence and wherein the portion of the polynucleotide/polypeptide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides/amino acids residues in length, and optionally can be 30, 40, 50, 100 or longer. Those of skill in the art understand that to avoid a high similarity to a reference sequence due to inclusion of gaps in the polynucleotide/polypeptide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, (1981) *Adv. Appl. Math.* 2:482; by the homology alignment algorithm of Needleman and Wunsch, (1970) *J. Mol. Biol.* 48:443; by the search for similarity method of Pearson and Lipman, (1988) *Proc. Natl. Acad. Sci.* 85:2444; by computerized implementations of these algorithms, including, but not limited to: CLUSTAL in the PC/Gene program by Intelligenetics, Mountain View, Calif.; GAP, BESTFIT, BLAST, FASTA, and TFASTA in the GCG Wisconsin Package®, Version 10 (available from Accelrys Inc., 9685 Scranton Road, San Diego, Calif., USA). The CLUSTAL program is well described by Higgins and Sharp, (1988) *Gene* 73:237-244; Higgins and Sharp, (1989) *CABIOS* 5:151-153; Corpet, et al., (1988) *Nucleic Acids Research* 16:10881-90; Huang, et al., (1992) *Computer Applications in the Biosciences* 8:155-65, and Pearson, et al., (1994) *Methods in Molecular Biology* 24:307-331.

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences and TBLASTX for nucleotide query sequences against nucleotide database sequences. See, Current Protocols in Molecular Biology, Chapter 19, Ausubel, et al., Eds., Greene Publishing and Wiley-Interscience, New York (1995); Altschul, et al., (1990) *J. Mol. Biol.* 215:403-410 and, Altschul, et al., (1997) *Nucleic Acids Res.* 25:3389-3402.

Software for performing BLAST analyses is publicly available, e.g., through the National Center for Biotechnology Information, National Library of Medicine, Building 38A, Bethesda, Md., USA. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score.

Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see, Henikoff and Henikoff, (1989) *Proc. Natl. Acad. Sci. USA* 89:10915).

In addition to calculating percent sequence identity, the BLAST algorithm also performs a statistical analysis of the similarity between two sequences (see, e.g., Karlin and Altschul, (1993) *Proc. Nat'l. Acad. Sci. USA* 90:5873-5877). One measure of similarity provided by the BLAST algorithm is the smallest sum probability (P (N)), which provides an indication of the probability by which a match between two nucleotide or amino acid sequences would occur by chance. BLAST searches assume that proteins can be modeled as random sequences. However, many real proteins comprise regions of nonrandom sequences which may be homopolymeric tracts, short-period repeats or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) *Comput Chem.* 17:149-163) and XNU (Clayerie and States, (1993) *Comput. Chem.* 17:191-201) low-complexity filters can be employed alone or in combination.

Unless otherwise stated, nucleotide and protein identity/similarity values provided herein are calculated using GAP (GCG Version 10) under default values. GAP (Global Alignment Program) can also be used to compare a polynucleotide or polypeptide of the present invention with a reference sequence. GAP uses the algorithm of Needleman and Wunsch (*J. Mol. Biol.* 48:443-453 (1970)) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 100. Thus, for example, the gap creation and gap extension penalties can each independently be: 3, 4, 5, 6, 7, 8, 9, 10, 15, 20, 30, 40, 50, 60 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) *Proc. Natl. Acad. Sci. USA* 89:10915).

Multiple alignment of the sequences can be performed using the CLUSTAL method of alignment (Higgins and Sharp (1989) *CABIOS* 5:151-153) with the default parameters (GAP PENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) *Computer Applic. Biol. Sci.* 4:11-17, e. <RTI g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

DETAILED DESCRIPTION OF THE INVENTION

Overview

Figure 1:
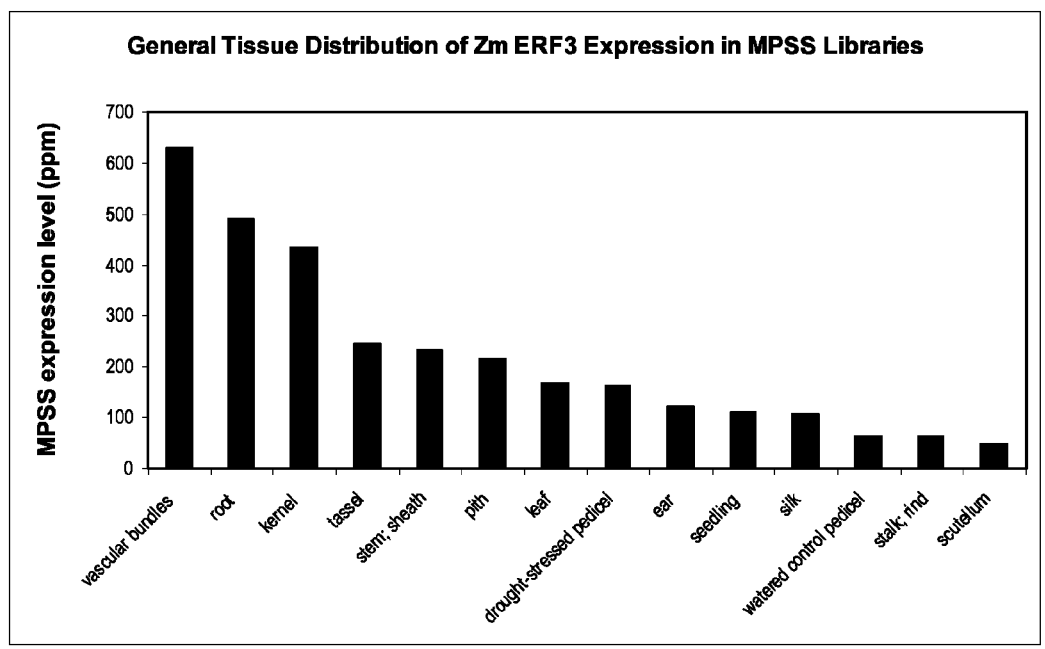
FIG. 1 is a graph showing Tissue distribution of Zm ERF3 expression in MPSS libraries.

The present invention provides, among other things, compositions and methods for modulating (i.e., increasing or decreasing) the level of polynucleotides and polypeptides of the present invention in plants. In particular, the polynucleotides and polypeptides of the present invention can be expressed temporally or spatially, e.g., at developmental stages, in tissues, and/or in quantities, which are uncharacteristic of non-recombinantly engineered plants. Thus, the present invention provides utility in such exemplary applications as provided below.

EIN3 is a nuclear transcription factor that binds to ethylene response elements present in the promoters of ethylene response factors, such as ERF1 or ERF3. Thus down regulation of EIN3 will reduce ethylene sensitivity.

EBF1 and EBF2 are F-box proteins that bind to EIN3 and target the EIN3 protein for degradation through the ubiquitin/proteasome pathway. Thus overexpression of EBF1 and EBF2 will decrease ethylene sensitivity. EIN3 protein levels rapidly increase in response to ethylene and this response requires several ethylene-signaling pathway components including the ethylene receptors (ETR1 and EIN4), CTR1, EIN2, EIN5 and EIN6. In the absence of ethylene, EIN3 is quickly degraded through a ubiquitin/proteasome pathway mediated by EBF1 and EBF2.

EIN5 has endonuclease activity on EBF1 and EBF2 transcripts and thus antagonizes the negative feedback on EIN3 by promoting EBF1 and EBF2 mRNA decay. Thus down regulation of EIN5 will reduce ethylene sensitivity.

Changes in the ethylene response may include one or more changes in amount or timing of ethylene production, ethylene activity, ethylene distribution, ethylene signaling and ethylene recognition, which may result in phenotypic changes such as, for example, altered flowering time, seed set, branching, senescence, stress tolerance, or root formation, In certain embodiments the nucleic acid constructs of the present invention can be used in combination ("stacked") with other polynucleotide sequences of interest in order to create plants with a desired phenotype. The polynucleotides of the present invention may be stacked with any gene or combination of genes, and the combinations generated can include multiple copies of any one or more of the polynucleotides of interest. The desired combination may affect one or more traits; that is, certain combinations may be created for modulation of gene expression affecting ethylene response. Other combinations may be designed to produce plants with a variety of desired traits, such as those described elsewhere herein.

Crowding Tolerance

The agronomic performance of crop plants is often a function of how well they tolerate planting density. The stress of overcrowding can be due to simple limitations of nutrients, water, and sunlight. Crowding stress may also be due to enhanced contact between plants. Plants often respond to physical contact by slowing growth and thickening their tissues.

Ethylene has been implicated in plant crowding tolerance. For example, ethylene insensitive tobacco plants did not slow growth when contacting neighboring plants (Knoester, et al., (1998) *PNAS USA* 95:1933-1937). There is also evidence that ethylene, and the plant's response to it, is involved in water deficit stress, and that ethylene may be causing changes in the plant that limit its growth and aggravate the symptoms of drought stress beyond the loss of water itself.

The present invention provides for decreasing ethylene sensitivity in a plant, in particular cereals such as maize, by modulating the expression or activity of one or more of EIN3, ERF3, EBF1, EBF2 or EIN5 genes or gene products to promote tolerance of close spacing with reduced stress and minimized yield loss.

Seed Set and Development in Maize

Ethylene plays a number of roles in seed development. For example, in maize ethylene is linked to programmed cell death of developing endosperm cells (Young, et al., (1997) *Plant Physio.* 115:737-751). In addition, ethylene is linked to kernel abortion, such as occurs at the tips of ears, especially in plants grown under stressful conditions (Cheng and Lur, (1996) *Physiol. Plant* 98:245-252). Reduced kernel seed set is of course a contributor to reduced yields. Consequently, the present invention provides plants, in particular maize plants that have reduced ethylene action by altering expression of genes involved in the ethylene response.

Growth in Compacted Soils

Plant growth is affected by the density and compaction of soils. Denser, more compacted soils typically result in poorer plant growth. The trend in agriculture towards more minimal till planting and cultivation practices, with the goal of soil and energy conservation, is increasing the need for crop plants that can perform well under these conditions.

Ethylene is well-known to affect plant growth and development, and one effect of ethylene is to promote tissue thickening and growth retardation when encountering mechanical stress, such as compacted soils. This can affect both the roots and shoots. This effect is presumably adaptive in some circumstances in that it results in stronger, more compact tissues that can force their way through or around, obstacles such as compacted soils. However, in such conditions, the production of ethylene and the activation of the ethylene pathway may exceed what is needed for adaptive accommodation to the mechanical stress of the compacted soils. Any resulting unnecessary growth inhibition would be an undesired agronomic result.

The present invention provides for decreasing ethylene sensitivity in a plant, in particular cereals such as maize, by modulating the expression or activity of one or more of EIN3, ERF3, EBF1, EBF2 or EIN5 genes or gene products. Such modulated plants grow and germinate better in compacted soils, resulting in higher stand counts, the herald of higher yields.

Flooding Tolerance

Flooding and water-logged soils causes substantial losses in crop yield each year around the world. Flooding can be both widespread or local, transitory or prolonged. Ethylene has been implicated in flooding mediated damage. In fact, in flooded conditions ethylene production can rise. There are two main reasons for this rise: 1) under such flooded conditions, which creates hypoxia, plants produce more ethylene, and 2) under flooded conditions the diffusion of ethylene away from the plant is slowed, because ethylene is minimally soluble in water, resulting in a rise of intra-plant ethylene levels.

In rice, submergence tolerance is known to be imparted through ethylene signaling (Perata and Voesenek, (2007) *Trends Plant Sci* 12(2):43-46).

Ethylene in flooded maize roots can also inhibit gravitropism, which is normally adaptive during germination in that it orients the roots down and the shoots up. Gravitropism is a factor in determining root architecture, which in turn plays an important role in soil resource acquisition. Manipulation of ethylene levels could be used to impact root angle for drought tolerance, flood tolerance, greater standability and/or improved nutrient uptake. For example, a root growing at a more erect angle (steeper) would likely grow more deeply in soil and thus obtain water at greater depths, improving drought tolerance. In the absence of drought stress a converse argument could be made for more efficient root uptake of nutrients and water in the upper layers of the soil profile, by roots which are more parallel to the soil surface. In general, roots that have a angle nearer that of vertical (steep) are also more susceptible to root lodging than roots with a shallow angle (parallel to the surface) that can be more root lodging resistant.

In addition to inhibition of gravitropism, it is likely that ethylene evolution in flooded conditions inhibits growth, especially of roots. Such inhibition will likely contribute to poor plant growth overall, and consequently is a disadvantageous agronomic trait.

The present invention provides for decreasing ethylene sensitivity in a plant, in particular cereals such as maize, by modulating the expression or activity of one or more of EIN3, ERF3, EBF1, EBF2 or EIN5 genes or gene products. Such plants should grow and germinate better in flooded conditions or water-logged soils, resulting in higher stand counts.

Plant Maturation and Senescence

Ethylene is known to be involved in controlling senescence, fruit ripening, and abscission. The role of ethylene in fruit ripening is well-established and industrially applied. It is expected that ethylene underproduction/insensitivity would result in slower seed maturation or fruit ripening, and the converse would result in more rapid seed maturation or fruit ripening. Abscission is primarily studied for dicot plants and apparently has little application to monocots such as cereals. Ethylene mediated senescence also is mostly studied in dicots, but control of senescence is agronomically important for both dicot and monocot crop species. Ethylene insensitivity can delay, but not arrest, senescence. The senescence process mediated by ethylene bears some similarities to the cell death process in disease symptoms and in abscission zones. Controlling ethylene sensitivity, as through the control of one or more of the ERF3, EIN3, EBF1, EBF2, EIN5 genes could result in modulation of maturity rates for crop plants such as maize.

The present invention provides for decreasing ethylene sensitivity in a plant, in particular cereals such as maize, by modulating the expression or activity of one or more of EIN3, ERF3, EBF1, EBF2 or EIN5 genes which may contribute to a later maturing plant, which is desirable for placing crop varieties in different maturity zones.

Tolerance to Other Abiotic Stresses

Many stresses on plants induce production of ethylene (see, Morgan and Drew, (1997) *Physiol. Plant* 100:620-630). These stresses can be, for example, cold, heat, wounding, pollution, drought, and hypersalinity. Mechanical impedance (soil compaction) and flooding stresses were addressed above. It appears that several of these stresses operate through common mechanisms, such as water deficit. Clearly drought causes water deficit, crowding stress may also cause water deficit. Additionally, in maize, chilling can cause an elevation in ethylene production and activity, and this induction is apparently due to chilling causing water deficit in cells (Janowaik and Dorffling, (1995) *J. Plant Physiol.* 147:257-262).

Some of the ethylene production following stresses may serve an adaptive purpose by regulating ethylene-mediated processes in the plant that result in a plant reorganized in such manner to better acclimate to the stress encountered. However, there is also evidence that ethylene production during stress can result in an aggravation of negative symptoms resulting from the stress, such as yellowing, tissue death and senescence.

To the extent that ethylene production during stress causes or augments negative stress-related symptoms, it would be desirable to create a crop plant that is less sensitive to the ethylene. Towards that end, the present invention provides for decreasing ethylene sensitivity in a plant, in particular cereals such as maize, by modulating the expression or activity of one or more of EIN3, ERF3, EBF1, EBF2 or EIN5 genes or gene products to create plants that are less able to produce ethylene mediated effects.

Disease Resistance

Crop plants can be susceptible to a wide variety of pathogens, whether viruses, bacteria, fungi or insects. This susceptibility results in large crop yield losses annually worldwide. Crop breeders have endeavored to breed more resistant or tolerant varieties which can withstand pathogen attack. Additional genetic engineering strategies seek the same end. In many plant-pathogen interactions the symptoms of disease, most often tissue necrosis and resulting poor plant growth, is known to be the result of an active plant defense response to the pathogen. That is, the symptoms are caused directly by the plant and not simply by the pathogen. From among the list of all crop plants and their potential list of pathogens, resistance is the rule, and susceptibility the exception. Susceptible interactions are often thought to result from an improper or insufficient activation defense by the plant that results in increased symptom development and an inability to contain the pathogen.

Ethylene is known to be associated with plant pathogen defense systems. Many pathogenesis related genes are induced in expression at the level of mRNA by ethylene. The trend in our understanding of the role of ethylene in plant pathogen defense is towards ethylene and ethylene mediated effects being viewed as principally part of the downstream reactions to pathogen attack, as in symptom development. Ethylene seems to be involved in the plant's response to the stress of pathogen attack and in tissue damage inflicted by the pathogen. In a susceptible interaction ethylene may actually promote tissue damage. Consequently in such situations blocking ethylene production or action may actually result in less tissue damage, that is, more apparent resistance, even though the pathogen is compatible with the plant. Blocking ethylene action is known to either result in more susceptibility (e.g., Knoester, et al., (1988)) or more resistance (e.g., Lund, et al., (1998) *Plant Cell* 10:371-382), which indicates that the role of ethylene action is complex, as is to be expected, for it depends upon the interactions of diverse plants and pathogens.

The present invention provides for the use of one or more of EIN3, ERF3, EBF1, EBF2 or EIN5 genes to affect enhanced resistance to plant pathogens, in particular for monocots such as maize.

For most applications this will involve the reduction in ethylene signaling by modulating the expression or activity of EIN3, ERF3, EBF1, EBF2 or EIN5 genes or gene products, with the goal of causing plants that responds less to ethylene and thereby plants that are less prone to tissue damage following pathogen infection.

It is recognized that for some pathogens, ethylene signaling may be necessary for achieving substantial resistance. This can be handled by linking a functional ethylene sensitivity gene to a pathogen-inducible promoter, in particular to a promoter whose induction is preferentially responsive to the pathogen or pathogens for which plant ethylene signaling is desired for achievement of active resistance.

Plant Transformation

The generation of transgenic plants is central to crop plant genetic engineering strategies. Transgenesis typically involves the introduction of exogenous DNA into the plants cells via a variety of methods, such as particle bombardment or *agrobacterium* infection, which is usually followed by tissue culture and plant regeneration. Transgenic plant production remains a costly and rate limiting step in genetic engineering, especially for many of the most economically important crop plants, such as the cereals, like maize.

Improving the efficiency of this process is therefore of great importance.

It has been accepted for a long time that ethylene action has negative consequences for plant transformation. As a result various approaches to bind, trap or otherwise block the accumulation of ethylene are employed in transformation and tissue culture (see, Songstad, et al., (1991) *Plant Cell Reports* 9:694-702). The particle bombardment method causes substantial tissue/cell damage, and such damage is known to elicit ethylene accumulation. Moreover, in most tissue culture methods, some tissue grows better than others, as is designed in chemical selection of transformants. Such dying tissue can emit ethylene and cause inhibition of positive transformants. Aggravating these effects is the confinement of plant tissues in containers for the purpose of tissue regeneration, that can result in the accumulation of ethylene, also causing growth retardation. As ethylene is known to reduce tissue growth rates and even advance cell/tissue death, having a means to block or minimize ethylene action during transformation is desired.

Consequently, the present invention also provides for the use of an EIN3, ERF3, EBF1, EBF2 or EIN5 gene to create transient or stable reductions in ethylene action by diminishing the expression and/or activity of one or more of the EIN3, ERF3, EBF1, EBF2 or EIN5 genes.

Other Utilities

The present invention also provides isolated nucleic acids comprising polynucleotides of sufficient length and complementarity to a gene of the present invention to use as probes or amplification primers in the detection, quantitation or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions or additions), for monitoring upregulation of expression or changes in enzyme activity in screening assays of compounds, for detection of any number of allelic variants (polymorphisms), orthologs, or paralogs of the gene, or for site directed mutagenesis in eukaryotic cells (see, e.g., U.S. Pat. No. 5,565,350). The isolated nucleic acids of the present invention can also be used for recombinant expression of their encoded polypeptides, or for use as immunogens in the preparation and/or screening of antibodies. The isolated nucleic acids of the present invention can also be employed for use in sense or antisense suppression of one or more genes of the present invention in a host cell, tissue, or plant. Attachment of chemical agents which bind, intercalate, cleave and/or cross-link to the isolated nucleic acids of the present invention can also be used to modulate transcription or translation.

The present invention also provides isolated proteins comprising a polypeptide of the present invention (e.g., preproenzyme, proenzyme or enzymes). The present invention also provides proteins comprising at least one epitope from a polypeptide of the present invention. The proteins of the present invention can be employed in assays for enzyme agonists or antagonists of enzyme function, or for use as immunogens or antigens to obtain antibodies specifically immunoreactive with a protein of the present invention. Such antibodies can be used in assays for expression levels, for identifying and/or isolating nucleic acids of the present invention from expression libraries, for identification of homologous polypeptides from other species, or for purification of polypeptides of the present invention.

The isolated nucleic acids and polypeptides of the present invention can be used over a broad range of plant types, particularly monocots such as the species of the family Gramineae including *Hordeum*, *Secale*, *Tritium*, *Sorghum* (e.g., *S. bicolor*) and *Zea* (e.g., *Z. mays*). The isolated nucleic acid and proteins of the present invention can also be used in species from the genera: *Cucurbita*, *Rosa*, *Vitis*, *Juglans*, *Fragaria*, *Lotus*, *Medicago*, *Onobrychis*, *Trifolium*, *Trigonella*, *Vigna*, *Citrus*, *Linum*, *Geranium*, *Manihot*, *Daucus*, *Arabidopsis*, *Brassica*, *Raphanus*, *Sinapis*, *Atropa*, *Capsicum*, *Datura*, *Hyoscyamus*, *Lycopersicon*, *Nicotiana*, *Solanum*, *Petunia*, *Digitalis*, *Majorana*, *Clahorium*, *Helianthus*, *Lactuca*, *Bromus*, *Asparagus*, *Antirrhinum*, *Heterocallis*, *Nemesis*, *Pelargonium*, *Panieum*, *Pennisetum*, *Ranunculus*, *Senecio*, *Salpiglossis*, *Cucumis*, *Browallia*, *Glycine*, *Pisum*, *Phaseolus*, *Lolium*, *Oryza* and *Avena*.

Nucleic Acids

The present invention provides, among other things, isolated nucleic acids of RNA, DNA, and analogs and/or chimeras thereof, comprising a polynucleotide of the present invention.

A polynucleotide of the present invention is inclusive of:

(a) a polynucleotide encoding a polypeptide of SEQ ID NOS: 2, 4, 6, 8 or 10, and conservatively modified and polymorphic variants thereof, including exemplary polynucleotides of SEQ ID NOS: 1 (EIN3), 3 (EBF1), 5 (EBF2), 7 (EIN5) or 9 (ERF3);

(b) an isolated polynucleotide which is the product of amplification from a plant nucleic acid library using primer pairs which selectively hybridize under stringent conditions to loci within a polynucleotide of the present invention;

(c) an isolated polynucleotide which selectively hybridizes to a polynucleotide of (a) or (b);

(d) an isolated polynucleotide having a specified sequence identity with polynucleotides of (a), (b) or (c);

(e) an isolated polynucleotide encoding a protein having a specified number of contiguous amino acids from a prototype polypeptide, wherein the protein is specifically recognized by antisera elicited by presentation of the protein and wherein the protein does not detectably immunoreact to antisera which has been fully immunosorbed with the protein;

(f) complementary sequences of polynucleotides of (a), (b), (c), (d) or (e); and (g) an isolated polynucleotide comprising at least a specific number of contiguous nucleotides from a polynucleotide of (a), (b), (c), (d), (e) or (f);

(h) an isolated polynucleotide from a full-length enriched cDNA library having the physico-chemical property of selectively hybridizing to a polynucleotide of (a), (b), (c), (d), (e), (f) or (g);

(i) an isolated polynucleotide made by the process of: 1) providing a full-length enriched nucleic acid library, 2) selectively hybridizing the polynucleotide to a polynucleotide of (a), (b), (c), (d), (e), (f), (g) or (h), thereby isolating the polynucleotide from the nucleic acid library.

A. Polynucleotides Encoding a Polypeptide of the Present Invention

As indicated in (a), above, the present invention provides isolated nucleic acids comprising a polynucleotide of the present invention, wherein the polynucleotide encodes a polypeptide of the present invention. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Thus, each silent variation of a nucleic acid which encodes a polypeptide of the present invention is implicit in each described polypeptide sequence and is within the scope of the present invention. Accordingly, the present invention includes polynucleotides of the present invention and polynucleotides encoding a polypeptide of the present invention.

B. Polynucleotides Amplified from a Plant Nucleic Acid Library

As indicated in (b), above, the present invention provides an isolated nucleic acid comprising a polynucleotide of the present invention, wherein the polynucleotides are amplified, under nucleic acid amplification conditions, from a plant nucleic acid library.

Nucleic acid amplification conditions for each of the variety of amplification methods are well known to those of ordinary skill in the art. The plant nucleic acid library can be constructed from a monocot such as a cereal crop. Exemplary cereals include corn, sorghum, alfalfa, canola, wheat or rice. The plant nucleic acid library can also be constructed from a dicot such as soybean. Zea mays lines B73, PHRE1, A632, BMP2#10, W23 and Mol7 are known and publicly available. Other publicly known and available maize lines can be obtained from the Maize Genetics Cooperation (Urbana, Ill.).

Wheat lines are available from the Wheat Genetics Resource Center (Manhattan, Kans.). The nucleic acid library may be a cDNA library, a genomic library, or a library generally constructed from nuclear transcripts at any stage of intron processing. cDNA libraries can be normalized to increase the representation of relatively rare cDNAs. In optional embodiments, the cDNA library is constructed using an enriched full-length cDNA synthesis method. Examples of such methods include Oligo-Capping (Maruyama and Sugano, (1994) *Gene* 138:171-174), Biotinylated CAP Trapper (Carninci, et al., (1996) *Genomics* 37:327-336) and CAP Retention Procedure (Edery, et al., (1995) *Molecular and Cellular Biology* 15:3363-3371). Rapidly growing tissues or rapidly dividing cells are preferred for use as an mRNA source for construction of a cDNA library. Growth stages of corn are described in "How a Corn Plant Develops, "Special Report No. 48, Iowa State University of Science and Technology Cooperative Extension Service, Ames, Iowa, Reprinted February 1993.

A polynucleotide of this embodiment (or subsequences thereof) can be obtained, for example, by using amplification primers which are selectively hybridized and primer extended, under nucleic acid amplification conditions, to at least two sites within a polynucleotide of the present invention, or to two sites within the nucleic acid which flank and comprise a polynucleotide of the present invention, or to a site within a polynucleotide of the present invention and a site within the nucleic acid which comprises it. Methods for obtaining 5' and/or 3' ends of a vector insert are well known in the art. See, e.g., RACE (Rapid Amplification of Complementary Ends) as described in Frohman, in PCR Protocols: A Guide to Methods and Applications, Innis, et al., Eds. (Academic Press, Inc., San Diego), pp. 28-38 (1990)); see also, U.S. Pat. No. 5,470,722, and Current Protocols in Molecular Biology, Unit 15.6, Ausubel, et al., Eds., Greene Publishing and Wiley-Interscience, New York (1995); Frohman and Martin, (1989) *Techniques* 1:165.

Optionally, the primers are complementary to a subsequence of the target nucleic acid which they amplify but may have a sequence identity ranging from about 85% to 99% relative to the polynucleotide sequence which they are designed to anneal to. As those skilled in the art will appreciate, the sites to which the primer pairs will selectively hybridize are chosen such that a single contiguous nucleic acid can be formed under the desired nucleic acid amplification conditions. The primer length in nucleotides is selected from the group of integers consisting of from at least 15 to 50. Thus, the primers can be at least 15, 18, 20, 25, 30, 40 or 50 nucleotides in length. Those of skill will recognize that a lengthened primer sequence can be employed to increase specificity of binding (i.e., annealing) to a target sequence. A non-annealing sequence at the 5' end of a primer (a "tail") can be added, for example, to introduce a cloning site at the terminal ends of the amplicon.

The amplification products can be translated using expression systems well known to those of skill in the art. The resulting translation products can be confirmed as polypeptides of the present invention by, for example, assaying for the appropriate catalytic activity (e.g., specific activity and/or substrate specificity) or verifying the presence of one or more epitopes which are specific to a polypeptide of the present invention. Methods for protein synthesis from PCR derived templates are known in the art and available commercially. See, e.g., Amersham Life Sciences, Inc, Catalog '97, p. 354.

C. Polynucleotides which Selectively Hybridize to a Polynucleotide of (A) or (B)

As indicated in (c), above, the present invention provides isolated nucleic acids comprising polynucleotides of the present invention, wherein the polynucleotides selectively hybridize, under selective hybridization conditions, to a polynucleotide of sections (A) or (B) as discussed above. Thus, the polynucleotides of this embodiment can be used for isolating, detecting, and/or quantifying nucleic acids comprising the polynucleotides of (A) or (B). For example, polynucleotides of the present invention can be used to identify, isolate or amplify partial or full-length clones in a deposited library.

In some embodiments, the polynucleotides are genomic or cDNA sequences isolated or otherwise complementary to a cDNA from a dicot or monocot nucleic acid library.

Exemplary species of monocots and dicots include, but are not limited to: maize, canola, soybean, cotton, wheat, sorghum, sunflower, alfalfa, oats, sugar cane, millet, barley and rice. The cDNA library comprises at least 50% to 95% full-length sequences (for example, at least 50%, 60%, 70%, 80% 90% or 95% full-length sequences). The cDNA libraries can be normalized to increase the representation of rare sequences. See, e.g., U.S. Pat. No. 5,482,845. Low stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% to 80% sequence identity and can be employed to identify orthologous or paralogous sequences.

D. Polynucleotides Having a Specific Sequence Identity with the Polynucleotides of (A), (B) or (C)

As indicated in (d), above, the present invention provides isolated nucleic acids comprising polynucleotides of the present invention, wherein the polynucleotides have a specified identity at the nucleotide level to a polynucleotide as disclosed above in sections (A), (B) or (C), above. Identity can be calculated using, for example, the BLAST, CLUSTALW or GAP algorithms under default conditions. The percentage of identity to a reference sequence is at least 60% and, rounded upwards to the nearest integer, can be expressed as an integer selected from the group of integers consisting of from 60 to 99. Thus, for example, the percentage of identity to a reference sequence can be at least 70%, 75%, 80%, 85%, 90% or 95%.

Optionally, the polynucleotides of this embodiment will encode a polypeptide that will share an epitope with a polypeptide encoded by the polynucleotides of sections (A), (B) or (C). Thus, these polynucleotides encode a first polypeptide which elicits production of antisera comprising antibodies which are specifically reactive to a second polypeptide encoded by a polynucleotide of (A), (B) or (C). However, the first polypeptide does not bind to antisera raised against itself when the antisera has been fully immunosorbed with the first polypeptide. Hence, the polynucleotides of this embodiment can be used to generate antibodies for use in, for example, the screening of expression libraries for nucleic acids comprising polynucleotides of (A), (B) or (C), or for purification of, or in immunoassays for, polypeptides encoded by the polynucleotides of (A), (B) or (C). The polynucleotides of this embodiment comprise nucleic acid sequences which can be employed for selective hybridization to a polynucleotide encoding a polypeptide of the present invention.

Screening polypeptides for specific binding to antisera can be conveniently achieved using peptide display libraries. This method involves the screening of large collections of peptides for individual members having the desired function or structure.

Antibody screening of peptide display libraries is well known in the art. The displayed peptide sequences can be from 3 to 5000 or more amino acids in length, frequently from 5 100 amino acids long, and often from about 8 to 15 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Numbers 1991/17271, 1991/18980, 1991/19818 and 1993/08278. Other systems for generating libraries of peptides have aspects of both in vitro chemical synthesis and recombinant methods. See, PCT Patent Publication Numbers 1992/05258, 1992/14843 and 1997/20078. See also, U.S. Pat. Nos. 5,658, 754 and 5,643,768. Peptide display libraries, vectors, and screening kits are commercially available from such suppliers as Invitrogen (Carlsbad, Calif.).

E. Polynucleotides Encoding a Protein Having a Subsequence from a Prototype Polypeptide and Cross-Reactive to the Prototype Polypeptide As indicated in (e), above, the present invention provides isolated nucleic acids comprising polynucleotides of the present invention, wherein the polynucleotides encode a protein having a subsequence of contiguous amino acids from a prototype polypeptide of the present invention such as are provided in (a), above. The length of contiguous amino acids from the prototype polypeptide is selected from the group of integers consisting of from at least 10 to the number of amino acids within the prototype sequence. Thus, for example, the polynucleotide can encode a polypeptide having a subsequence having at least 10, 15, 20, 25, 30, 35, 40, 45 or 50, contiguous amino acids from the prototype polypeptide. Further, the number of such subsequences encoded by a polynucleotide of the instant embodiment can be any integer selected from the group consisting of from 1 to 20, such as 2, 3, 4 or 5. The subsequences can be separated by any integer of nucleotides from 1 to the number of nucleotides in the sequence such as at least 5, 10, 15, 25, 50, 100 or 200 nucleotides.

The proteins encoded by polynucleotides of this embodiment, when presented as an immunogen, elicit the production of polyclonal antibodies which specifically bind to a prototype polypeptide such as but not limited to, a polypeptide encoded by the polynucleotide of (a) or (b), above. Generally, however, a protein encoded by a polynucleotide of this embodiment does not bind to antisera raised against the prototype polypeptide when the antisera has been fully immunosorbed with the prototype polypeptide. Methods of making and assaying for antibody binding specificity/affinity are well known in the art. Exemplary immunoassay formats include ELISA, competitive immunoassays, radioimmunoassays, Western blots, indirect immunofluorescent assays and the like.

In a preferred assay method, fully immunosorbed and pooled antisera which is elicited to the prototype polypeptide can be used in a competitive binding assay to test the protein. The concentration of the prototype polypeptide required to inhibit 50% of the binding of the antisera to the prototype polypeptide is determined. If the amount of the protein required to inhibit binding is less than twice the amount of the prototype protein, then the protein is said to specifically bind to the antisera elicited to the immunogen.

Accordingly, the proteins of the present invention embrace allelic variants, conservatively modified variants, and minor recombinant modifications to a prototype polypeptide.

A polynucleotide of the present invention optionally encodes a protein having a molecular weight as the non-glycosylated protein within 20% of the molecular weight of the full-length non-glycosylated polypeptides of the present invention. Molecular weight can be readily determined by SDS-PAGE under reducing conditions. Optionally, the molecular weight is within 15% of a full length polypeptide of the present invention, more preferably within 10% or 5%, and most preferably within 3%, 2% or 1% of a full length polypeptide of the present invention. Optionally, the polynucleotides of this embodiment will encode a protein having a specific enzymatic activity at least 50%, 60%, 80% or 90% of a cellular extract comprising the native, endogenous full-length polypeptide of the present invention.

Further, the proteins encoded by polynucleotides of this embodiment will optionally have a substantially similar affinity constant ($K_m$) and/or catalytic activity (i.e., the microscopic rate constant, $k_{cat}$) as the native endogenous, full-length protein. Those of skill in the art will recognize that $k_{cat}/K_m$ value determines the specificity for competing substrates and is often referred to as the specificity constant. Proteins of this embodiment can have a $k_{cat}/K_m$ value at least 10% of a full-length polypeptide of the present invention as determined using the endogenous substrate of that polypeptide. Optionally, the $k_{cat}/K_m$ value will be at least 20%, 30%, 40%, 50% and most preferably at least 60%, 70%, 80%, 90% or 95% the $k_{cat}/K_m$ value of the full-length polypeptide of the present invention.

Determination of $k_{cat}$, $K_m$, and $k_{cat}/K_m$ can be determined by any number of means well known to those of skill in the art. For example, the initial rates (i.e., the first 5% or less of the reaction) can be determined using rapid mixing and sampling techniques (e.g., continuous-flow, stopped-flow or rapid quenching techniques), flash photolysis or relaxation methods (e.g., temperature jumps) in conjunction with such exemplary methods of measuring as spectrophotometry, spectrofluorimetry, nuclear magnetic resonance or radioactive procedures. Kinetic values are conveniently obtained using a Lineweaver Burk or Eadie-Hofstee plot.

F. Polynucleotides Complementary to the Polynucleotides of (A)-(E)

As indicated in (f), above, the present invention provides isolated nucleic acids comprising polynucleotides complementary to the polynucleotides of paragraphs A-E, above. As those of skill in the art will recognize, complementary sequences base-pair throughout the entirety of their length with the polynucleotides of sections (A)-(E) (i.e., have 100% sequence identity over their entire length). Complementary bases associate through hydrogen bonding in double stranded nucleic acids. For example, the following base pairs are complementary: guanine and cytosine; adenine and thymine; and adenine and uracil.

G. Polynucleotides Which are Subsequences of the Polynucleotides of (A)-(F)

As indicated in (g), above, the present invention provides isolated nucleic acids comprising polynucleotides which comprise at least 15 contiguous bases from the polynucleotides of sections (A) through (F) as discussed above. The length of the polynucleotide is given as an integer selected from the group consisting of from at least 15 to the length of the nucleic acid sequence from which the polynucleotide is a subsequence of. Thus, for example, polynucleotides of the present invention are inclusive of polynucleotides comprising at least 15, 20, 25, 30, 40, 50, 60, 75 or 100 contiguous nucleotides in length from the polynucleotides of (A)-(F). Optionally, the number of such subsequences encoded by a polynucleotide of the instant embodiment can be any integer selected from the group consisting of from 1 to 20, such as 2, 3, 4 or 5. The subsequences can be separated by any integer of nucleotides from 1 to the number of nucleotides in the sequence such as at least 5, 10, 15, 25, 50, 100 or 200 nucleotides.

Subsequences can be made by in vitro synthetic, in vitro biosynthetic or in vivo recombinant methods. In optional embodiments, subsequences can be made by nucleic acid amplification. For example, nucleic acid primers will be constructed to selectively hybridize to a sequence (or its complement) within, or co-extensive with, the coding region.

The subsequences of the present invention can comprise structural libraries are known in the art and discussed briefly below. The cDNA library comprises at least 50% to 95% full-length sequences (for example, at least 50%, 60%, 70%, 80%, 90% or 95% full-length sequences). The cDNA library can be constructed from a variety of tissues from a monocot or dicot at a variety of developmental stages. Exemplary species include maize, wheat, rice, canola, soybean, cotton, sorghum, sunflower, alfalfa, oats, sugar cane, millet, barley and rice. Methods of selectively hybridizing, under selective hybridization conditions, a polynucleotide from a full-length enriched library to a polynucleotide of the present invention are known to those of ordinary skill in the art. Any number of stringency conditions can be employed to allow for selective hybridization. In optional embodiments, the stringency allows for selective hybridization of sequences having at least 70%, 75%, 80%, 85%, 90%, 95% or 98% sequence identity over the length of the hybridized region. Full-length enriched cDNA libraries can be normalized to increase the representation of rare sequences.

I. Polynucleotide Products Made by a cDNA Isolation Process

As indicated in (I), above, the present invention provides an isolated polynucleotide made by the process of: 1) providing a full-length enriched nucleic acid library, 2) selectively hybridizing the polynucleotide to a polynucleotide of paragraphs (A), (B), (C), (D), (E), (F), (G) or (H) as discussed above, and thereby isolating the polynucleotide from the nucleic acid library. Full-length enriched nucleic acid libraries are constructed as discussed in paragraph (G) and below. Selective hybridization conditions are as discussed in paragraph (G). Nucleic acid purification procedures are well known in the art.

Purification can be conveniently accomplished using solid-phase methods; such methods are well known to those of skill in the art and kits are available from commercial suppliers such as Advanced Biotechnologies (Surrey, UK). For example, a polynucleotide of paragraphs (A)-(H) can be immobilized to a solid support such as a membrane, bead or particle. See, e.g., U.S. Pat. No. 5,667,976. The polynucleotide product of the present process is selectively hybridized to an immobilized polynucleotide and the solid support is subsequently isolated from non-hybridized polynucleotides by methods including, but not limited to, centrifugation, magnetic separation, filtration, electrophoresis and the like.

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot such as corn, rice or wheat or a dicot such as soybean.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexahistidine marker sequence provides a convenient means to purify the proteins of the present invention. A polynucleotide of the present invention can be attached to a vector, adapter, or linker for cloning and/or expression of a polynucleotide of the present invention. Additional sequences may be added to such cloning and/or expression sequences to optimize their function in cloning and/or expression, to aid in isolation of the polynucleotide or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters and linkers is well known and extensively described in the art. For a description of various nucleic acids see, for example, Stratagene Cloning Systems, Catalogs 1999 (La Jolla, Calif.) and Amersham Life Sciences, Inc, Catalog '99 (Arlington Heights, Ill.).

A. Recombinant Methods for Constructing Nucleic Acids

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library. Isolation of RNA, and construction of cDNA and genomic libraries is well known to those of ordinary skill in the art. See, e.g., Plant Molecular Biology: A Laboratory Manual, Clark, Ed., Springer-Verlag, Berlin (1997); and Current Protocols in Molecular Biology, Ausubel, et al., Eds., Greene Publishing and Wiley-Interscience, New York (1995).

A1. Full-Length Enriched cDNA Libraries

A number of cDNA synthesis protocols have been described which provide enriched full-length cDNA libraries. Enriched full-length cDNA libraries are constructed to comprise at least 60%, and more preferably at least 70%, 80%, 90% or 95% full-length inserts amongst clones containing inserts. The length of insert in such libraries can be at least 2, 3, 4, 5, 6, 7, 8, 9, 10 or more kilobase pairs. Vectors to accommodate inserts of these sizes are known in the art and available commercially. See, e.g., Stratagene's lambda ZAP Express (cDNA cloning vector with 0 to 12 kb cloning capacity). An exemplary method of constructing a greater than 95% pure full-length cDNA library is described by Carninci, et al., (1996) Genomics 37:327-336. Other methods for producing full-length libraries are known in the art. See, e.g., Edery, et al., (1995) *Mol. Cell Biol.* 15(6):3363-3371 and PCT Application WO 1996/34981.

A2 Normalized or Subtracted cDNA Libraries

A non-normalized cDNA library represents the mRNA population of the tissue it was made from. Since unique clones are out-numbered by clones derived from highly expressed genes their isolation can be laborious. Normalization of a cDNA library is the process of creating a library in which each clone is more equally represented. Construction of normalized libraries is described in Ko, (1990) *Nucl. Acids. Res.* 18(19):5705-5711; Patanjali, et al., (1991) *Proc. Natl. Acad. USA* 88:1943-1947; U.S. Pat. Nos. 5,482,685, 5,482, 845 and 5,637,685. In an exemplary method described by Soares, et al., normalization resulted in reduction of the abundance of clones from a range of four orders of magnitude to a narrow range of only 1 order of magnitude. *Proc. Natl. Acad. Sci. USA*, 91:9228-9232 (1994).

Subtracted cDNA libraries are another means to increase the proportion of less abundant cDNA species. In this procedure, cDNA prepared from one pool of mRNA is depleted of sequences present in a second pool of mRNA by hybridization. The cDNA: mRNA hybrids are removed and the remaining un-hybridized cDNA pool is enriched for sequences unique to that pool. See, Foote, et al., in, Plant Molecular Biology: A Laboratory Manual, Clark, Ed., Springer-Verlag, Berlin (1997); Kho and Zarbl, (1991) *Technique* 3(2):58-63; Sive and St. John, (1988) *Nucl. Acids Res.* 16(22):10937; Current Protocols in Molecular Biology, Ausubel, et al., Eds., Greene Publishing and Wiley-Interscience, New York (1995); and Swaroop, et al., (1991) *Nucl. Acids Res.* 19(8):1954. cDNA subtraction kits are commercially available. See, e.g., PCR-Select (Clontech, Palo Alto, Calif.).

To construct genomic libraries, large segments of genomic DNA are generated by fragmentation, e.g., using restriction endonucleases, and are ligated with vector DNA to form concatemers that can be packaged into the appropriate vector. Methodologies to accomplish these ends, and sequencing methods to verify the sequence of nucleic acids are well known in the art. Examples of appropriate molecular biological techniques and instructions sufficient to direct persons of skill through many construction, cloning, and screening methodologies are found in Sambrook, et al., Molecular Cloning: A Laboratory Manual, 2nd Ed., Cold Spring Harbor Laboratory Vols. 1-3 (1989), Methods in Enzymology, Vol. 152: Guide to Molecular Cloning Techniques, Berger and Kimmel, Eds., San Diego: Academic Press, Inc. (1987), Current Protocols in Molecular Biology, Ausubel, et al., Eds., Greene Publishing and Wiley-Interscience, New York (1995); Plant Molecular Biology: A Laboratory Manual, Clark, Ed., Springer-Verlag, Berlin (1997). Kits for construction of genomic libraries are also commercially available.

The cDNA or genomic library can be screened using a probe based upon the sequence of a polynucleotide of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. The T4 gene 32 protein (Boehringer Mannheim) can be used to improve yield of long PCR products.

PCR-based screening methods have been described. Wilfinger, et al., describe a PCR-based method in which the longest cDNA is identified in the first step so that incomplete clones can be eliminated from study. *Bio Techniques* 22(3): 481-486 (1997). Such methods are particularly effective in combination with a full-length cDNA construction methodology, above.

B. Synthetic Methods for Constructing Nucleic Acids

The isolated nucleic acids of the present invention can also be prepared by direct chemical synthesis by methods such as the phosphotriester method of Narang, et al., (1979) *Meth. Enzymol.* 68:90-99; the phosphodiester method of Brown, et al., (1979) *Meth. Enzymol.* 68:109-151; the diethylphosphoramidite method of Beaucage, et al., (1981) *Tetra. Lett.* 22:1859-1862; the solid phase phosphoramidite triester method described by Beaucage and Caruthers, (1981) *Tetra. Letts.* 22(20):1859-1862, e.g., using an automated synthesizer, e.g., as described in Needham-VanDevanter, et al., (1984) *Nucleic Acids Res.* 12:6159-6168; and the solid support method of U.S. Pat. No. 4,458,066. Chemical synthesis generally produces a single stranded oligonucleotide. This may be converted into double stranded DNA by hybridization with a complementary sequence or by polymerization with a DNA polymerase using the single strand as a template. One of skill will recognize that while chemical synthesis of DNA is best employed for sequences of about 100 bases or less, longer sequences may be obtained by the ligation of shorter sequences.

Recombinant Expression Cassettes

The present invention further provides recombinant expression cassettes comprising a nucleic acid of the present invention. A nucleic acid sequence coding for the desired polypeptide of the present invention, for example a cDNA or a genomic sequence encoding a full length polypeptide of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include: (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site and/or a polyadenylation signal.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, theGRP1-8 promoter and other transcription initiation regions from various plant genes known to those of skill.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions, or the presence of light. Examples of inducible promoters are the Adhl promoter which is inducible by hypoxia or cold stress, the Hsp70 promoter which is inducible by heat stress, and the PPDK promoter which is inducible by light.

Examples of promoters under developmental control include promoters that initiate transcription only, or preferentially, in certain tissues, such as leaves, roots, fruit, seeds or flowers. Exemplary promoters include the anther specific promoter 5126 (U.S. Pat. Nos. 5,689,049 and 5,689,051), glob-1 promoter, and gamma-zein promoter. The operation of a promoter may also vary depending on its location in the genome. Thus, an inducible promoter may become fully or partially constitutive in certain locations.

Both heterologous and non-heterologous (i.e., endogenous) promoters can be employed to direct expression of the nucleic acids of the present invention. These promoters can also be used, for example, in recombinant expression cassettes to drive expression of antisense nucleic acids to reduce, increase, or alter concentration and/or composition of the proteins of the present invention in a desired tissue. Thus, in some embodiments, the nucleic acid construct will comprise a promoter functional in a plant cell, such as in *Zea mays*, operably linked to a polynucleotide of the present invention. Promoters useful in these embodiments include the endogenous promoters driving expression of a polypeptide of the present invention.

A number of promoters can be used in the practice of the invention, including the native promoter of a polynucleotide sequence of interest. The promoters can be selected based on the desired outcome. The nucleic acids can be combined with constitutive, inducible, tissue-preferred or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell, et al., (1985) *Nature* 313:810-812); rice actin (McElroy, et al., (1990) *Plant Cell* 2:163-171); ubiquitin (Christensen, et al., (1989) *Plant Mol. Biol.* 12:619-632 and Christensen, et al., (1992) *Plant Mol. Biol.* 18:675-689); pEMU (Last, et al., (1991) *Theor. Appl. Genet.* 81:581-588); MAS (Velten, et al., (1984) *EMBO J.* 3:2723-2730); ALS promoter (U.S. Pat. No. 5,659,026), dMMV (double-enhanced version of the mirabilis mosaic virus promoter; see, Dey and Maiti (1999) *Plant Molecular Biology* 40(5):771-782), LESVBV (enhanced strawberry vein banding virus promoter; see, US Patent Application Publication Number 2002/0182593) and the like. Other constitutive promoters include, for example, U.S. Pat. Nos. 5,608,149; 5,608,144; 5,604,121; 5,569,597; 5,466,785; 5,399,680; 5,268,463; 5,608,142 and 6,177,611.

Tissue-preferred promoters can be utilized to target enhanced expression within a particular plant tissue. Tissue-preferred promoters include Yamamoto, et al., (1997) *Plant J.* 12(2):255-265; Kawamata, et al., (1997) *Plant Cell Physiol.* 38(7):792-803; Hansen, et al., (1997) *Mol. Gen Genet.* 254 (3):337-343; Russell, et al., (1997) *Transgenic Res.* 6(2):157-168; Rinehart, et al., (1996) *Plant Physiol.* 112(3):1331-1341; Van Camp, et al., (1996) *Plant Physiol.* 112(2):525-535; Canevascini, et al., (1996) *Plant Physiol.* 112(2):513-524; Yamamoto, et al., (1994) *Plant Cell Physiol.* 35(5):773-778; Lam (1994) *Results Probl. Cell Differ.* 20:181-196; Orozco, et al., (1993) *Plant Mol. Biol.* 23(6):1129-1138; Matsuoka, et al., (1993) *Proc Natl. Acad. Sci. USA* 90(20):9586-9590 and Guevara-Garcia, et al., (1993) *Plant J.* 4(3):495-505. Such promoters can be modified, if necessary, for weak expression. See, also, US Patent Application Publication Number 2003/0074698, herein incorporated by reference.

Leaf-preferred promoters are known in the art. See, for example, Yamamoto, et al., (1997) *Plant J.* 12(2):255-265; Kwon, et al., (1994) *Plant Physiol.* 105:357-67; Yamamoto, et al., (1994) *Plant Cell Physiol.* 35(5):773-778; Gotor, et al., (1993) *Plant J.* 3:509-18; Orozco, et al., (1993) *Plant Mol. Biol.* 23(6):1129-1138; Baszczynski, et al., (1988) *Nucl. Acid Res.* 16:4732; Mitra, et al., (1994) *Plant Molecular Biology* 26:35-93; Kayaya, et al., (1995) *Molecular and General Genetics* 248:668-674; and Matsuoka, et al., (1993) *Proc. Natl. Acad. Sci. USA* 90(20):9586-9590. Senecence regulated promoters are also of use, such as, SAM22 (Crowell, et al., (1992) *Plant Mol. Biol.* 18:459-466). See, also, U.S. Pat. No. 5,689,042 herein incorporated by reference.

Root-preferred promoters are known and can be selected from the many available from the literature or isolated de novo from various compatible species. See, for example, Hire, et al., (1992) *Plant Mol. Biol.* 20(2):207-218 (soybean root-specific glutamine synthetase gene); Keller and Baumgartner, (1991) *Plant Cell* 3(10):1051-1061 (root-specific control element in the GRP 1.8 gene of French bean); Sanger, et al., (1990) *Plant Mol. Biol.* 14(3):433-443 (root-specific promoter of the mannopine synthase (MAS) gene of *Agrobacterium tumefaciens*) and Miao, et al., (1991) *Plant Cell* 3(1):11-22 (full-length cDNA clone encoding cytosolic glutamine synthetase (GS), which is expressed in roots and root nodules of soybean). See also, Bogusz, et al., (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi, (1991) describe their analysis of the promoters of the highly expressed roIC and rolD root-inducing genes of *Agrobacterium rhizogenes* (see, *Plant Science* (Limerick) 79(1):69-76). They concluded that enhancer and tissue-preferred DNA determinants are dissociated in those promoters. Teeri, et al., (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see, *EMBO J.* 8(2):343-350). The TR1' gene, fused to nptII (neomycin phosphotransferase II) showed similar characteristics. Additional root-preferred promoters include the VfENOD-GRP3 gene promoter (Kuster, et al., (1995) *Plant Mol. Biol.* 29(4):759-772); roIB promoter (Capana, et al., (1994) *Plant Mol. Biol.* 25(4):681-691; and the CRWAQ81 root-preferred promoter with the ADH first intron (US Patent Application Publication Number 2005/0097633). See also, U.S. Pat. Nos. 5,837,876; 5,750,386; 5,633,363; 5,459,252; 5,401,836; 5,110,732 and 5,023,179.

"Seed-preferred" promoters refers to those promoters active during seed development and may include expression in seed initials or related maternal tissue. Such seed-preferred promoters include, but are not limited to, Cim1 (cytokinin-induced message); cZ19B1 (maize 19 kDa zein); milps (myo-inositol-1-phosphate synthase) (see, WO 00/11177 and U.S. Pat. No. 6,225,529; herein incorporated by reference). Gamma-zein is an endosperm-specific promoter. Globulin-1 (Glob-1) is a representative embryo-specific promoter. For dicots, seed-specific promoters include, but are not limited to, bean β-phaseolin, napin, β-conglycinin, soybean lectin, cruciferin and the like. For monocots, seed-specific promoters include, but are not limited to, maize 15 kDa zein, 22 kDa zein, 27 kDa zein, gamma-zein, waxy, shrunken 1 and shrunken 2. See also, WO 2000/12733, where seed-preferred promoters from end1 and end2 genes are disclosed; herein incorporated by reference. Additional embryo specific promoters are disclosed in Sato, et al., (1996) *Proc. Natl. Acad. Sci.* 93:8117-8122; Nakase, et al., (1997) Plant J 12:235-46; and Postma-Haarsma, et al., (1999) *Plant Mol. Biol.* 39:257-71. Additional endosperm specific promoters are disclosed in Albani, et al., (1984) *EMBO* 3:1405-15; Albani, et al., (1999) *Theor. Appl. Gen.* 98:1253-62; Albani, et al., (1993) *Plant J.* 4:343-55; Mena, et al., (1998) *The Plant Journal* 116:53-62 and Wu, et al., (1998) *Plant Cell Physiology* 39:885-889.

Also of interest are promoters active in meristem regions, such as developing inflorescence tissues, and promoters which drive expression at or about the time of anthesis or early kernel development. This may include, for example, the maize Zag promoters, including Zag1 and Zag2 (see, Schmidt, et al., (1993) *The Plant Cell* 5:729-37; GenBank X80206; Theissen, et al., (1995) *Gene* 156:155-166; and U.S. patent application Ser. No. 10/817,483); maize Zap promoter (also known as ZmMADS; U.S. patent application Ser. No. 10/387,937; WO 03/078590); maize ckx1-2 promoter (US Patent Application Publication Number 2002/0152500 A1; WO 2002/0078438); maize eep1 promoter (U.S. patent application Ser. No. 10/817,483); maize end2 promoter (U.S. Pat. No. 6,528,704 and U.S. patent application Ser. No. 10/310, 191); maize lec1 promoter (U.S. patent application Ser. No. 09/718,754); maize F3.7 promoter (Baszczynski, et al., (1997) *Maydica* 42:189-201); maize tb1 promoter (Hubbarda, et al., (2002) *Genetics* 162:1927-1935 and Wang, et al., (1999) *Nature* 398:236-239); maize eep2 promoter (U.S. patent application Ser. No. 10/817,483); maize thioredoxinH promoter (U.S. Provisional Patent Application Ser. No. 60/514,123); maize Zm40 promoter (U.S. Pat. No. 6,403,862 and WO 2001/2178); maize mLIP15 promoter (U.S. Pat. No. 6,479,734); maize ESR promoter (U.S. patent application Ser. No. 10/786,679); maize PCNA2 promoter (U.S. patent application Ser. No. 10/388,359); maize cytokinin oxidase promoters (U.S. patent application Ser. No. 11/094,917); promoters disclosed in Weigal, et al., (1992) *Cell* 69:843-859; Accession Number AJ131822; Accession Number Z71981; Accession Number AF049870; and shoot-preferred promoters disclosed in McAvoy, et al., (2003) *Acta Hort. (ISHS)* 625:379-385. Other dividing cell or meristematic tissue-preferred promoters that may be of interest have been disclosed in Ito, et al., (1994) *Plant Mol. Biol.* 24:863-878; Regad, et al., (1995) *Mo. Gen. Genet.* 248:703-711; Shaul, et al., (1996) *Proc. Natl. Acad. Sci.* 93:4868-4872; Ito, et al., (1997) *Plant J.* 11:983-992; and Trehin, et al., (1997) *Plant Mol. Biol.* 35:667-672, all of which are hereby incorporated by reference herein.

Inflorescence-preferred promoters include the promoter of chalcone synthase (Van der Meer, et al., (1990) *Plant Mol. Biol.* 15:95-109), LAT52 (Twell, et al., (1989) *Mol. Gen. Genet.* 217:240-245), pollen specific genes (Albani, et al., (1990) *Plant Mol. Biol.* 15:605, Zm13 (Buerrero, et al., (1993) *Mol. Gen. Genet.* 224:161-168), maize pollen-specific gene (Hamilton, et al., (1992) *Plant Mol. Biol.* 18:211-218), sunflower pollen expressed gene (Baltz, et al., (1992) *The Plant Journal* 2:713-721), and *B. napus* pollen specific genes (Arnoldo, et al., (1992) *J. Cell. Biochem*, Abstract Number Y101204).

Stress-inducible promoters include salt-inducible or water-stress-inducible promoters such as P5CS (Zang, et al., (1997) *Plant Sciences* 129:81-89); cold-inducible promoters, such as, cor15a (Hajela, et al., (1990) *Plant Physiol.* 93:1246-1252), cor15b (Wlihelm, et al., (1993) *Plant Mol Biol* 23:1073-1077), wsc120 (Ouellet, et al., (1998) *FEBS Lett.* 423-324-328), ci7 (Kirch, et al., (1997) *Plant Mol. Biol.* 33:897-909), ci21A (Schneider, et al., (1997) *Plant Physiol.* 113:335-45); drought-inducible promoters, such as, Trg-31 (Chaudhary, et al., (1996) *Plant Mol. Biol.* 30:1247-57); osmotic inducible promoters, such as, Rab17 (Vilardell, et al., (1991) *Plant Mol. Biol.* 17:985-93; Busk, (1997) *Plant J* 11(6):1285-1295) and osmotin (Raghothama, et al., (1993) *Plant Mol Biol* 23:1117-28) and, heat inducible promoters, such as, heat shock proteins (Barros, et al., (1992) *Plant Mol.* 19:665-75; Marrs, et al., (1993) *Dev. Genet.* 14:27-41) and smHSP (Waters, et al., (1996) *J. Experimental Botany* 47:325-338). Other stress-inducible promoters include rip2 (U.S. Pat. No. 5,332,808 and US Patent Application Publication Number 2003/0217393), and rd29a (Yamaguchi-Shinozaki, et al., (1993) *Mol. Gen. Genetics* 236:331-340; see also, GenBank accession D13044). Stress-insensitive promoters can also be used in the methods of the invention.

Nitrogen-responsive promoters can also be used in the methods of the invention. Such promoters include, but are not limited to, the 22 kDa Zein promoter (Spena, et al., (1982) *EMBO J.* 1:1589-1594 and Muller, et al., (1995) *J. Plant Physiol* 145:606-613); the 19 kDa zein promoter (Pedersen, et al., (1982) *Cell* 29:1019-1025); the 14 kDa zein promoter (Pedersen, et al., (1986) *J. Biol. Chem.* 261:6279-6284), the b-32 promoter (Lohmer, et al., (1991) *EMBO J* 10:617-624) and the nitrite reductase (NiR) promoter (Rastogi, et al., (1997) *Plant Mol Biol.* 34(3):465-76 and Sander, et al., (1995) *Plant Mol Biol.* 27(1):165-77). For a review of consensus sequences found in nitrogen-induced promoters, see for example, Muller, et al., (1997) *The Plant Journal* 12:281-291.

Chemically-regulated promoters can be used to modulate the expression of a gene in a plant through the application of an exogenous chemical regulator. Depending upon the objective, the promoter may be a chemically-inducible promoter, where application of the chemical induces gene expression, or a chemical-repressible promoter, where application of the chemical represses gene expression. Chemically-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena, et al., (1991) *Proc. Natl. Acad. Sci. USA* 88:10421-10425 and McNellis, et al., (1998) *Plant J.* 14(2):247-257) and tetracycline-inducible and tetracycline-repressible promoters (see, for example, Gatz, et al., (1991) *Mol. Gen. Genet.* 227:229-237, and U.S. Pat. Nos. 5,814,618 and 5,789,156), herein incorporated by reference.

Additional inducible promoters include heat shock promoters, such as Gmhsp17.5-E (soybean) (Czarnecka, et al., (1989) *Mol Cell Biol.* 9(8):3457-3463); APX1 gene promoter (Arabidopsis) (Storozhenko, et al., (1998) *Plant Physiol.* 118 (3):1005-1014): Ha hsp17.7 G4 (*Helianthus annuus*) (Almoguera, et al., (2002) *Plant Physiol.* 129(1):333-341 and Maize Hsp70 (Rochester, et al., (1986) *EMBO J.* 5: 451-8).

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see, Kmiec, U.S. Pat. No. 5,565,350; Zarling, et al., PCT/US93/03868) or isolated promoters can be introduced into a plant cell in the proper orientation and distance from a gene of the present invention so as to control the expression of the gene. Gene expression can be modulated under conditions suitable for plant growth so as to alter the total concentration and/or alter the composition of the polypeptides of the present invention in plant cell.

Thus, the present invention provides compositions, and methods for making, heterologous promoters and/or enhancers operably linked to a native, endogenous (i.e., nonheterologous) form of a polynucleotide of the present invention.

Methods for identifying promoters with a particular expression pattern, in terms of, e.g., tissue type, cell type, stage of development and/or environmental conditions, are well known in the art. See, e.g., The Maize Handbook, Chapters 114-115, Freeling and Walbot, Eds., Springer, N.Y. (1994); Corn and Corn Improvement, 3rd edition, Chapter 6, Sprague and Dudley, Eds., American Society of Agronomy, Madison, Wis. (1988).

A typical step in promoter isolation methods is identification of gene products that are expressed with some degree of specificity in the target tissue. Amongst the range of methodologies are: differential hybridization to cDNA libraries; subtractive hybridization; differential display; differential 2-D protein gel electrophoresis; DNA probe arrays and isolation of proteins known to be expressed with some specificity in the target tissue. Such methods are well known to those of skill in the art. Commercially available products for identifying promoters are known in the art such as Clontech's (Palo Alto, Calif.) Universal Genome Walker Kit.

For the protein-based methods, it is helpful to obtain the amino acid sequence for at least a portion of the identified protein, and then to use the protein sequence as the basis for preparing a nucleic acid that can be used as a probe to identify either genomic DNA directly, or preferably, to identify a cDNA clone from a library prepared from the target tissue. Once such a cDNA clone has been identified, that sequence can be used to identify the sequence at the 5' end of the transcript of the indicated gene. For differential hybridization, subtractive hybridization and differential display, the nucleic acid sequence identified as enriched in the target tissue is used to identify the sequence at the 5' end of the transcript of the indicated gene. Once such sequences are identified, starting either from protein sequences or nucleic acid sequences, any of these sequences identified as being from the gene transcript can be used to screen a genomic library prepared from the target organism. Methods for identifying and confirming the transcriptional start site are well known in the art.

In the process of isolating promoters expressed under particular environmental conditions or stresses, or in specific tissues, or at particular developmental stages, a number of genes are identified that are expressed under the desired circumstances, in the desired tissue or at the desired stage. Further analysis will reveal expression of each particular gene in one or more other tissues of the plant. One can identify a promoter with activity in the desired tissue or condition but that does not have activity in any other common tissue.

To identify the promoter sequence, the 5' portions of the clones described here are analyzed for sequences characteristic of promoter sequences. For instance, promoter sequence elements include the TATA box consensus sequence (TATAAT), which is usually an AT-rich stretch of 5-10 bp located approximately 20 to 40 base pairs upstream of the transcription start site. Identification of the TATA box is well known in the art. For example, one way to predict the location of this element is to identify the transcription start site using standard RNA-mapping techniques such as primer extension, S 1 analysis, and/or RNase protection. To confirm the presence of the AT-rich sequence, a structure-function analysis can be performed involving mutagenesis of the putative region and quantification of the mutation's effect on expression of a linked downstream reporter gene. See, e.g., The Maize Handbook, Chapter 114, Freeling and Walbot, Eds., Springer, N.Y., (1994).

In plants, further upstream from the TATA box, at positions −80 to −100, there is typically a promoter element (i.e., the CAAT box) with a series of adenines surrounding the trinucleotide G (or T) N G. Messing, et al., in Genetic Engineering in Plants, Kosage, Meredith and Hollaender, Eds., pp. 221-227 1983. In maize, there is no well conserved CAAT box but there are several short, conserved protein-binding motifs upstream of the TATA box. These include motifs for the trans-acting transcription factors involved in light regulation, anaerobic induction, hormonal regulation or anthocyanin biosynthesis, as appropriate for each gene.

Once promoter and/or gene sequences are known, a region of suitable size is selected from the genomic DNA that is 5' to the transcriptional start, or the translational start site, and such sequences are then linked to a coding sequence. If the transcriptional start site is used as the point of fusion, any of a number of possible 5' untranslated regions can be used in between the transcriptional start site and the partial coding sequence. If the translational start site at the 3' end of the specific promoter is used, then it is linked directly to the methionine start codon of a coding sequence.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes or alternatively from another plant gene or less preferably from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, (1988) *Mol. Cell Biol.* 8: 4395-4405; Callis, et al., (1987) *Genes Dev.* 1:1183-1200. Such intron enhancement of gene expression is typically greatest when placed near the 5' end of the transcription unit. Use of maize introns Adhl-S intron 1, 2 and 6, the Bronze-1 intron are known in the art. See generally, The Maize Handbook, Chapter 116, Freeling and Walbot, Eds., Springer, N.Y. (1994).

The vector comprising the sequences from a polynucleotide of the present invention will typically comprise a marker gene which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or genetic in resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, the nptII gene encodes resistance to the antibiotic kanamycin, and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers, et al., (1987) *Meth. in Enzymol.* 153:253-277. These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl, et al., (1987) Gene 61:1-11 and Berger, et al., (1989) *Proc. Natl. Acad. Sci. USA* 86:8402-8406. Another useful vector herein is plasmid pBI101.2 that is available from Clontech Laboratories, Inc. (Palo Alto, Calif.).

A polynucleotide of the present invention can be expressed in either sense or antisense orientation as desired. It will be appreciated that control of gene expression in either sense or anti-sense orientation can have a direct impact on the observable plant characteristics. Antisense technology can be conveniently used to inhibit gene expression in plants. To accomplish this, a nucleic acid segment from the desired gene is cloned and operably linked to a promoter such that the anti-sense strand of RNA will be transcribed. The construct is then transformed into plants and the antisense strand of RNA is produced.

In plant cells, it has been shown that antisense RNA inhibits gene expression by preventing the accumulation of mRNA which encodes the enzyme of interest, see, e.g., Sheehy, et al., (1988) *Proc. Nat'l. Acad. Sci. USA* 85:8805-8809; and Hiatt, et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes, see, Napoli, et al., (1990) *The Plant Cell* 2:279-289 and U.S. Pat. No. 5,034,323.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA cleaving activity upon them, thereby increasing the activity of the constructs. The design and use of target RNA-specific ribozymes is described in Haseloff, et al., (1988) *Nature* 334:585 591. A variety of cross-linking agents, alkylating agents and radical generating species as pendant groups on polynucleotides of the present invention can be used to bind, label, detect and/or cleave nucleic acids. For example, Vlassov, et al., (1986) *Nucleic Acids Res* 14:4065-4076, describe covalent bonding of a single-stranded DNA fragment with alkylating derivatives of nucleotides complementary to target sequences. A report of similar work by the same group is that by Knorre, et al., (1985) *Biochimie* 67:785-789. Iverson and Dervan.

The present invention further provides a protein comprising a polypeptide having a specified sequence identity with a polypeptide of the present invention. The percentage of sequence identity is an integer selected from the group consisting of from 60 to 99. Exemplary sequence identity values include 60%, 65%, 70%, 75%, 80%, 85%, 90% and 95%.

As those of skill will appreciate, the present invention includes catalytically active polypeptides of the present invention (i.e., enzymes). Catalytically active polypeptides have a specific activity of at least 20%, 30% or 40% and preferably at least 50%, 60% or 70% and most preferably at least 80%, 90% or 95% that of the native (non-synthetic), endogenous polypeptide. Further, the substrate specificity (kcat/Km) is optionally substantially similar to the native (non-synthetic), endogenous polypeptide. Typically, the Km will be at least 30%, 40% or 50%, that of the native (non-synthetic), endogenous polypeptide and more preferably at least 60%, 70%, 80% or 90%. Methods of assaying and quantifying measures of enzymatic activity and substrate specificity (heat/Km) are well known to those of skill in the art.

Generally, the proteins of the present invention will, when presented as an immunogen, elicit production of an antibody specifically reactive to a polypeptide of the present invention. Further, the proteins of the present invention will not bind to antisera raised against a polypeptide of the present invention which has been fully immunosorbed with the same polypeptide. Immunoassays for determining binding are well known to those of skill in the art. A preferred immunoassay is a competitive immunoassay as discussed, infra. Thus, the proteins of the present invention can be employed as immunogens for constructing antibodies immunoreactive to a protein of the present invention for such exemplary utilities as immunoassays or protein purification techniques.

Expression of Proteins in Host Cells

Using the nucleic acids of the present invention, one may express a protein of the present invention in a recombinantly engineered cell such as bacteria, yeast, insect, mammalian or preferably plant cells. The cells produce the protein in a non-natural condition (e.g., in quantity, composition, location and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or regulatable), followed by incorporation into an expression vector. The vectors can be suitable for replication and integration in either prokaryotes or eukaryotes. Typical expression vectors contain transcription and translation terminators, initiation sequences and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation and a transcription/translation terminator. One of skill would recognize that modifications can be made to a protein of the present invention without diminishing its biological activity. Some modifications may be made to facilitate the cloning, expression or incorporation of the targeting molecule into a fusion protein. Such modifications are well known to those of skill in the art and include, for example, a methionine added at the amino terminus to provide an initiation site or additional amino acids (e.g., poly H is) placed on either terminus to create conveniently located purification sequences. Restriction sites or termination codons can also be introduced.

A. Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang, et al., (1977) *Nature* 198:1056), the tryptophan (trp) promoter system (Goeddel, et al., (1980) *Nucleic Acids Res.* 8:4057) and the lambda derived P L promoter and N-gene ribosome binding site (Shimatake, et al., (1981) *Nature* 292:128). The inclusion of selection markers in DNA vectors transfected in *E. coli* is also useful. Examples of such markers include genes specifying resistance to ampicillin, tetracycline or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva, et al., (1983) *Gene* 22:229-235; Mosbach, et al., (1983) *Nature* 302:543-545).

B. Expression in Eukaryotes

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, et al., Methods in Yeast Genetics, Cold Spring Harbor Laboratory (1982) is a well recognized work describing the various methods available to produce the protein in yeast. Two widely utilized yeast for production of eukaryotic proteins are *Saccharomyces cerevisiae* and *Pichia pastoris*. Vectors, strains and protocols for expression in *Saccharomyces* and *Pichia* are known in the art and available from commercial suppliers (e.g., Invitrogen).

Suitable vectors usually have expression control sequences, such as promoters, including 3-phosphoglycerate kinase or alcohol oxidase and an origin of replication, termination sequences and the like as desired.

A protein of the present invention, once expressed, can be isolated from yeast by lysing the cells and applying standard protein isolation techniques to the lysate. The monitoring of the purification process can be accomplished by using Western blot techniques or radioimmunoassay or other standard immunoassay techniques.

The sequences encoding proteins of the present invention can also be ligated to various expression vectors for use in transfecting cell cultures of, for instance, mammalian, insect or plant origin. Illustrative of cell cultures useful for the production of the peptides are mammalian cells. Mammalian cell systems often will be in the form of monolayers of cells although mammalian cell suspensions may also be used. A number of suitable host cell lines capable of expressing intact proteins have been developed in the art, and include the HEK293, BHK21 and CHO cell lines. Expression vectors for these cells can include expression control sequences, such as an origin of replication, a promoter (e.g., the CMV promoter, a HSVtk promoter or pgk (phosphoglycerate kinase) promoter), an enhancer (Queen, et al., (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, army worm, moth and *Drosophila* cell lines such as a Schneider cell line (see, Schneider, (1987) *J. Embryol. Exp. Morphol.* 27:353-365).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague, et al., (1983) *J. Virol.* 45:773-781). Additionally, gene sequences to control replication in the host cell may be incorporated into the vector such as those found in bovine papilloma virus type-vectors. Saveria-Campo, Bovine Papilloma Virus DNA a Eukaryotic Cloning Vector in DNA Cloning Vol. II a Practical Approach, Glover, Ed., IRL Press, Arlington, Va. pp. 213-238 (1985).

Increasing the Activity and/or Level of an Ethylene Signaling Associated Polypeptide Methods are provided to increase the activity and/or level of the ethylene signaling associated polypeptide of the invention. An increase in the level and/or activity of the ethylene signaling associated polypeptide of the invention can be achieved by providing to the plant an ethylene signaling associated polypeptide. The ethylene signaling associated polypeptide can be provided by introducing the amino acid sequence encoding the ethylene signaling associated polypeptide into the plant, introducing into the plant a nucleotide sequence encoding an ethylene signaling associated polypeptide or alternatively by modifying a genomic locus encoding the ethylene signaling associated polypeptide of the invention.

As discussed elsewhere herein, many methods are known the art for providing a polypeptide to a plant including, but not limited to, direct introduction of the polypeptide into the plant, introducing into the plant (transiently or stably) a polynucleotide construct encoding a polypeptide having enhanced activity. It is also recognized that the methods of the invention may employ a polynucleotide that is not capable of directing, in the transformed plant, the expression of a protein or an RNA. Thus, the level and/or activity of an ethylene signaling associated polypeptide may be increased by altering the gene encoding the ethylene signaling associated polypeptide or its promoter. See, e.g., Kmiec, U.S. Pat. No. 5,565,350; Zarling, et al., PCT/US93/03868. Therefore mutagenized plants that carry mutations in ethylene signaling associated genes, where the mutations increase expression of the ethylene signaling associated gene or increase the ethylene signaling associated activity of the encoded ethylene signaling associated polypeptide are provided.

Reducing the Activity and/or Level of an Ethylene Signaling Associated Polypeptide Methods are provided to reduce or eliminate the activity of an ethylene signaling associated polypeptide of the invention by transforming a plant cell with an expression cassette that expresses a polynucleotide that inhibits the expression of the ethylene signaling associated polypeptide. The polynucleotide may inhibit the expression of the ethylene signaling associated polypeptide directly, by preventing transcription or translation of the ethylene signaling associated messenger RNA, or indirectly, by encoding a polypeptide that inhibits the transcription or translation of an ethylene signaling associated gene encoding ethylene signaling associated polypeptide. Methods for inhibiting or eliminating the expression of a gene in a plant are well known in the art, and any such method may be used in the present invention to inhibit the expression of ethylene signaling associated polypeptide.

In accordance with the present invention, the expression of an ethylene signaling associated polypeptide is inhibited if the protein level of the ethylene signaling associated polypeptide is less than 70% of the protein level of the same ethylene signaling associated polypeptide in a plant that has not been genetically modified or mutagenized to inhibit the expression of that ethylene signaling associated polypeptide. In particular embodiments of the invention, the protein level of the ethylene signaling associated polypeptide in a modified plant according to the invention is less than 60%, less than 50%, less than 40%, less than 30%, less than 20%, less than 10%, less than 5% or less than 2% of the protein level of the same ethylene signaling associated polypeptide in a plant that is not a mutant or that has not been genetically modified to inhibit the expression of that ethylene signaling associated polypeptide. The expression level of the ethylene signaling associated polypeptide may be measured directly, for example, by assaying for the level of ethylene signaling associated polypeptide expressed in the plant cell or plant, or indirectly, for example, by measuring the ethylene response in the plant cell or plant, or by measuring the phenotypic changes in the plant. Methods for performing such assays are described elsewhere herein.

In other embodiments of the invention, the activity of the ethylene signaling associated polypeptide is reduced or eliminated by transforming a plant cell with an expression cassette comprising a polynucleotide encoding a polypeptide that inhibits the activity of an ethylene signaling associated polypeptide. The activity of an ethylene signaling associated polypeptide is inhibited according to the present invention if the activity of the ethylene signaling associated polypeptide is less than 70% of the activity of the same ethylene signaling associated polypeptide in a plant that has not been modified to inhibit the ethylene signaling associated activity of that polypeptide. In particular embodiments of the invention, the ethylene signaling associated activity of the ethylene signaling associated polypeptide in a modified plant according to the invention is less than 60%, less than 50%, less than 40%, less than 30%, less than 20%, less than 10% or less than 5% of the ethylene signaling associated activity of the same polypeptide in a plant that that has not been modified to inhibit the expression of that ethylene signaling associated polypeptide. The ethylene signaling associated activity of an ethylene signaling associated polypeptide is "eliminated" according to the invention when it is not detectable by the assay methods described elsewhere herein. Methods of determining the alteration of activity of an ethylene signaling associated polypeptide are described elsewhere herein.

In other embodiments, the activity of an ethylene signaling associated polypeptide may be reduced or eliminated by disrupting the gene encoding the ethylene signaling associated polypeptide. The invention encompasses mutagenized plants that carry mutations in ethylene signaling associated genes, where the mutations reduce expression of the ethylene signaling associated gene or inhibit the activity of the encoded ethylene signaling associated polypeptide.

Thus, many methods may be used to reduce or eliminate the activity of an ethylene signaling associated polypeptide. In addition, more than one method may be used to reduce the activity of a single ethylene signaling associated polypeptide.

1. Polynucleotide-Based Methods:

In some embodiments of the present invention, a plant is transformed with an expression cassette that is capable of expressing a polynucleotide that inhibits the expression of an ethylene signaling associated polypeptide of the invention. The term "expression" as used herein refers to the biosynthesis of a gene product, including the transcription and/or translation of said gene product. For example, for the purposes of the present invention, an expression cassette capable of expressing a polynucleotide that inhibits the expression of at least one ethylene signaling associated polypeptide is an expression cassette capable of producing an RNA molecule that inhibits the transcription and/or translation of at least one ethylene signaling associated polypeptide of the invention. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of an ethylene signaling associated polypeptide are given below.

i. Sense Suppression/Cosuppression

In some embodiments of the invention, inhibition of the expression of an ethylene signaling associated polypeptide may be obtained by sense suppression or cosuppression. For cosuppression, an expression cassette is designed to express an RNA molecule corresponding to all or part of a messenger RNA encoding an ethylene signaling associated polypeptide in the "sense" orientation. Over expression of the RNA molecule can result in reduced expression of the native gene.

Accordingly, multiple plant lines transformed with the cosuppression expression cassette are screened to identify those that show the greatest inhibition of ethylene signaling associated polypeptide expression.

The polynucleotide used for cosuppression may correspond to all or part of the sequence encoding the ethylene signaling associated polypeptide, all or part of the 5' and/or 3' untranslated region of an ethylene signaling associated polypeptide transcript, or all or part of both the coding sequence and the untranslated regions of a transcript encoding an ethylene signaling associated polypeptide. In some embodiments where the polynucleotide comprises all or part of the coding region for the ethylene signaling associated polypeptide, the expression cassette is designed to eliminate the start codon of the polynucleotide so that no protein product will be translated.

Cosuppression may be used to inhibit the expression of plant genes to produce plants having undetectable protein levels for the proteins encoded by these genes. See, for example, Broin, et al., (2002) *Plant Cell* 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell, et al., (1994) *Proc. Natl. Acad. Sci. USA* 91:3490-3496; Jorgensen, et al., (1996) *Plant Mol. Biol.* 31:957-973; Johansen and Carrington, (2001) *Plant Physiol.* 126:930-938; Broin, et al., (2002) *Plant Cell* 14:1417-1432; Stoutjesdijk, et al., (2002) *Plant Physiol.* 129:1723-1731; Yu, et al., (2003) *Phytochemistry* 63:753-763; and U.S. Pat. Nos. 5,034,323, 5,283,184 and 5,942,657, each of which is herein incorporated by reference. The efficiency of cosuppression may be increased by including a poly-dT region in the expression cassette at a position 3' to the sense sequence and 5' of the polyadenylation signal. See, US Patent Application Publication Number 2002/0048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034,323, herein incorporated by reference.

ii. Antisense Suppression

In some embodiments of the invention, inhibition of the expression of the ethylene signaling associated polypeptide may be obtained by antisense suppression. For antisense suppression, the expression cassette is designed to express an RNA molecule complementary to all or part of a messenger RNA encoding the ethylene signaling associated polypeptide. Over expression of the antisense RNA molecule can result in reduced expression of the native gene. Accordingly, multiple plant lines transformed with the antisense suppression expression cassette are screened to identify those that show the greatest inhibition of ethylene signaling associated polypeptide expression.

The polynucleotide for use in antisense suppression may correspond to all or part of the complement of the sequence encoding the ethylene signaling associated polypeptide, all or part of the complement of the 5' and/or 3' untranslated region of the ethylene signaling associated transcript, or all or part of the complement of both the coding sequence and the untranslated regions of a transcript encoding the ethylene signaling associated polypeptide. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550 or greater may be used. Methods for using antisense suppression to inhibit the expression of endogenous genes in plants are described, for example, in Liu, et al., (2002) *Plant Physiol.* 129:1732-1743 and U.S. Pat. Nos. 5,759,829 and 5,942,657 each of which is herein incorporated by reference. Efficiency of antisense suppression may be increased by including a poly-dT region in the expression cassette at a position 3' to the antisense sequence and 5' of the polyadenylation signal. See, US Patent Application Publication Number 2002/0048814, herein incorporated by reference.

iii. Double-Stranded RNA Interference

In some embodiments of the invention, inhibition of the expression of an ethylene signaling associated polypeptide may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of ethylene signaling associated polypeptide expression. Methods for using dsRNA interference to inhibit the expression of endogenous plant genes are described in Waterhouse, et al., (1998) *Proc. Natl. Acad. Sci. USA* 95:13959-13964, Liu, et al., (2002) *Plant Physiol.* 129:1732-1743, and WO 1999/49029, WO 1999/53050, WO 1999/61631 and WO 2000/49035, each of which is herein incorporated by reference.

iv. Hairpin RNA Interference and Intron-Containing Hairpin RNA Interference

In some embodiments of the invention, inhibition of the expression of an ethylene signaling associated polypeptide may be obtained by hairpin RNA (hpRNA) interference or intron-containing hairpin RNA (ihpRNA) interference. These methods are highly efficient at inhibiting the expression of endogenous genes. See, Waterhouse and Helliwell, (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Alternatively, the base-paired stem region may correspond to a portion of a promoter sequence controlling expression of the gene to be inhibited. Thus, the base-paired stem region of the molecule generally determines the specificity of the RNA interference. hpRNA molecules are highly efficient at inhibiting the expression of endogenous genes, and the RNA interference they induce is inherited by subsequent generations of plants. See, for example, Chuang and Meyerowitz, (2000) *Proc. Natl. Acad. Sci. USA* 97:4985-4990; Stoutjesdijk, et al., (2002) *Plant Physiol.* 129:1723-1731 and Waterhouse and Helliwell, (2003) *Nat. Rev. Genet.* 4:29-38. Methods for using hpRNA interference to inhibit or silence the expression of genes are described, for example, in Chuang and Meyerowitz, (2000) *Proc. Natl. Acad. Sci. USA* 97:4985-4990; Stoutjesdijk, et al., (2002) *Plant Physiol.* 129: 1723-1731; Waterhouse and Helliwell, (2003) *Nat. Rev. Genet.* 4:29-38; Pandolfini et al., *BMC Biotechnology* 3:7 and US Patent Application Publication Number 2003/0175965, each of which is herein incorporated by reference. A transient assay for the efficiency of hpRNA constructs to silence gene expression in vivo has been described by Panstruga, et al., (2003) *Mol. Biol. Rep.* 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith, et al., (2000) *Nature* 407: 319-320. In fact, Smith, et al., show 100% suppression of endogenous gene expression using ihpRNA-mediated interference. Methods for using ihpRNA interference to inhibit the expression of endogenous plant genes are described, for example, in Smith, et al., (2000) *Nature* 407:319-320; Wesley, et al., (2001) *Plant J.* 27:581-590; Wang and Waterhouse, (2001) *Curr. Opin. Plant Biol.* 5:146-150; Waterhouse and Helliwell, (2003) *Nat. Rev. Genet.* 4:29-38; Helliwell and Waterhouse, (2003) *Methods* 30:289-295 and US Patent Application Publication Number 2003/0180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 2002/00904; Mette, et al., (2000) *EMBO J* 19:5194-5201; Matzke, et al., (2001) *Curr. Opin. Genet. Devel.* 11:221-227; Scheid, et al., (2002) *Proc. Natl. Acad. Sci., USA* 99:13659-13662; Aufsaftz, et al., (2002) *Proc. Nat'l. Acad. Sci.* 99(4): 16499-16506; Sijen, et al., *Curr. Biol.* (2001) 11:436-440), herein incorporated by reference.

v. Amplicon-Mediated Interference

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for the ethylene signaling associated polypeptide). Methods of using amplicons to inhibit the expression of endogenous plant genes are described, for example, in Angell and Baulcombe, (1997) *EMBO J.* 16:3675-3684, Angell and Baulcombe, (1999) *Plant J.* 20:357-362 and U.S. Pat. No. 6,646,805, each of which is herein incorporated by reference.

vi. Ribozymes

In some embodiments, the polynucleotide expressed by the expression cassette of the invention is catalytic RNA or has ribozyme activity specific for the messenger RNA of the ethylene signaling associated polypeptide. Thus, the polynucleotide causes the degradation of the endogenous messenger RNA, resulting in reduced expression of the ethylene signaling associated polypeptide. This method is described, for example, in U.S. Pat. No. 4,987,071, herein incorporated by reference.

vii. Small Interfering RNA or Micro RNA

In some embodiments of the invention, inhibition of the expression of an ethylene signaling associated polypeptide may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example Javier, et al., (2003) *Nature* 425:257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of ethylene signaling associated expression, the 22-nucleotide sequence is selected from an ethylene signaling associated transcript sequence and contains 22 nucleotides of said ethylene signaling associated sequence in sense orientation and 21 nucleotides of a corresponding antisense sequence that is complementary to the sense sequence. miRNA molecules are highly efficient at inhibiting the expression of endogenous genes, and the RNA interference they induce is inherited by subsequent generations of plants.

2. Polypeptide-Based Inhibition of Gene Expression

In one embodiment, the polynucleotide encodes a zinc finger protein that binds to a gene encoding an ethylene signaling associated polypeptide, resulting in reduced expression of the gene. In particular embodiments, the zinc finger protein binds to a regulatory region of an ethylene signaling associated gene. In other embodiments, the zinc finger protein binds to a messenger RNA encoding an ethylene signaling associated polypeptide and prevents its translation. Methods of selecting sites for targeting by zinc finger proteins have been described, for example, in U.S. Pat. No. 6,453,242, and methods for using zinc finger proteins to inhibit the expression of genes in plants are described, for example, in US Patent Application Publication Number 2003/0037355, each of which is herein incorporated by reference.

3. Polypeptide-Based Inhibition of Protein Activity

In some embodiments of the invention, the polynucleotide encodes an antibody that binds to at least one ethylene signaling associated polypeptide, and reduces the enhanced activity of the ethylene signaling associated polypeptide. In another embodiment, the binding of the antibody results in increased turnover of the antibody-ethylene signaling associated complex by cellular quality control mechanisms. The expression of antibodies in plant cells and the inhibition of molecular pathways by expression and binding of antibodies to proteins in plant cells are well known in the art. See, for example, Conrad and Sonnewald, (2003) *Nature Biotech.* 21:35-36, incorporated herein by reference.

4. Gene Disruption

In some embodiments of the present invention, the activity of an ethylene signaling associated polypeptide is reduced or eliminated by disrupting the gene encoding the ethylene signaling associated polypeptide. The gene encoding the ethylene signaling associated polypeptide may be disrupted by any method known in the art. For example, in one embodiment, the gene is disrupted by transposon tagging. In another embodiment, the gene is disrupted by mutagenizing plants using random or targeted mutagenesis, and selecting for plants that have reduced activity.

i. Transposon Tagging

In one embodiment of the invention, transposon tagging is used to reduce or eliminate the ethylene signaling activity of one or more ethylene signaling associated polypeptide. Transposon tagging comprises inserting a transposon within an endogenous ethylene signaling associated gene to reduce or eliminate expression of the ethylene signaling associated polypeptide.

In this embodiment, the expression of one or more ethylene signaling associated polypeptide is reduced or eliminated by inserting a transposon within a regulatory region or coding region of the gene encoding the ethylene signaling associated polypeptide. A transposon that is within an exon, intron, 5' or 3' untranslated sequence, a promoter, or any other regulatory sequence of an ethylene signaling associated gene may be used to reduce or eliminate the expression and/or activity of the encoded ethylene signaling associated polypeptide.

Methods for the transposon tagging of specific genes in plants are well known in the art. See, for example, Maes, et al., (1999) *Trends Plant Sci.* 4:90-96; Dharmapuri and Sonti, (1999) *FEMS Microbiol. Lett.* 179:53-59; Meissner, et al., (2000) *Plant J.* 22:265-274; Phogat, et al., (2000) *J. Biosci.* 25:57-63; Walbot, (2000) *Curr. Opin. Plant Biol.* 2:103-107; Gai, et al., (2000) *Nucleic Acids Res.* 28:94-96; Fitzmaurice, et al., (1999) *Genetics* 153:1919-1928). In addition, the TUSC process for selecting Mu insertions in selected genes has been described in Bensen, et al., (1995) *Plant Cell* 7:75-84; Mena, et al., (1996) *Science* 274:1537-1540 and U.S. Pat. No. 5,962,764, each of which is herein incorporated by reference.

ii. Mutant Plants with Reduced Activity

Additional methods for decreasing or eliminating the expression of endogenous genes in plants are also known in the art and can be similarly applied to the instant invention. These methods include other forms of mutagenesis, such as ethyl methanesulfonate-induced mutagenesis, deletion mutagenesis, and fast neutron deletion mutagenesis used in a reverse genetics sense (with PCR) to identify plant lines in which the endogenous gene has been deleted. For examples of these methods see, Ohshima, et al., (1998) *Virology* 243: 472-481; Okubara, et al., (1994) *Genetics* 137:867-874 and Quesada, et al., (2000) *Genetics* 154:421-436, each of which is herein incorporated by reference. In addition, a fast and automatable method for screening for chemically induced mutations, TILLING (Targeting Induced Local Lesions In Genomes), using denaturing HPLC or selective endonuclease digestion of selected PCR products is also applicable to the instant invention. See, McCallum, et al., (2000) *Nat. Biotechnol.* 18:455-457, herein incorporated by reference.

Mutations that impact gene expression or that interfere with the function (enhanced activity) of the encoded protein are well known in the art. Insertional mutations in gene exons usually result in null-mutants. Mutations in conserved residues are particularly effective in inhibiting the activity of the encoded protein. Conserved residues of plant ethylene signaling associated polypeptides suitable for mutagenesis with the goal to eliminate ethylene signaling associated activity have been described. Such mutants can be isolated according to well-known procedures, and mutations in different ethylene signaling associated loci can be stacked by genetic crossing. See, for example, Gruis, et al., (2002) *Plant Cell* 14:2863-2882.

In another embodiment of this invention, dominant mutants can be used to trigger RNA silencing due to gene inversion and recombination of a duplicated gene locus. See, for example, Kusaba, et al., (2003) *Plant Cell* 15:1455-1467.

The invention encompasses additional methods for reducing or eliminating the activity of one or more ethylene signaling associated polypeptide. Examples of other methods for altering or mutating a genomic nucleotide sequence in a plant are known in the art and include, but are not limited to, the use of RNA:DNA vectors, RNA:DNA mutational vectors, RNA:DNA repair vectors, mixed-duplex oligonucleotides, self-complementary RNA:DNA oligonucleotides and recombinogenic oligonucleobases. Such vectors and methods of use are known in the art. See, for example, U.S. Pat. Nos. 5,565,350; 5,731,181; 5,756,325; 5,760,012; 5,795,972 and 5,871,984, each of which are herein incorporated by reference. See also, WO 1998/49350, WO 1999/07865, WO 1999/25821 and Beetham, et al., (1999) *Proc. Natl. Acad. Sci. USA* 96:8774-8778, each of which is herein incorporated by reference.

Transfection/Transformation of Cells

The method of transformation/transfection is not critical to the instant invention; various methods of transformation or transfection are currently available. As newer methods are available to transform crops or other host cells they may be directly applied.

Accordingly, a wide variety of methods have been developed to insert a DNA sequence into the genome of a host cell to obtain the transcription and/or translation of the sequence to effect phenotypic changes in the organism. Thus, any method which provides for effective transformation/transfection may be employed.

A. Plant Transformation

A DNA sequence coding for the desired polypeptide of the present invention, for example a cDNA or a genomic sequence encoding a full length protein, will be used to construct a recombinant expression cassette which can be introduced into the desired plant.

Isolated nucleic acid acids of the present invention can be introduced into plants according to techniques known in the art. Generally, recombinant expression cassettes as described above and suitable for transformation of plant cells are prepared. Techniques for transforming a wide variety of higher plant species are well known and described in the technical, scientific, and patent literature. See, for example, Weising, et al., (1988) *Ann. Rev. Genet.* 22:421-477. For example, the DNA construct may be introduced directly into the genomic DNA of the plant cell using techniques such as electroporation, polyethylene glycol (PEG), poration, particle bombardment, silicon fiber delivery, or microinjection of plant cell protoplasts or embryogenic callus. See, e.g., Tomes, et al., Direct DNA Transfer into Intact Plant Cells Via Microprojectile Bombardment. pp. 197213 in Plant Cell, Tissue and Organ Culture, Fundamental Methods. eds. Gamborg and Phillips, Springer-Verlag Berlin Heidelberg New York, 1995. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616.

The introduction of DNA constructs using PEG precipitation is described in Paszkowski, et al., (1984) *Embo J.* 3:2717-2722. Electroporation techniques are described in Fromm, et al., (1985) *Proc. Natl. Acad. Sci.* (USA) 82:5824. Ballistic transformation techniques are described in Klein, et al., (1987) *Nature* 327:70-73.

*Agrobacterium tumefaciens*-mediated transformation techniques are well described in the scientific literature. See, for example Horsch, et al., (1984) *Science* 233:496-498, and Fraley, et al., (1983) *Proc. Natl. Acad. Sci.* (USA) 80:4803. Although *Agrobacterium* is useful primarily in dicots, certain monocots can be transformed by *Agrobacterium*. For instance, *Agrobacterium* transformation of maize is described in U.S. Pat. No. 5,550,318.

Other methods of transfection or transformation include (1) *Agrobacterium rhizogenes*-mediated transformation (see, e.g., Lichtenstein and Fuller In: Genetic Engineering, vol. 6, Rigby, Ed., London, Academic Press, 1987 and Lichtenstein and Draper, In: DNA Cloning, Vol. II, Glover, Ed., Oxford, IRI Press, 1985), Application PCT/US87/02512 (WO 1988/02405 published Apr. 7, 1988) describes the use of *A. rhizogenes* strain A4 and its Ri plasmid along with *A. tumefaciens* vectors pARC8 orpARC16; (2) liposome-mediated DNA uptake (see, e.g., Freeman, et al., (1984) *Plant Cell Physiol.* 25:1353); (3) the vortexing method (see, e.g., Kindle, (1990) *Proc. Natl. Acad. Sci.* (USA) 87:1228).

DNA can also be introduced into plants by direct DNA transfer into pollen as described by Zhou, et al., (1983) *Methods in Enzymology* 101:433; Hess, (1987) *Intern Rev. Cytol.* 107:367; Luo, et al., (1988) *Plant Mol. Biol. Reporter* 6:165. Expression of polypeptide coding genes can be obtained by injection of the DNA into reproductive organs of a plant as described by Pena, et al., (1987) *Nature* 325:274.

DNA can also be injected directly into the cells of immature embryos and the rehydration of desiccated embryos as described by Neuhaus, et al., (1987) *Theor. Appl. Genet.* 75:30 and Benbrook, et al., (1986) in Proceedings Bio Expo 1986, Butterworth, Stoneham, Mass., pp. 27-54. A variety of plant viruses that can be employed as vectors are known in the art and include cauliflower mosaic virus (CaMV), geminivirus, brome mosaic virus and tobacco mosaic virus.

B. Transfection of Prokaryotes, Lower Eukaryotes, and Animal Cells

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics and micro-injection of the DNA directly into the cells. The transfected cells are cultured by means well known in the art. Kuchler, Biochemical Methods in Cell Culture and Virology, Dowden, Hutchinson and Ross, Inc. (1977).

Synthesis of Proteins

The proteins of the present invention can be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3-284 in The Peptides: Analysis, Synthesis, Biology Vol. 2: Special Methods in Peptide Synthesis, Part A.; Merrifield, et al., (1963) *J. Am. Chem. Soc.* 85:2149-2156 and Stewart, et al., Solid Phase Peptide Synthesis, 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide) are known to those of skill.

Purification of Proteins

The proteins of the present invention may be purified by standard techniques well known to those of skill in the art. Recombinantly produced proteins of the present invention can be directly expressed or expressed as a fusion protein. The recombinant protein is purified by a combination of cell lysis (e.g., sonication, French press) and affinity chromatography. For fusion products, subsequent digestion of the fusion protein with an appropriate proteolytic enzyme releases the desired recombinant protein.

The proteins of this invention, recombinant or synthetic, may be purified to substantial purity by standard techniques well known in the art, including detergent solubilization, selective precipitation with such substances as ammonium sulfate, column chromatography, immunopurification methods, and others. See, for instance, R. Scopes, Protein Purification: Principles and Practice, Springer-Verlag: New York (1982); Deutscher, Guide to Protein Purification, Academic Press (1990). For example, antibodies may be raised to the proteins as described herein. Purification from *E. coli* can be achieved following procedures described in U.S. Pat. No. 4,511,503. The protein may then be isolated from cells expressing the protein and further purified by standard protein chemistry techniques as described herein. Detection of the expressed protein is achieved by methods known in the art and include, for example, radioimmunoassays, Western blotting techniques or immunoprecipitation.

Transgenic Plant Regeneration

Transformed plant cells which are derived by any of the above transformation techniques can be cultured to regenerate a whole plant which possesses the transformed genotype. Such regeneration techniques often rely on manipulation of certain phytohormones in a tissue culture growth medium. For transformation and regeneration of maize, see, Gordon-Kamm, et al., (1990) *The Plant Cell* 2:603-618.

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans, et al., Protoplasts Isolation and Culture, Handbook of Plant Cell Culture, Macmillan Publishing Company, New York, pp. 124-176 (1983); and Binding, Regeneration of Plants, Plant Protoplasts, CRC Press, Boca Raton, pp. 21-73 (1985).

The regeneration of plants containing the foreign gene introduced by *Agrobacterium* from leaf explants can be achieved as described by Horsch, et al., (1985) *Science* 227:1229-1231. In this procedure, transformants are grown in the presence of a selection agent and in a medium that induces the regeneration of shoots in the plant species being transformed as described by Fraley, et al., (1983) *Proc. Natl. Acad. Sci. USA* 80:4803. This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Kleen, et al., (1987) *Ann. Rev. of Plant Phys.* 38:467-486. The regeneration of plants from either single plant protoplasts or various explants is well known in the art. See, for example, Methods for Plant Molecular Biology, Weissbach and Weissbach, eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, The Maize Handbook, Freeling and Walbot, Eds., Springer, N.Y. (1994); Corn and Corn Improvement, 3rd edition, Sprague and Dudley Eds., American Society of Agronomy, Madison, Wis. (1988).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed. In vegetatively propagated crops, mature transgenic plants can be propagated by the taking of cuttings or by tissue culture techniques to produce multiple identical plants.

Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit and the like are included in the invention, provided that these parts comprise cells comprising the isolated nucleic acid of the present invention. Progeny and variants and mutants of the regenerated plants are also included within the scope of the invention, provided that these parts comprise the introduced nucleic acid sequences. Transgenic plants expressing the selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, nontransgenic). Back-crossing to a parental plant and out-crossing with a non-transgenic plant are also contemplated.

Modulation of Polypeptide Levels and/or Composition

The present invention further provides a method for modulating (i.e., increasing or decreasing) the concentration or ratio of the polypeptides of the present invention in a plant or part thereof. Modulation can be effected by increasing or decreasing the concentration and/or the ratio of the polypeptides of the present invention in a plant.

The method comprises introducing into a plant cell a recombinant expression cassette comprising a polynucleotide of the present invention as described above to obtain a transformed plant cell, culturing the transformed plant cell under plant cell growing conditions and inducing or repressing expression of a polynucleotide of the present invention in the plant for a time sufficient to modulate concentration and/or the ratios of the polypeptides in the plant or plant part.

In some embodiments, the concentration and/or ratios of polypeptides of the present invention in a plant may be modulated by altering, in vivo or in vitro, the promoter of a gene to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling, et al., PCT/US93/03868. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing or PCR analysis using primers specific to the promoter and to the gene and detecting amplicons produced therefrom. A plant or plant part altered or modified by the foregoing embodiments is grown under plant forming conditions for a time sufficient to modulate the concentration and/or ratios of polypeptides of the present invention in the plant. Plant forming conditions are well known in the art and discussed briefly, supra.

In general, concentration or the ratios of the polypeptides is increased or decreased by at least 5%, 10%, 20%, 30%, 40%, 50%, 60%, 70%, 80% or 90% relative to a native control plant, plant part or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds which activate expression from these promoters are well known in the art. In preferred embodiments, the polypeptides of the present invention are modulated in monocots, particularly maize.

Molecular Markers

The present invention provides a method of genotyping a plant comprising a polynucleotide of the present invention. Optionally, the plant is a monocot, such as maize or sorghum. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., Clark, Ed., Plant Molecular Biology: A Laboratory Manual. Berlin, Springer Verlag, 1997. Chapter 7. For molecular marker methods, see generally, "The DNA Revolution" in: Paterson, Genome Mapping in Plants (Austin, Tex., Academic Press/R. G. Landis Company, 1996) pp. 7-21.

The particular method of genotyping in the present invention may employ any number of molecular marker analytic techniques such as, but not limited to, restriction fragment length polymorphisms (RFLPs). RFLPs are the product of allelic differences between DNA restriction fragments resulting from nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed.

Differences in fragment size among alleles represent an RFLP. Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2 or 1 cM of a gene of the present invention.

In the present invention, the nucleic acid probes employed for molecular marker mapping of plant nuclear genomes selectively hybridize, under selective hybridization conditions, to a gene encoding a polynucleotide of the present invention. In preferred embodiments, the probes are selected from polynucleotides of the present invention.

Typically, these probes are cDNA probes or restriction-enzyme treated (e.g., Pst I) genomic clones. The length of the probes is discussed in greater detail, supra, but are typically at least 15 bases in length, more preferably at least 20, 25, 30, 35, 40 or 50 bases in length. Generally, however, the probes are less than about 1 kilobase in length. Preferably, the probes are single copy probes that hybridize to a unique locus in a haploid chromosome complement. Some exemplary restriction enzymes employed in RFLP mapping are EcoRI, EcoRv and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of said genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCA); 2) denaturing gradient gel electrophoresis (DGGE); 3) RNase protection assays; 4) allele-specific oligonucleotides (ASOs); 5) the use of proteins which recognize nucleotide mismatches, such as the E. coli mutS protein and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Thus, the present invention further provides a method of genotyping comprising the steps of contacting, under stringent hybridization conditions, a sample suspected of comprising a polynucleotide of the present invention with a nucleic acid probe. Generally, the sample is a plant sample; preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, (1987) *Nucleic Acids Res.* 15:8125) and the 7-methylguanosine cap structure (Drummond, et al., (1985) *Nucleic Acids Res.* 13:7375). Negative elements include stable intramolecular 5'UTR stem-loop structures (Muesing, et al., (1987) *Cell* 48:691) and AUG sequences or short open reading frames preceded by an appropriate AUG in the 5' UTR (Kozak, supra, Rao, et al., (1988) *Mol. and Cell. Biol.* 8:284). Accordingly, the present invention provides 5' and/or 3' untranslated regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host such as to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see, Devereaux, et al., (1984) *Nucleic Acids Res.* 12:387-395) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50 or 100.

Sequence Shuffling

The present invention provides methods for sequence shuffling using polynucleotides of the present invention, and compositions resulting therefrom. Sequence shuffling is described in PCT Publication Number WO 1997/20078. See also, Zhang, et al., (1997) *Proc. Natl. Acad. Sci. USA* 94:4504-4509. Generally, sequence shuffling provides a means for generating libraries of polynucleotides having a desired characteristic which can be selected or screened for. Libraries of recombinant polynucleotides are generated from a population of related sequence polynucleotides which comprise sequence regions which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be a decreased Km and/or increased KCat over the wild-type protein as provided herein. In other embodiments, a protein or polynucleotide generated from sequence shuffling will have a ligand binding affinity greater than the non-shuffled wild-type polynucleotide.

The increase in such properties can be at least 110%, 120%, 130%, 140% or at least 150% of the wild-type value.

Generic and Consensus Sequences

Polynucleotides and polypeptides of the present invention further include those having: (a) a generic sequence of at least two homologous polynucleotides or polypeptides, respectively, of the present invention and (b) a consensus sequence of at least three homologous polynucleotides or polypeptides, respectively, of the present invention. The generic sequence of the present invention comprises each species of polypeptide or polynucleotide embraced by the generic polypeptide or polynucleotide sequence, respectively. The individual species encompassed by a polynucleotide having an amino acid or nucleic acid consensus sequence can be used to generate antibodies or produce nucleic acid probes or primers to screen for homologs in other species, genera, families, orders, classes, phyla or kingdoms. For example, a polynucleotide having a consensus sequence from a gene family of *Zea mays* can be used to generate antibody or nucleic acid probes or primers to other Gramineae species such as wheat, rice or sorghum.

Alternatively, a polynucleotide having a consensus sequence generated from orthologous genes can be used to identify or isolate orthologs of other taxa. Typically, a polynucleotide having a consensus sequence will be at least 25, 30 or 40 amino acids in length, or 20, 30, 40, 50, 100 or 150 nucleotides in length. As those of skill in the art are aware, a conservative amino acid substitution can be used for amino acids which differ amongst aligned sequence but are from the same conservative substitution group as discussed above. Optionally, no more than 1 or 2 conservative amino acids are substituted for each 10 amino acid length of consensus sequence.

Similar sequences used for generation of a consensus or generic sequence include any number and combination of allelic variants of the same gene, orthologous or paralogous sequences as provided herein. Optionally, similar sequences used in generating a consensus or generic sequence are identified using the BLAST algorithm's smallest sum probability (P (N)). Various suppliers of sequence-analysis software are listed in chapter 7 of Current Protocols in Molecular Biology, Ausubel, et al., Eds., Current Protocols, a joint venture between Greene Publishing Associates, Inc. and John Wiley & Sons, Inc. (Supplement 30).

A polynucleotide sequence is considered similar to a reference sequence if the smallest sum probability in a comparison of the test nucleic acid to the reference nucleic acid is less than about 0.1, more preferably less than about 0.01 or 0.001 and most preferably less than about 0.0001 or 0.00001. Similar polynucleotides can be aligned and a consensus or generic sequence generated using multiple sequence alignment software available from a number of commercial suppliers such as the Genetics Computer Group's (Madison, Wis.) PILEUP software, Vector NTI's (North Bethesda, Md.) ALIGNX or Genecode's (Ann Arbor, Mich.) SEQUENCHER. Conveniently, default parameters of such software can be used to generate consensus or generic sequences.

Machine Applications

The present invention provides machines, articles of manufacture, and processes for identifying, modeling or analyzing the polynucleotides and polypeptides of the present invention. Identification methods permit identification of homologues of the polynucleotides or polypeptides of the present invention while modeling and analysis methods permit recognition of structural or functional features of interest.

A. Machines: Data Processing Systems

In one embodiment, the present invention provides a machine having: 1) a memory comprising data representing at least one genetic sequence, 2) a genetic identification, analysis, or modeling program with access to the data, 3) a data processor which executes instructions according to the program using the genetic sequence or a subsequence thereof and 4) an output for storing or displaying the results of the data processing.

The machine of the present invention is a data processing system, typically a digital computer. The term "computer" includes one or several desktop or portable computers, computer workstations, servers (including intranet or internet servers), mainframes and any integrated system comprising any of the above irrespective of whether the processing, memory, input, or output of the computer is remote or local, as well as any networking interconnecting the modules of the computer. Data processing can thus be remote or distributed amongst several processors at one or multiple sites. The data processing system comprises a data processor, such as a central processing unit (CPU), which executes instructions according to an application program. As used herein, machines, articles of manufacture and processes are exclusive of the machines, manufactures and processes employed by the United States Patent and Trademark Office or the European Patent Office when data representing the sequence of a polypeptide or polynucleotide of the present invention is used for patentability searches.

The machine of the present invention includes a memory comprising data representing at least one genetic sequence. As used herein, "genetic sequence" refers to the primary sequence (i.e., amino acid or nucleotide sequence) of a polynucleotide or polypeptide of the present invention. The genetic sequence can represent a partial sequence from a full-length protein, genomic DNA or full-length cDNA/mRNA. Nucleic acids or proteins comprising a genetic sequence that is identified, analyzed or modeled according to the present invention can be cloned or synthesized.

As those of skill in the art will be aware, the form of memory of a machine of the present invention, or the particular embodiment of the computer readable medium, are not critical elements of the invention and can take a variety of forms. The memory of such a machine includes, but is not limited to, ROM or RAM or computer readable media such as, but not limited to, magnetic media such as computer disks or hard drives or media such as CD-ROMs, DVDs and the like. The memory comprising the data representing the genetic sequence includes main memory, a register and a cache. In some embodiments the data processing system stores the data representing the genetic sequence in memory while processing the data and wherein successive portions of the data are copied sequentially into at least one register of the data processor for processing. Thus, the genetic sequence stored in memory can be a genetic sequence created during computer runtime or stored beforehand. The machine of the present invention includes a genetic identification, analysis, or modeling program (discussed below) with access to the data representing the genetic sequence. The program can be implemented in software or hardware.

The present invention further contemplates that the machine of the present invention will reference, directly or indirectly, a utility or function for the polynucleotide or polypeptide of the present invention. For example, the utility/function can be directly referenced as a data element in the machine and accessible by the program. Alternatively, the utility/function of the genetic can be indirectly referenced to an electronic or written record. The function or utility of the genetic sequence can be a function or utility for the genetic sequence or the data representing the sequence (i.e., the genetic sequence data).

Exemplary function or utilities for the genetic sequence include: 1) its name (per International Union of Biochemistry and Molecular Biology rules of nomenclature) or the function of the enzyme or protein represented by the genetic sequence, 2) the metabolic pathway that the protein represented by the genetic sequence participates in, 3) the substrate or product or structural role of the protein represented by the genetic sequence or 4) the phenotype (e.g., an agronomic or pharmacological trait) affected by modulating expression or activity of the protein represented by the genetic sequence.

The machine of the present invention also includes an output for displaying, printing or recording the results of the identification, analysis or modeling performed using a genetic sequence of the present invention. Exemplary outputs include monitors, printers or various electronic storage mechanisms (e.g., floppy disks, hard drives, main memory) which can be used to display the results or employed as a means to input the stored data into a subsequent application or device.

In some embodiments, data representing a genetic sequence of the present invention is a data element within a data structure. The data structure may be defined by the computer programs that define the processes of identification, modeling, or analysis (see below) or it may be defined by the programming of separate data storage and retrieval programs subroutines or systems. Thus, the present invention provides a memory for storing a data structure that can be accessed by a computer programmed to implement a process for identification, analysis, or modeling of a genetic sequence. The data structure, stored within memory, is associated with the data representing the genetic sequence and reflects the underlying organization and structure of the genetic sequence to facilitate program access to data elements corresponding to logical sub-components of the genetic sequence. The data structure enables the genetic sequence to be identified, analyzed or modeled. The underlying order and structure of a genetic sequence is data representing the higher order organization of the primary sequence. Such higher order structures affect transcription, translation, enzyme kinetics or reflects structural domains or motifs.

Exemplary logical sub-components which constitute the higher order organization of the genetic sequence include but are not limited to: restriction enzyme sites, endopeptidase sites, major grooves, minor grooves, beta-sheets, alpha helices, open reading frames (ORFs), 5' untranslated regions (UTRs), 3' UTRs, ribosome binding sites, glycosylation sites, signal peptide domains, intron-exon junctions, poly-A tails, transcription initiation sites, translation start sites, translation termination sites, methylation sites, zinc finger domains, modified amino acid sites, preproprotein-proprotein junctions, proprotein-protein junctions, transit peptide domains, single nucleotide polymorphisms (SNPs), simple sequence repeats (SSRs), restriction fragment length polymorphisms (RFLPs), insertion elements, transmembrane spanning regions and stem-loop structures.

In another embodiment, the present invention provides a data processing system comprising at least one data structure in memory where the data structure supports the accession of data representing a genetic sequence of the present invention. The system also comprises at least one genetic identification, analysis or modeling program which directs the execution of instructions by the system using the genetic sequence data to identify, analyze or model at least one data element which is a logical sub-component of the genetic sequence. An output for the processing results is also provided.

B. Articles of Manufacture: Computer Readable Media

In one embodiment, the present invention provides a data structure in a computer readable medium that contains data representing a genetic sequence of the present invention. The data structure is organized to reflect the logical structuring of the genetic sequence, so that the sequence can be analyzed by software programs capable of accessing the data structure. In particular, the data structures of the present invention organize the genetic sequences of the present invention in a manner which allows software tools to perform an identification, analysis or modeling using logical elements of each genetic sequence.

In a further embodiment, the present invention provides a machine-readable media containing a computer program and genetic sequence data. The program provides instructions sufficient to implement a process for effecting the identification, analysis or modeling of the genetic sequence data. The media also includes a data structure reflecting the underlying organization and structure of the data to facilitate program access to data elements corresponding to logical sub-components of the genetic sequence, the data structure being inherent in the program and in the way in which the program organizes and accesses the data.

An example of a data structure resembles a layered hash table, where in one dimension the base content of the sequence is represented by a string of elements A, T, C, G and N. The direction from the 5' end to the 3' end is reflected by the order from the position 0 to the position of the length of the string minus one. Such a string, corresponding to a nucleotide sequence of interest, has a certain number of substrings, each of which is delimited by the string position of its 5' end and the string position of its 3' end within the parent string. In a second dimension, each substring is associated with or pointed to one or multiple attribute fields. Such attribute fields contain annotations to the region on the nucleotide sequence represented by the substring.

For example, a sequence under investigation is 520 bases long and represented by a string named SeqTarget. There is a minor groove in the 5' upstream non-coding region from position 12 to 38, which is identified as a binding site for an enhancer protein HM-A, which in turn will increase the transcription of the gene represented by SeqTarget. Here, the substring is represented as (12, 38) and has the following attributes: [upstream uncoded], [minor groove], [HM-A binding] and [increase transcription upon binding by HM-A]. Similarly, other types of information can be stored and structured in this manner, such as information related to the whole sequence, e.g., whether the sequence is a full length viral gene, a mammalian house keeping gene or an EST from clone X, information related to the 3' down stream non-coding region, e.g., hair pin structure and information related to various domains of the coding region, e.g., Zinc finger.

This data structure is an open structure and is robust enough to accommodate newly generated data and acquired knowledge. Such a structure is also a flexible structure. It can be trimmed down to a1-D string to facilitate data mining and analysis steps, such as clustering, repeat-masking, and HMM analysis. Meanwhile, such a data structure also can extend the associated attributes into multiple dimensions. Pointers can be established among the dimensioned attributes when needed to facilitate data management and processing in a comprehensive genomics knowledge base. Furthermore, such a data structure is object-oriented. Polymorphism can be represented by a family or class of sequence objects, each of which has an internal structure as discussed above. The common traits are abstracted and assigned to the parent object, whereas each child object represents a specific variant of the family or class. Such a data structure allows data to be efficiently retrieved, updated and integrated by the software applications associated with the sequence database and/or knowledge base.

C. Processes: Identification, Analysis or Modeling

The present invention also provides a process of identifying, analyzing or modeling data representing a genetic sequence of the present invention. The process comprises: 1) providing a machine having a hardware or software implemented genetic sequence identification, modeling or analysis program with data representing a genetic sequence, 2) executing the program while granting it access to the genetic sequence data, and 3) displaying or outputting the results of the identification, analysis, or modeling. Data structures made by the processes of the present invention and embodied within a computer readable medium are also provided herein.

A further process of the present invention comprises providing a memory embodied with data representing a genetic sequence and developing within the memory a data structure associated with the data and reflecting the underlying organization and structure of the data to facilitate program access to data elements corresponding to logical subcomponents of the sequence. A computer is programmed with a program containing instructions sufficient to implement the process for effecting the identification, analysis or modeling of the genetic sequence and the program is executed on the computer while granting the program access to the data and to the data structure within the memory. The program results are outputted.

Identification, analysis and modeling programs are well known in the art and available commercially. The program typically has at least one application to: 1) identify the structural role or enzymatic function of the gene which the genetic sequence encodes or is translated from, 2) analyzes and identifies higher order structures within the genetic sequence or 3) model the physico-chemical properties of a genetic sequence of the present invention in a particular environment.

Included amongst the modeling/analysis tools are methods to: 1) recognize overlapping sequences (e.g., from a sequencing project) with a polynucleotide of the present invention and create an alignment called a "contig", 2) identify restriction enzyme sites of a polynucleotide of the present invention, 3) identify the products of a TI ribonuclease digestion of a polynucleotide of the present invention, 4) identify PCR primers with minimal self-complementarity, 5) compute pairwise distances between sequences in an alignment, reconstruct phylogentic trees using distance methods and calculate the degree of divergence of two protein coding regions, 6) identify patterns such as coding regions, terminators, repeats and other consensus patterns in polynucleotides of the present invention, 7) identify RNA secondary structure, 8) identify sequence motifs, isoelectric point, secondary structure, hydrophobicity and antigenicity in polypeptides of the present invention, 9) translate polynucleotides of the present invention and backtranslate polypeptides of the present invention and 10) compare two protein or nucleic acid sequences and identifying points of similarity or dissimilarity between them.

Identification of the function/utility of a genetic sequence is typically achieved by comparative analysis to a gene/protein database and establishing the genetic sequence as a candidate homologue (i.e., ortholog or paralog) of a gene/protein of known function/utility.

A candidate homologue has statistically significant probability of having the same biological function (e.g., catalyzes the same reaction, binds to homologous proteins/nucleic acids, has a similar structural role) as the reference sequence to which it is compared. Sequence identity/similarity is frequently employed as a criterion to identify candidate homologues. In the same vein, genetic sequences of the present invention have utility in identifying homologs in animals or other plant species, particularly those in the family Gramineae such as, but not limited to, sorghum, wheat or rice. Function is frequently established on the basis of sequence identity/similarity. Exemplary sequence comparison systems are provided for in sequence analysis software such as those provided by the Genetics Computer Group (Madison, Wis.) or InforMax</RTI.

The present invention further provides methods for detecting a polynucleotide of the present invention in a nucleic acid sample suspected of containing a polynucleotide of the present invention, such as a plant cell lysate, particularly a lysate of maize. In some embodiments, a gene of the present invention or portion thereof can be amplified prior to the step of contacting the nucleic acid sample with a polynucleotide of the present invention. The nucleic acid sample is contacted with the polynucleotide to form a hybridization complex. The polynucleotide hybridizes under stringent conditions to a gene encoding a polypeptide of the present invention. Formation of the hybridization complex is used to detect a gene encoding a polypeptide of the present invention in the nucleic acid sample. Those of skill will appreciate that an isolated nucleic acid comprising a polynucleotide of the present invention should lack cross-hybridizing sequences in common with non-target genes that would yield a false positive result.

Detection of the hybridization complex can be achieved using any number of well known methods. For example, the nucleic acid sample, or a portion thereof, may be assayed by hybridization formats including but not limited to, solution phase, solid phase, mixed phase or in situ hybridization assays. Briefly, in solution (or liquid) phase hybridizations, both the target nucleic acid and the probe or primer are free to interact in the reaction mixture. In solid phase hybridization assays, probes or primers are typically linked to a solid support where they are available for hybridization with target nucleic in solution. In mixed phase, nucleic acid intermediates in solution hybridize to target nucleic acids in solution as well as to a nucleic acid linked to a solid support. In in situ hybridization, the target nucleic acid is liberated from its cellular surroundings in such as to be available for hybridization within the cell while preserving the cellular morphology for subsequent interpretation and analysis. The following articles provide an overview of the various hybridization assay formats: Singer, et al., (1986) *Biotechniques* 4(3):230-250; Haase, et al., (1984) *Methods in Virology* 7:189-226; Wilkinson, The theory and practice of in situ hybridization in: In situ Hybridization, Wilkinson, Ed., IRL Press, Oxford University Press, Oxford; and Nucleic Acid Hybridization: A Practical Approach, Hames, and Higgins, Eds., IRL Press (1987).

Nucleic Acid Labels and Detection Methods

The means by which nucleic acids of the present invention are labeled is not a critical aspect of the present invention and can be accomplished by any number of methods currently known or later developed. Detectable labels suitable for use in the present invention include any composition detectable by spectroscopic, radioisotopic, photochemical, biochemical, immunochemical, electrical, optical or chemical means.

Useful labels in the present invention include biotin for staining with labeled streptavidin conjugate, magnetic beads, fluorescent dyes (e.g., fluorescein, Texas red, rhodamine, green fluorescent protein and the like), radiolabels (e.g., 3H, 125I, 35S, I4C or 32P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

Nucleic acids of the present invention can be labeled by any one of several methods typically used to detect the presence of hybridized nucleic acids. One common method of detection is the use of autoradiography using probes labeled with 3H, I25I, 35S, I4C or 32P or the like. The choice of radioactive isotope depends on research preferences due to ease of synthesis, stability and half lives of the selected isotopes. Other labels include ligands which bind to antibodies labeled with fluorophores, chemiluminescent agents and enzymes. Alternatively, probes can be conjugated directly with labels such as fluorophores, chemiluminescent agents or enzymes. The choice of label depends on sensitivity required, ease of conjugation with the probe, stability requirements and available instrumentation. Labeling the nucleic acids of the present invention is readily achieved such as by the use of labeled PCR primers.

In some embodiments, the label is simultaneously incorporated during the amplification step in the preparation of the nucleic acids. Thus, for example, polymerase chain reaction (PCR) with labeled primers or labeled nucleotides will provide a labeled amplification product. In another embodiment, transcription amplification using a labeled nucleotide (e.g., fluorescein-labeled UTP and/or CTP) incorporates a label into the transcribed nucleic acids.

Non-radioactive probes are often labeled by indirect means. For example, a ligand molecule is covalently bound to the probe. The ligand then binds to an anti-ligand molecule which is either inherently detectable or covalently bound to a detectable signal system, such as an enzyme, a fluorophore or a chemiluminescent compound. Enzymes of interest as labels will primarily be hydrolases, such as phosphatases, esterases and glycosidases or oxidoreductases, particularly peroxidases. Fluorescent compounds include fluorescein and its derivatives, rhodamine and its derivatives, dansyl, umbelliferone, etc. Chemiluminescers include luciferin and 2,3-dihydrophthalazinediones, e.g., luminol.

Ligands and anti-ligands may be varied widely. Where a ligand has a natural anti-ligand, namely ligands such as biotin, thyroxine and cortisol, it can be used in conjunction with its labeled, naturally occurring anti-ligands. Alternatively, any haptenic or antigenic compound can be used in combination with an antibody. Probes can also be labeled by direct conjugation with a label. For example, cloned DNA probes have been coupled directly to horseradish peroxidase or alkaline phosphatase.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate and colorimetric labels are detected by simply visualizing the colored label.

Antibodies to Proteins

Antibodies can be raised to a protein of the present invention, including individual, allelic, strain or species variants and fragments thereof, both in their naturally occurring (full-length) forms and in recombinant forms. Additionally, antibodies are raised to these proteins in either their native configurations or in non-native configurations. Many methods of making antibodies are known to persons of skill. A variety of analytic methods are available to generate a hydrophilicity profile of a protein of the present invention. Such methods can be used to guide the artisan in the selection of peptides of the present invention for use in the generation or selection of antibodies which are specifically reactive, under immunogenic conditions, to a protein of the present invention. See, e.g., Janin, (1979) *Nature* 277:491-492; Wolfenden, et al., (1981) *Biochemistry* 20:849-855; Kyte and Doolite, (1982) *J. Mol. Biol.* 157:105-132; Rose, et al., (1985) *Science* 229:834-838. The following discussion is presented as a general overview of the techniques available; however, one of skill will recognize that many variations upon the following methods are known.

A number of immunogens are used to produce antibodies specifically reactive with a protein of the present invention. An isolated recombinant, synthetic, or native polynucleotide of the present invention are the preferred antigens for the production of monoclonal or polyclonal antibodies. Polypeptides of the present invention are optionally denatured, and optionally reduced, prior to formation of antibodies for screening expression libraries or other assays in which a putative protein of the present invention is expressed or denatured in a non-native secondary, tertiary or quaternary structure.

The protein of the present invention is then injected into an animal capable of producing antibodies. Either monoclonal or polyclonal antibodies can be generated for subsequent use in immunoassays to measure the presence and quantity of the protein of the present invention. Methods of producing polyclonal antibodies are known to those of skill in the art. In brief, an antigen, preferably a purified protein, a protein coupled to an appropriate carrier (e.g., GST, keyhole limpet hemanocyanin, etc.) or a protein incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the protein of interest. When appropriately high titers of antibody to the immunogen are obtained, blood is collected from the animal and antisera are prepared. Further fractionation of the antisera to enrich for antibodies reactive to the protein is performed where desired (See, e.g., Coligan, (1991) Current Protocols in Immunology, Wiley/Greene, N.Y.; and Harlow and Lane, Antibodies: A Laboratory Manual, Cold Spring Harbor Press, NY (1989)).

Antibodies, including binding fragments and single chain recombinant versions thereof, against predetermined fragments of a protein of the present invention are raised by immunizing animals, e.g., with conjugates of the fragments with carrier proteins as described above. Typically, the immunogen of interest is a protein of at least about 5 amino acids, more typically the protein is 10 amino acids in length, preferably, 15 amino acids in length and more preferably the protein is 20 amino acids in length or greater. The peptides are typically coupled to a carrier protein (e.g., as a fusion protein), or are recombinantly expressed in an immunization vector. Antigenic determinants on peptides to which antibodies bind are typically 3 to 10 amino acids in length.

Monoclonal antibodies are prepared from hybrid cells secreting the desired antibody. Monoclonals antibodies are screened for binding to a protein from which the antigen was derived. Specific monoclonal and polyclonal antibodies will usually have an antibody binding site with an affinity constant for its cognate monovalent antigen at least between 106-107, usually at least 108, preferably at least 109, more preferably at least 110 and most preferably at least 111 liters/mole.

In some instances, it is desirable to prepare monoclonal antibodies from various mammalian hosts, such as mice, rodents, primates, humans, etc. Description of techniques for preparing such monoclonal antibodies are found in, e.g., Basic and Clinical Immunology, 4th ed., Stites, et al., Eds., Lange Medical Publications, Los Altos, Calif., and references cited therein; Harlow and Lane, supra; Goding, Monoclonal Antibodies: Principles and Practice, 2nd ed., Academic Press, New York, N.Y. (1986); and Kohler and Milstein, (1975) *Nature* 256:495-497. Summarized briefly, this method proceeds by injecting an animal with an antigen comprising a protein of the present invention. The animal is then sacrificed and cells taken from its spleen, which are fused with myeloma cells. The result is a hybrid cell or "hybridoma" that is capable of reproducing in vitro.

The population of hybridomas is then screened to isolate individual clones, each of which secrete a single antibody species to the antigen. In this manner, the individual antibody species obtained are the products of immortalized and cloned single B cells from the immune animal generated in response to a specific site recognized on the antigenic substance.

Other suitable techniques involve selection of libraries of recombinant antibodies in phage or similar vectors (see, e.g., Huse, et al., (1989) *Science* 246:1275-1281; and Ward, et al., (1989) *Nature* 341:544-546 and Vaughan, et al., (1996) *Nature Biotechnology* 14:309-314). Alternatively, high avidity human monoclonal antibodies can be obtained from transgenic mice comprising fragments of the unrearranged human heavy and light chain Ig loci (i.e., mini locus transgenic mice). Fishwild, et al., (1996) *Nature Biotech.* 14:845-851. Also, recombinant immunoglobulins may be produced. See, Cabilly, U.S. Pat. No. 4,816,567 and Queen, et al., (1989) *Proc. Natl. Acad. Sci.* 86:10029-10033.

The antibodies of this invention are also used for affinity chromatography in isolating proteins of the present invention. Columns are prepared, e.g., with the antibodies linked to a solid support, e.g., particles, such as agarose, SEPHADEX, or the like, where a cell lysate is passed through the column, washed and treated with increasing concentrations of a mild denaturant, whereby purified protein are released.

The antibodies can be used to screen expression libraries for particular expression products such as normal or abnormal protein. Usually the antibodies in such a procedure are labeled with a moiety allowing easy detection of presence of antigen by antibody binding. Antibodies raised against a protein of the present invention can also be used to raise anti-idiotypic antibodies. These are useful for detecting or diagnosing various pathological conditions related to the presence of the respective antigens.

Frequently, the proteins and antibodies of the present invention will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles and the like.

Plants exhibiting an altered ethylene-dependent phenotype as compared with wild-type plants can be selected among other methods, by visual observation. For example, an altered ethylene-dependent phenotype may be detected by utilization of the "triple response." The "triple response" consists of three distinct morphological changes in dark-grown seedlings upon exposure to ethylene: inhibition of hypocotyl and root elongation, radial swelling of the stem and exaggeration of the apical hook. Thus, a triple response displayed in the presence of ethylene inhibitors would indicate one type of altered ethylene-dependent phenotype. Ethylene affects a vast array of agriculturally important plant processes, including fruit ripening, flower and leaf senescence and leaf abscission. The ability to control the sensitivity of plants to ethylene could thus significantly improve the quality and longevity of many crops. The invention includes plants produced by the method of the invention, as well as plant tissue and seeds.

Although the present invention has been described in some detail by way of illustration and example for purposes of clarity of understanding, it will be obvious that certain changes and modifications may be practiced within the scope of the appended claims.

EXAMPLE 1

This example describes the construction of the cDNA libraries. Total RNA for SEQ ID NO: 1 (EIN3), SEQ ID NO: 3 (EBF1), SEQ ID NO: 5 (EBF2), SEQ ID NO: 7 (EIN5) or SEQ ID NO: 9 (ERF3) was obtained from maize genotype Hill (Armstrong and Phillips, (1988) *Crop Sci.* 28:363-369) and for ZmEIN3-2 (SEQ ID NO: 1), from night harvested leaf tissue at the V8-V10 stage of maize genotype B75. The total RNA was isolated from the maize tissues with TRIzol Reagent (Life Technology Inc. Gaithersburg, Md.) using a modification of the guanidine isothiocyanate/acid-phenol procedure described by Chomczynski and Sacchi (Chomczynski and Sacchi, (1987) *Anal. Biochem.* 162:156). In brief, plant tissue samples were pulverized in liquid nitrogen before the addition of the TRIzol Reagent, and then were further homogenized with a mortar and pestle. Addition of chloroform followed by centrifugation was conducted for separation of an aqueous phase and an organic phase. The total RNA was recovered by precipitation with isopropyl alcohol from the aqueous phase.

Poly (A)+RNA Isolation

The selection of poly (A)+RNA from total RNA was performed using PolyATact system (Promega Corporation. Madison, Wis.). In brief, biotinylated oligo (dT) primers were used to hybridize to the 3' poly (A) tails on mRNA. The hybrids were captured using streptavidin coupled to paramagnetic particles and a magnetic separation stand. The mRNA was washed at high stringency conditions and eluted by RNase-free deionized water. cDNA Library Construction cDNA synthesis was performed and unidirectional cDNA libraries were constructed using the SuperScript Plasmid System (Life Technology Inc. Gaithersburg, Md.). The first strand of cDNA was synthesized by priming an oligo (dT) primer containing a Not I site.

The reaction was catalyzed by SuperScript Reverse Transcriptase II at 45° C. The second strand of cDNA was labeled with alpha-32P-dCTP and a portion of the reaction was analyzed by agarose gel electrophoresis to determine cDNA sizes. cDNA molecules smaller than 500 base pairs and unligated adapters were removed by Sephacryl-S400 chromatography. The selected cDNA molecules were ligated into pSPORT1 vector in between of Not I and Sal I sites.

EXAMPLE 2

This example describes cDNA sequencing and library subtraction. Sequencing Template Preparation: Individual colonies were picked and DNA was prepared either by PCR with M13 forward primers and M13 reverse primers, or by plasmid isolation. All the cDNA clones were sequenced using M13 reverse primers.

Q-bot Subtraction Procedure: cDNA libraries subjected to the subtraction procedure were plated out on 22×22 cm$^2$ agar plate at density of about 3,000 colonies per plate. The plates were incubated in a 37° C. incubator for 12-24 hours. Colonies were picked into 384-well plates by a robot colony picker, Q-bot (GENETIX Limited). These plates were incubated overnight at 37° C.

Once sufficient colonies were picked, they were pinned onto 22×22 cm$^2$ nylon membranes using Q-bot. Each membrane contained 9,216 colonies or 36,864 colonies. These membranes were placed onto agar plate with appropriate antibiotic. The plates were incubated at 37° C. for overnight.

After colonies were recovered on the second day, these filters were placed on filter paper pre-wetted with denaturing solution for four minutes, then were incubated on top of a boiling water bath for additional four minutes. The filters were then placed on filter paper pre-wetted with neutralizing solution for four minutes. After excess solution was removed by placing the filters on dry filter papers for one minute, the colony side of the filters were place into Proteinase K solution, incubated at 37° C. for 40-50 minutes. The filters were placed on dry filter papers to dry overnight. DNA was then cross-linked to nylon membrane by UV light treatment. Colony hybridization was conducted as described by Sambrook, et al., (in Molecular Cloning: A laboratory Manual, 2nd Edition). The following probes were used in colony hybridization:

1. First strand cDNA from the same tissue as the library was made from to remove the most redundant clones.

2. 48-192 most redundant cDNA clones from the same library based on previous sequencing data.

3. 192 most redundant cDNA clones in the entire maize sequence database.

4. ASal-A20 oligo nucleotide: TCG ACC CAC GCG TCC GAA AAA AAA AAA AAA AAA AAA, removes clones containing a poly A tail but no cDNA.

5. cDNA clones derived from rRNA.

The image of the autoradiography was scanned into computer and the signal intensity and cold colony addresses of each colony was analyzed. Re-arraying of cold colonies from 384 well plates to 96 well plates was conducted using Q-bot.

EXAMPLE 3

This example describes identification of the gene from a computer homology search. Gene identities were determined by conducting BLAST (Basic Local Alignment Search Tool; Altschul, et al., (1993) *J. Mol. Biol.* 215:403-410; see also, National Center for Biotechnology Information, National Library of Medicine, Building 38A, Bethesda, Md., USA) searches under default parameters for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL and DDBJ databases). The cDNA sequences were analyzed for similarity to all publicly available DNA sequences contained in the "nr" database using the BLASTN algorithm.

The DNA sequences were translated in all reading frames and compared for similarity to all publicly available protein sequences contained in the "nr" database using the BLASTX algorithm (Gish and States, (1993) *J. Nature Genetics* 3:266-272) provided by the NCBI. In some cases, the sequencing data from two or more clones containing overlapping segments of DNA were used to construct contiguous DNA sequences.

EXAMPLE 4

Vector Construction and Over Expression of ZM-ERF3 in Maize

PHP21751-UBI:ZM-ERF3

The coding sequence of ZM-ERF3 was amplified by PCR and cloned into pCR2.1 TOPO vector (Invitrogen). ZM-ERF3 was sequence verified and ligated into a vector containing the maize UBI promoter and PINII terminator. The gene cassette was then ligated to generate UBI PRO:ZM-ERF3:PINII TERM+35S:BAR:PINII. 35S:BAR is used as a herbicide resistance marker. The expression vector was quality checked by restriction digestion mapping and transferred into *Agrobacterium tumefaciens* LB4404JT by electroporation. This *Agrobacterium* strain was used to transform GS3 maize inbred. Molecular analyses on T0 events were performed and single copy transgene expressing events were advanced for further experiments.

PHP25534-RAB17:ZM-ERF3

The coding sequence of ZM-ERF3 was amplified by PCR and cloned into pCR2.1 TOPO vector (Invitrogen). ZM-ERF3 was sequence verified and ligated into a vector containing the maize RAB17 promoter and GZ-W64A terminator, as well as Gateway (Invitrogen) ATT sites. The entry vector in combination with a destination vector was used in a single site Gateway (Invitrogen) reaction to generate RAB17:ZM-EFR3:GZ-W64A+UBI:MOPAT:PINII+LTP2:DS-RED:PINII. UBI:MOPAT and LTP2:RFP are used as herbicide resistance and visible markers, respectively. The expression vector was quality checked by restriction digestion mapping and transferred into *Agrobacterium tumefaciens* LB4404JT by electroporation. This *Agrobacterium* strain was used to transform GS3 maize inbred. Molecular analyses on T0 events were performed and single copy transgene expressing events were advanced for further experiments. Advancement comprises self-pollination or pollination with the parent genotype and selection for the transgenic progeny. For example, T1 progeny comprises two doses of the parental genotype and may be referred to as D2. Advanced lines may be crossed with a tester genotype for field evaluation.

Hybrid material representing ten events of PHP25534 was planted in replicated field trials subjected to drought stress during the grain-fill stage (i.e., within the R2 to R5 stages as described in *How a Corn Plant Develops*, Iowa State University of Science and Technology Cooperative Extension Service Special Report No. 48, Reprinted June 1993.) Four of ten events showed statistically significant improved yield under drought stress as compared to controls. One of those four events also demonstrated statistically significant improved performance in seedling assays for drought tolerance and for early vigor under low-temperature stress.

PHP25536-RYE CBF31 PRO:ZM-ERF3

The coding sequence of ZM-ERF3 was amplified by PCR and cloned into pCR2.1 TOPO vector (Invitrogen). ZM-ERF3 was sequence verified and ligated along with the RYE CBF31 promoter (U.S. patent application Ser. No. 12/256,568 filed 23 Oct. 2008) into a vector containing the maize GZ-W64A terminator, as well as Gateway (Invitrogen) ATT sites. The entry vector in combination with a destination vector was used in a single site Gateway (Invitrogen) reaction to generate RAB17:ZM-EFR3:GZ-W64A+UBI:MOPAT:PINII+LTP2:DS-RED:PINII. UBI:MOPAT and LTP2:RFP are used as herbicide resistance and visible markers, respectively. The expression vector was quality checked by restriction digestion mapping and transferred into *Agrobacterium tumefaciens* LB4404JT by electroporation. This *Agrobacterium* strain was used to transform GS3 maize inbred. Molecular analyses on T0 events were performed and single copy transgene expressing events were advanced for further experiments. Advancement comprises self-pollination or pollination with the parent genotype and selection for the transgenic progeny. For example, T1 progeny comprises two doses of the parental genotype and may be referred to as D2. Advanced lines may be crossed with a tester genotype for field evaluation.

Hybrid material representing 9 events of PHP25536 was planted in replicated field trials subjected to drought stress during the grain-fill stage. Three of nine events showed statistically significant improved yield under drought stress as compared to controls. Two of those three events, and two additional events, demonstrated statistically significant improved performance in seedling assays for early vigor under low-temperature stress.

PHP25537-RYE CBF31 PRO:ZM-ERF3+RYE CBF31 PRO:ZM-CBF2

The coding sequence of ZM-ERF3 was amplified by PCR and cloned into pCR2.1 TOPO vector (Invitrogen). ZM-ERF3 was sequence verified & ligated along with the RYE CBF31 promoter into a vector containing the maize GZ-W64A terminator, as well as Gateway (Invitrogen) ATT sites. The entry vector in combination with a RYE CBF31 PRO:ZM-CBF2 entry vector were used in a multisite Gateway (Invitrogen) reaction to generate RYE CBF31 PRO:ZM-EFR3:GZ-W64A+RYE CBF31:ZM-CBF2:PINII+UBI:MOPAT:PINII. UBI:MOPAT is used as a herbicide resistance marker. The expression vector was quality checked by restriction digestion mapping and transferred into *Agrobacterium tumefaciens* LB4404JT by electroporation. This *Agrobacterium* strain was used to transform GS3 maize inbred. Molecular analyses on T0 events were performed and single copy transgene expressing events were advanced for further experiments.

PHP25538-RYE CBF31 PRO:ZM-ERF3+RYE CBF31 PRO:RYE CBF31

The coding sequence of ZM-ERF3 was amplified by PCR and cloned into pCR2.1 TOPO vector (Invitrogen). ZM-ERF3 was sequence verified and ligated along with the RYE CBF31 promoter into a vector containing the maize GZ-W64A terminator, as well as Gateway (Invitrogen) ATT sites. The entry vector in combination with a RYE CBF31 PRO:RYE CBF31 entry vector were used in a multisite Gateway (Invitrogen) reaction to generate RYE CBF31 PRO:ZM-EFR3:GZ-W64A+RYE CBF31:RYE:CBF31:GZ-W64A+UBI:MOPAT:PINII. UBI:MOPAT is used as a herbicide resistance marker. The expression vector was quality checked by restriction digestion mapping and transferred into *Agrobacterium tumefaciens* LB4404JT by electroporation. This *Agrobacterium* strain was used to transform GS3 maize inbred. Molecular analyses on T0 events were performed and single copy transgene expressing events were advanced for further experiments.

PHP26620-RD29A PRO:ZM-ERF3+RD29A:RYE CBF31

The coding sequence of ZM-ERF3 was amplified by PCR and cloned into pCR2.1 TOPO vector (Invitrogen). ZM-ERF3 was sequence verified and ligated along with the RD29A promoter into a vector containing the PINII terminator, as well as Gateway (Invitrogen) ATT sites. The entry vector in combination with a RD29A PRO:RYE CBF31 entry vector were used in a multisite Gateway (Invitrogen) reaction to generate RD29A PRO:ZM-EFR3:PINII+RD29A:RYE:CBF31:GZ-W64A+UBI:MOPAT:PINII. UBI:MOPAT is used as a herbicide resistance marker. The expression vector was quality checked by restriction digestion mapping and transferred into *Agrobacterium tumefaciens* LB4404JT by electroporation. This *Agrobacterium* strain was used to transform EF09B maize inbred. Molecular analyses on T0 events were performed and single copy transgene expressing events were advanced for further experiments. Statistically significant yield improvement was observed in one of two events tested under separate drought stresses at anthesis and during grain-fill.

EXAMPLE 5

Vector Construction and Gene Silencing of ZM-EIN3 in Maize

UBI:EIN3:PINII RNAi

Two ~500 base pair (sense and anti-sense) truncated fragments of the ZM-EIN3 gene were amplified by PCR and cloned into an Invitrogen TOPO vector. The ZM-EIN3 sense and anti-sense truncated fragments were sequence verified and ligated, along with an ADH1 intron loop sequence into a vector containing the maize UBI promoter and PINII terminator, as well as Gateway (Invitrogen) ATT sites. The entry vector in combination with a destination vector was used in a single site Gateway (Invitrogen) reaction to generate UBI:ZM-EIN3:PINII RNAi+UBI:MOPAT:PINII+LTP2:DS-RED:PINII. UBI:MOPAT and LTP2:RFP are used as herbicide resistance and visible markers, respectively. The expression vector was quality checked by restriction digestion mapping and transferred into *Agrobacterium tumefaciens* LB4404JT by electroporation. This *Agrobacterium* strain was used to transform EFO9B maize inbred. Molecular analyses on T0 events were performed and single copy transgene expressing events were advanced for further experiments.

EXAMPLE 6

Sequence Isolation and Endogenous Expression

Sequence Isolation

The ethylene signaling genes EIN3 and EIN5 are being used in down-regulation constructs using the RNAi strategy. Two RNAi constructs for EIN3 and one for EIN5 have been prepared. In the case of EIN3, full-insert sequence from cfp7n.pk010.h4 (PCO642867) has been used to generate two RNAi constructs with truncated fragments of approximately 500 bp at the 5' end of the coding sequence. One of the two constructs included the starting ATG in the RNAi fragment, while the second avoided the use of the starting ATG and started immediately after. The EIN5 RNAi construct was prepared using approximately 500 bp at the 5' end of the coding sequence, starting immediately after the first ATG.

Fragments for the EIN5 RNAi construct were amplified from cfp5n.pk005.c17.f:fis (PCO637491).

Expression information:

The maize ethylene genes ERF3, EIN3, EIN5, EBF1 and EBF2 are expressed in all tissues in the plant (Table 1). Endogenous expression of ZmERF3 is found to be highest in vascular bundles showing an MPSS expression level (Solexa, Hayward, CA; Brenner, et al., (2000) Nature Biotechnology 18:630-634) of 628 ppm, while the gene is expressed in practically all maize tissues (FIG. 1). The highest expression levels observed for ZmEIN3, ZmEIN5, ZmEBF1 and ZmEBF2 are, respectively, 1603 ppm (internodes), 168 ppm (ear meristem), 560 ppm (root) and 902 ppm (root).

Figure 2:
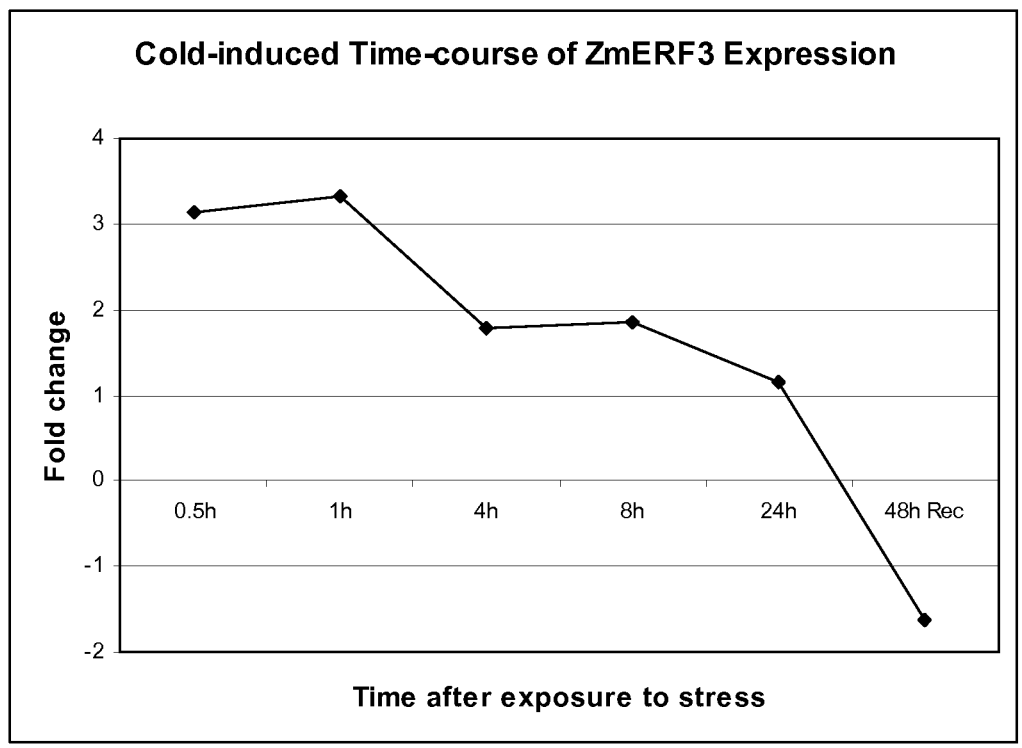
FIG. 2 is a graph showing the cold-induced time-course of Zm ERF3 expression in microarrays.

The genes under consideration here also show differential expression in the presence of stresses or hormones, as indicated in Table 1. ZmERF3 is observed to be induced by drought in most tissues, although one experiment indicated downregulation of the gene in leaves and roots under drought. It is also observed to be downregulated by cold stress. The expression of this gene appears to be closely related to the time of exposure to the stress, as indicated by a microarray experiment conducted to determine the cold-induced time-course of gene expression in maize seedling leaves. The expression of the gene was found highest at the very early time point of 0.5 hour after exposure to cold stress, and thereafter it declined to normal uninduced levels by 24 hours after exposure to stress (FIG. 2).

ZmEIN3 is induced by drought stress, and to a lesser extent by cold stress, in aerial tissues, while it appears to be downregulated by drought in the root. It also shows a higher expression in response to ABA treatment during the early hours (24 h) of ABA exposure. In contrast to this, ZmEIN5 expression is downregulated in most aerial tissues by drought and upregulated in root. It shows enhanced expression upon treatment with both ABA and ethylene.

Expression of ZmEBF1 and ZmEBF2 appears to be more or less similarly regulated in the plant. Both are upregulated by drought in aerial tissues and downregulated in roots. In addition, ZmEBF1 is induced by cold stress, while ZmEBF2 is induced by both ABA and ethylene treatment.

Expression information:

Downstream gene expression in UBI::Zm ERF3 transgenic maize

Figure 3:
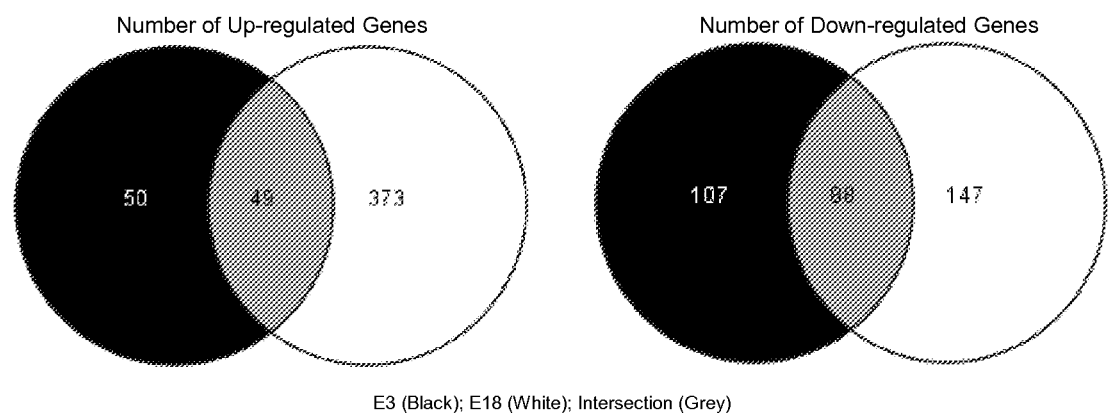
FIG. 3 is a diagram showing the number of genes upregulated or down-regulated more than 5-fold both in E3 and E18 of transgenic maize expressing UBI::ZmERF3.

Constitutive over-expression of ZmERF3 in maize resulted in a pleiotropic effect, where the stems of the plants curved as they grew. The plants also exhibited "buggy-whipping", a phenomenon where the newly emerging leaves were tightly curled and bent, during the vegetative stage prior to tasseling. However, they recovered from this phenotype as they grew towards the reproductive stage. Considering that the highest endogenous expression of the gene is in vascular bundles, it is likely that constitutive overexpression resulted in adversely affecting vascular formation in the stem and this caused the curving of the stalk during growth. We analyzed two events, namely E3 and E18, of transgenic maize constitutively expressing ZmERF3 from the UBI promoter, to identify changes in downstream gene expression. The event, E18, showed a pronounced pleiotropic effect, while the event, E3, did not show such an effect. Transgene expression in event E18 was confirmed to be very high by northern blotting, relative to endogenous levels. As ZmERF3 is a transcription factor, constitutive over-expression of this gene would result in either upregulation or downregulation of genes whose expression is regulated at the transcription level by ZmERF3. There was significant overlap between the upregulated and downregulated genes in the two events, with more number of genes showing change in E18 than in E3 (FIG. 3). A list of the genes with known functionality that are up- or down-regulated commonly in the two events is presented in Tables 2 and 3, respectively. Analysis of downstream gene expression indicates the presence of stress and/or ethylene related genes in both the up-regulated and down-regulated categories. In attempting to overcome the pleiotropic effect of UBI::ZmERF3, constructs were designed to express the gene from stress-regulated promoters. Since several stress-related genes are down-regulated in UBI::ZmERF3 transgenics, one RNAi construct will also be prepared to assess the effect of this transcription factor in transgenic stress tolerance.

TABLE 1

Endogenous expression of four ethylene signaling genes as represented in MPSS libraries.

| EXPRESSION DETAILS | GENE | | | | |
|---|---|---|---|---|---|
| | ZM ERF3 | ZM EIN3 | ZM EIN5 | ZM EBF1 | ZM EBF1/2 |
| General Expression Information | | | | | |
| Tissue specificity | All Tissues | All Tissues | All Tissues | All Tissues | All Tissues |
| Highest MPSS expression | Vascular bundles (628 ppm) | Internode (1603 ppm) | Ear Meristem (168 ppm) | Root (560 ppm) | Root (902 ppm) |
| MPSS Tissue Libraries | MPSS Expression (ppm) | | | | |
| Corn pedicels, drought stressed | 162 | 37 | — | 173 | 10 |
| Corn pedicels, watered control | 62 | 8 | — | — | — |
| Corn leaf, drought stressed | 38 | 763 | 21 | 65 | 239 |
| Corn leaf, watered control | 65 | 339 | 36 | — | — |
| Corn root, drought stressed | 219 | 485 | 53 | 15 | — |
| Corn root, watered control | 410 | 650 | 39 | 58 | 27 |
| Corn v5 leaves, ABA treated, 24 hr | 68 | 814 | 33 | — | — |
| Corn v5 leaves, ABA treated, 48 hr | 25 | 518 | 79 | — | 45 |
| Corn v5 leaves, Ethephon treated, 24 hr | 26 | 297 | 22 | — | — |
| Corn v5 leaves, Ethephon treated, 48 hr | 95 | 521 | 55 | — | 59 |
| Corn v5 leaves, control (no hormone treatment) | 57 | 509 | 20 | — | 7 |
| Corn seedling, cold stress | 28 | 459 | — | 30 | — |
| Corn seedling, cold-stress recovery | 25 | 380 | — | — | — |
| Corn seedling, no cold-stress control | 109 | 328 | — | — | — |
| Corn immature ear tips, drought stressed | 12 | — | 68 | 50 | 14 |
| Corn immature ear tips, watered control | — | — | 78 | — | — |
| Corn ear leaf, drought stressed | 100 | — | 3 | — | 44 |

TABLE 1-continued

Endogenous expression of four ethylene signaling genes as represented in MPSS libraries.

| | | | | |
|---|---|---|---|---|
| Corn ear leaf, watered control | 5 | — | 120 | 27 | — |
| Corn 7-DAP apical kernels, drought stressed | 75 | — | 96 | 105 | 24 |
| Corn 7-DAP apical kernels, watered control | 29 | — | 56 | — | 13 |
| Corn 7-DAP Basal Kernels, drought stressed | 82 | — | 128 | 125 | — |
| Corn 7-DAP Basal Kernels, watered control | 58 | — | 99 | 25 | 30 |

TABLE 2

Top-BLAST hit of genes with known functionality that is commonly upregulated in both events 3 and 18 of maize transgenics harboring UBI::ZmERF3.

| Accession | Gene Name | Fold change in E18 |
|---|---|---|
| Q6Z2W4 | AvrRpt2-induced protein 2-like [Oryza sativa (japonica cultivar-group)] | 81.584 |
| Q7XLD7 | OSJNBa0070C17.11 protein [Oryza sativa (japonica cultivar-group)] | 21.523 |
| Q8S0K1 | Selenoprotein-like [Oryza sativa (japonica cultivar-group)] | 26.790 |
| Q5VQ37 | Leaf senescence protein-like [Oryza sativa (japonica cultivar-group)] | 6.737 |
| Q08062 | Malate dehydrogenase [Zea mays] | 9.206 |
| Q0JQR6 | Os01g0143500 protein [Oryza sativa (japonica cultivar-group)] | 9.720 |
| P42390 | Indole-3-glycerol phosphate lyase, chloroplast precursor [Zea mays] | 54.913 |
| Q69XR7 | Putative acyl-CoA oxidase ACX3 [Oryza sativa (japonica cultivar-group)] | 164.089 |
| Q6K4Y6 | Prefoldin-related K | 9.165 |
| Q75I96 | Putative receptor-like kinase [Oryza sativa (japonica cultivar-group)] | 13.604 |
| Q9XF58 | Plasma membrane intrinsic protein [Zea mays] | 5.250 |
| Q43417 | Peroxidase precursor [Cenchrus ciliaris] | 8.826 |
| Q0DX49 | Putative DNA-3-methyladenine glycosylase [Oryza sativa (japonica cultivar-group)] | 10.388 |
| Q6YW60 | Zinc finger (C3HC4-type RING finger) protein-like [Oryza sativa (japonica cultivar-group)] | 12.170 |
| Q5NA53 | Glycogenin-like protein [Oryza sativa (japonica cultivar-group)] | 5.573 |
| O48558 | 60S ribosomal protein L30 [Zea mays] | 12.328 |
| Q7XLD7 | OSJNBa0070C17.11 protein [Oryza sativa (japonica cultivar-group)] | 21.523 |
| A2WNN4 | Os01g0287400 protein [Oryza sativa (indica cultivar-group)] | 41.096 |
| Q75IK0 | Putative o-methyltransferase ZRP4 [Oryza sativa (japonica cultivar-group)] | 17.086 |

TABLE 3

Top-BLAST hit of genes with known functionality that is commonly down-regulated in both events 3 and 18 of maize transgenics harboring UBI::ZmERF3.

| Accession | Gene Name | Fold change in E18 |
|---|---|---|
| Q6Z6M4 | Isocitrate lyase [Oryza sativa (japonica cultivar-group)] | −16.010 |
| Q75HZ0 | Putative late embryogenesis abundant protein [Oryza sativa (japonica cultivar-group)] | −7.250 |
| Q9AVM3 | Cytochrome P450 [Triticum aestivum] | −21.360 |
| Q40680 | Os07g0614500 protein [Oryza sativa] | −11.691 |
| Q10LJ9 | Heavy metal-associated domain containing protein, expressed [Oryza sativa] | −5.053 |
| Q9ZWI4 | ZmGR2c protein [Zea mays] | −7.283 |
| Q6J555 | MADS16 protein [Dendrocalamus latiflorus] | −9.053 |
| A0S6X4 | FT-like protein [Hordeum vulgare subsp. vulgare] | −11.773 |
| Q5VMA5 | Putative lipase [Oryza sativa (japonica cultivar-group)] | −6.354 |
| Q9ZSX1 | Polyprotein [Zea mays] | −6.338 |
| O49010 | Herbicide safener binding protein [Zea mays] | −10.906 |
| Q6L5H6 | Os05g0537400 protein [Oryza sativa (japonica cultivar-group)] | −6.043 |
| Q10SX1 | Sterol desaturase family protein, expressed [Oryza sativa (japonica cultivar-group)] | −5.691 |
| Q2RBL6 | Major Facilitator Superfamily protein, expressed [Oryza sativa (japonica cultivar-group)] | −9.974 |
| Q10S44 | Basic helix-loop-helix, putative, expressed [Oryza sativa (japonica cultivar-group)] | −9.167 |
| Q8W2K4 | Cytochrome b5 reductase isoform II [Zea mays] | −12.870 |
| Q2R2W1 | Adagio-like protein 3 [Oryza sativa] | −6.005 |
| Q69Y12 | Putative aminopeptidase C [Oryza sativa (japonica cultivar-group)] | −31.794 |
| Q53JI5 | POT family, putative [Oryza sativa (japonica cultivar-group)] | −39.680 |
| Q7EYH1 | Putative MDR-like ABC transporter [Oryza sativa (japonica cultivar-group)] | −10.733 |
| Q84ZF7 | Os07g0293000 protein [Oryza sativa (japonica cultivar-group)] | −13.433 |
| Q69J29 | Pectin methylesterase-like protein [Oryza sativa (japonica cultivar-group)] | −8.375 |
| Q8RZV3 | Zinc finger (C3HC4-type RING finger)-like [Oryza sativa (japonica cultivar-group)] | −8.153 |
| Q9LT02 | Putative cation-transporting ATPase [Arabidopsis thaliana] | −5.999 |
| Q7XIR1 | Carbonyl reductase-like protein [Oryza sativa (japonica cultivar-group)] | −7.132 |

EXAMPLE 7

Transformation and Regeneration of Transgenic Plants

Immature maize embryos from greenhouse donor plants are bombarded with a plasmid containing the Ethylene signaling associated sequence operably linked to the drought-inducible promoter RAB17 promoter (Vilardell, et al., (1990) Plant Mol Biol 14:423-432) and the selectable marker gene PAT, which confers resistance to the herbicide Bialaphos. Alternatively, the selectable marker gene is provided on a separate plasmid. Transformation is performed as follows. Media recipes follow below.

Preparation of Target Tissue:

The ears are husked and surface sterilized in 30% Clorox® bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA:

A plasmid vector comprising the Ethylene signaling associated sequence operably linked to an ubiquitin promoter is made. This plasmid DNA plus plasmid DNA containing a PAT selectable marker is precipitated onto 1.1 µm (average diameter) tungsten pellets using a $CaCl_2$ precipitation procedure as follows:

100 µl prepared tungsten particles in water
10 µl (1 µg) DNA in Tris EDTA buffer (1 µg total DNA)
100 µl 2.5 M $CaCl_2$
10 µl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 µl 100% ethanol is added to the final tungsten particle pellet. For particle gun bombardment, the tungsten/DNA particles are briefly sonicated and 10 µl spotted onto the center of each macrocarrier and allowed to dry about 2 minutes before bombardment.

Particle Gun Treatment:

The sample plates are bombarded at level #4 in a particle gun. All samples receive a single shot at 650 PSI, with a total of ten aliquots taken from each tube of prepared particles/DNA.

Subsequent Treatment:

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for increased drought tolerance. Assays to measure improved drought tolerance are routine in the art and include, for example, increased kernel-earring capacity yields under drought conditions when compared to control maize plants under identical environmental conditions. Alternatively, the transformed plants can be monitored for a modulation in meristem development (i.e., a decrease in spikelet formation on the ear). See, for example, Bruce, et al., (2002) *Journal of Experimental Botany* 53:1-13.

Bombardment and Culture Media:

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite® gelling agent (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite®gelling agent (added after bringing to volume with D-I $H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog, (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite® gelling agent (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l Bacto™-agar solidifying agent (added after bringing to volume with polished D-I $H_2O$), sterilized and cooled to 60° C.

EXAMPLE 8

*Agrobacterium*-Mediated Transformation

For *Agrobacterium*-mediated transformation of maize with an antisense sequence of the Ethylene signaling associated sequence of the present invention, preferably the method of Zhao is employed (U.S. Pat. No. 5,981,840, and PCT Patent Application Publication WO 1998/32326; the contents of which are hereby incorporated by reference). Briefly, immature embryos are isolated from maize and the embryos contacted with a suspension of *Agrobacterium*, where the bacteria are capable of transferring the antisense Ethylene signaling associated sequences to at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants. Plants are monitored and scored for a modulation in meristem development. For instance, alterations of size and appearance of the shoot and floral meristems and/or increased yields of leaves, flowers, and/or fruits.

EXAMPLE 9

Soybean Embryo Transformation

Soybean embryos are bombarded with a plasmid containing an antisense Ethylene signaling associated sequence operably linked to an ubiquitin promoter as follows. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein, et al., (1987) Nature (London) 327:70-73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell, et al., (1985) Nature 313:810-812), the hygromycin phosphotransferase gene from plasmid pJR225 (from E. coli; Gritz, et al., (1983) Gene 25:179-188), and the 3' region of the nopaline synthase gene from the T-DNA of the Ti plasmid of Agrobacterium tumefaciens. The expression cassette comprising an antisense Ethylene signaling associated sequence operably linked to the ubiquitin promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl $CaCl_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

EXAMPLE 10

Sunflower Meristem Tissue Transformation

Sunflower meristem tissues are transformed with an expression cassette containing an antisense Ethylene signaling associated sequences operably linked to a ubiquitin promoter as follows (see also, European Patent Number EP 0 486233, herein incorporated by reference, and Malone-Schoneberg, et al., (1994) Plant Science 103:199-207). Mature sunflower seed (Helianthus annuus L.) are dehulled using a single wheat-head thresher. Seeds are surface sterilized for 30 minutes in a 20% Clorox® bleach solution with the addition of two drops of Tween® 20 per 50 ml of solution. The seeds are rinsed twice with sterile distilled water.

Split embryonic axis explants are prepared by a modification of procedures described by Schrammeijer, et al. (Schrammeijer, et al., (1990) Plant Cell Rep. 9:55-60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige, et al., (1962) Physiol. Plant., 15:473-497), Shepard's vitamin additions (Shepard, (1980) in Emergent Techniques for the Genetic Improvement of Crops (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid ($GA_3$), pH 5.6, and 8 g/l Phytagar (Invitrogen, Carlsbad, Calif.).

The explants are subjected to microprojectile bombardment prior to Agrobacterium treatment (Bidney, et al., (1992) Plant Mol. Biol. 18:301-313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed Agrobacterium tumefaciens strain EHA105 is used in all transformation experiments. A binary plasmid vector comprising the expression cassette that contains the ethylene signaling associated gene operably linked to the ubiquitin promoter is introduced into Agrobacterium strain EHA105 via freeze-thawing as described by Holsters, et al., (1978) Mol. Gen. Genet. 163:181-187. This plasmid further comprises a kanamycin selectable marker gene (i.e, nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The Agrobacterium cells are pelleted and resuspended at a final $OD_{600}$ of 0.5 in an inoculation medium comprised of 12.5 mM MES pH 5.7, 1 gm/l $NH_4Cl$, and 0.3 gm/l $MgSO_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for a modulation in meristem development (i.e., an alteration of size and appearance of shoot and floral meristems).

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% Gelrite® gelling agent, pH 5.6) and grown under conditions described for explant culture. The upper portion of the seedling is removed, a 1 cm vertical slice is made in the hypocotyl, and the transformed shoot inserted into the cut. The entire area is wrapped with Parafilm® flexible film to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by Ethylene signaling associated activity analysis of leaf extracts while transgenic seeds harvested from NPTII-positive $T_o$ plants are identified by Ethylene signaling associated activity analysis of small portions of dry seed cotyledon.

An alternative sunflower transformation protocol allows the recovery of transgenic progeny without the use of chemical selection pressure. Seeds are dehulled and surface-sterilized for 20 minutes in a 20% Clorox® bleach solution with the addition of two to three drops of Tween® 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar (Invitrogen, Carlsbad, Calif.) at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar (Invitrogen, Carlsbad, Calif.)), and then cultured on the medium for 24 hours in the dark.

Approximately 18.8 mg of 1.8 µm tungsten particles are resuspended in 150 µl absolute ethanol. After sonication, 8 µl of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28° C. in a liquid YEP medium (10 g/l yeast extract, 10 g/l Bactopeptone, and 5 g/l NaCl, pH 7.0) in the presence of 50 pg/l kanamycin is resuspended in an inoculation medium (12.5 mM 2-mM 2-(N-morpholino) ethanesulfonic acid, MES, 1 g/l $NH_4Cl$ and 0.3 g/l $MgSO_4$ at pH 5.7) to reach a final concentration of 4.0 at $OD_{600}$. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 µg/ml cefotaxime). The plantlets are cultured on the medium for about two weeks under 16-hour day and 26° C. incubation conditions.

Explants (around 2 cm long) from two weeks of culture in 374C medium are screened for a modulation in meristem development (i.e., an alteration of size and appearance of shoot and floral meristems). After positive explants are identified, those shoots that fail to exhibit modified Ethylene signaling associated activity are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for modified Ethylene signaling associated expression are grafted to Pioneer Hybrid 6440 in vitro-grown sunflower seedling rootstock. The rootstocks are prepared in the following manner. Seeds are dehulled and surface-sterilized for 20 minutes in a 20% Clorox® bleach solution with the addition of two to three drops of Tween® 20 per 100 ml of solution, and are rinsed three times with distilled water. The sterilized seeds are germinated on the filter moistened with water for three days, then they are transferred into 48 medium (half-strength MS salt, 0.5% sucrose, 0.3% Gelrite® gelling agent pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with Parafilm® flexible film. After one week of culture on the medium, grafted plants are transferred to soil. In the first two weeks, they are maintained under high humidity conditions to acclimatize to a greenhouse environment.

EXAMPLE 11

Rice Tissue Transformation

One method for transforming DNA into cells of higher plants that is available to those skilled in the art is high-velocity ballistic bombardment using metal particles coated with the nucleic acid constructs of interest (see, Klein, et al., *Nature* (1987) (London) 327:70-73 and see, U.S. Pat. No. 4,945,050). A Biolistic PDS-1000/He (BioRAD Laboratories, Hercules, Calif.) is used for these complementation experiments. The particle bombardment technique is used to transform the Ethylene signaling associated mutants and wild type rice with DNA fragments The bacterial hygromycin B phosphotransferase (Hpt II) gene from *Streptomyces hygroscopicus* that confers resistance to the antibiotic is used as the selectable marker for rice transformation. In the vector, pML18, the Hpt II gene was engineered with the 35S promoter from Cauliflower Mosaic Virus and the termination and polyadenylation signals from the octopine synthase gene of *Agrobacterium tumefaciens*. pML18 was described in WO 1997/47731, which was published on Dec. 18, 1997, the disclosure of which is hereby incorporated by reference.

Embryogenic callus cultures derived from the scutellum of germinating rice seeds serve as source material for transformation experiments. This material is generated by germinating sterile rice seeds on a callus initiation media (MS salts, Nitsch and Nitsch vitamins, 1.0 mg/l 2,4-D and 10 µM AgNO$_3$) in the dark at 27-28° C. Embryogenic callus proliferating from the scutellum of the embryos is the transferred to CM media (N6 salts, Nitsch and Nitsch vitamins, 1 mg/l 2,4-D, Chu, et al., 1985, *Sci. Sinica* 18: 659-668). Callus cultures are maintained on CM by routine sub-culture at two week intervals and used for transformation within 10 weeks of initiation.

Callus is prepared for transformation by subculturing 0.5-1.0 mm pieces approximately 1 mm apart, arranged in a circular area of about 4 cm in diameter, in the center of a circle of Whatman® #541 paper placed on CM media. The plates with callus are incubated in the dark at 27-28° C. for 3-5 days. Prior to bombardment, the filters with callus are transferred to CM supplemented with 0.25 M mannitol and 0.25 M sorbitol for 3 hr in the dark. The petri dish lids are then left ajar for 20-45 minutes in a sterile hood to allow moisture on tissue to dissipate.

Each genomic DNA fragment is co-precipitated with pML18 containing the selectable marker for rice transformation onto the surface of gold particles. To accomplish this, a total of 10 µg of DNA at a 2:1 ratio of trait:selectable marker DNAs are added to 50 µl aliquot of gold particles that have been resuspended at a concentration of 60 mg ml$^{-1}$. Calcium chloride (50 µl of a 2.5 M solution) and spermidine (20 µl of a 0.1 M solution) are then added to the gold-DNA suspension as the tube is vortexing for 3 min. The gold particles are centrifuged in a microfuge for 1 sec and the supernatant removed. The gold particles are then washed twice with 1 ml of absolute ethanol and then resuspended in 50 µl of absolute ethanol and sonicated (bath sonicator) for one second to disperse the gold particles. The gold suspension is incubated at −70° C. for five minutes and sonicated (bath sonicator) if needed to disperse the particles. Six µl of the DNA-coated gold particles are then loaded onto mylar macrocarrier disks and the ethanol is allowed to evaporate.

At the end of the drying period, a petri dish containing the tissue is placed in the chamber of the PDS-1000/He. The air in the chamber is then evacuated to a vacuum of 28-29 inches Hg. The macrocarrier is accelerated with a helium shock wave using a rupture membrane that bursts when the He pressure in the shock tube reaches 1080-1100 psi. The tissue is placed approximately 8 cm from the stopping screen and the callus is bombarded two times. Two to four plates of tissue are bombarded in this way with the DNA-coated gold particles. Following bombardment, the callus tissue is transferred to CM media without supplemental sorbitol or mannitol.

Within 3-5 days after bombardment the callus tissue is transferred to SM media (CM medium containing 50 mg/l hygromycin). To accomplish this, callus tissue is transferred from plates to sterile 50 ml conical tubes and weighed. Molten top-agar at 40° C. is added using 2.5 ml of top agar/100 mg of callus. Callus clumps are broken into fragments of less than 2 mm diameter by repeated dispensing through a 10 ml pipet. Three ml aliquots of the callus suspension are plated onto fresh SM media and the plates are incubated in the dark for 4 weeks at 27-28° C. After 4 weeks, transgenic callus events are identified, transferred to fresh SM plates and grown for an additional 2 weeks in the dark at 27-28° C.

Growing callus is transferred to RM1 media (MS salts, Nitsch and Nitsch vitamins, 2% sucrose, 3% sorbitol, 0.4% Gelrite® gelling agent +50 ppm hyg B) for 2 weeks in the dark at 25° C. After 2 weeks the callus is transferred to RM2 media (MS salts, Nitsch and Nitsch vitamins, 3% sucrose, 0.4% Gelrite® gelling agent +50 ppm hyg B) and placed under cool white light (~40 µEm$^{-2}$ s$^{-1}$) with a 12 hr photo period at 25° C. and 30-40% humidity. After 2-4 weeks in the light, callus begin to organize, and form shoots. Shoots are removed from surrounding callus/media and gently transferred to RM3 media (½×MS salts, Nitsch and Nitsch vitamins, 1% sucrose +50 ppm hygromycin B) in Phytatray™ disposable plant cell culture vessels (Sigma Chemical Co., St. Louis, Mo.) and incubation is continued using the same conditions as described in the previous step.

Plants are transferred from RM3 to 4" pots containing Scotts MetroMix® 350 growing medium after 2-3 weeks, when sufficient root and shoot growth have occurred. The seed obtained from the transgenic plants is examined for genetic complementation of the Ethylene signaling associated mutation with the wild-type genomic DNA containing the Ethylene signaling associated gene.

EXAMPLE 12

Variants of Ethylene Signaling Associated Sequences

A. Variant Nucleotide Sequences of Ethylene Signaling Associated Proteins that do Not Alter the Encoded Amino Acid Sequence The Ethylene signaling associated nucleotide sequences are used to generate variant nucleotide sequences having the nucleotide sequence of the open reading frame with about 70%, 75%, 80%, 85%, 90% and 95% nucleotide sequence identity when compared to the starting unaltered ORF nucleotide sequence of the corresponding SEQ ID NO. These functional variants are generated using a standard codon table. While the nucleotide sequence of the variants are altered, the amino acid sequence encoded by the open reading frames do not change.

B. Variant Amino Acid Sequences of Ethylene Signaling Associated Polypeptides

Variant amino acid sequences of the Ethylene signaling associated polypeptides are generated. In this example, one amino acid is altered. Specifically, the open reading frames are reviewed to determine the appropriate amino acid alteration. The selection of the amino acid to change is made by consulting the protein alignment (with the other orthologs and other gene family members from various species). An amino acid is selected that is deemed not to be under high selection pressure (not highly conserved) and which is rather easily substituted by an amino acid with similar chemical characteristics (i.e., similar functional side-chain). Using the protein alignment, an appropriate amino acid can be changed. Once the targeted amino acid is identified, the procedure outlined in the following section C is followed. Variants having about 70%, 75%, 80%, 85%, 90% and 95% nucleic acid sequence identity are generated using this method.

C. Additional Variant Amino Acid Sequences of Ethylene Signaling Associated Polypeptides In this example, artificial protein sequences are created having 80%, 85%, 90%, and 95% identity relative to the reference protein sequence. This latter effort requires identifying conserved and variable regions from the alignment and then the judicious application of an amino acid substitutions table. These parts will be discussed in more detail below.

Largely, the determination of which amino acid sequences are altered is made based on the conserved regions among Ethylene signaling associated protein or among the other Ethylene signaling associated polypeptides. Based on the sequence alignment, the various regions of the Ethylene signaling associated polypeptide that can likely be altered are represented in lower case letters, while the conserved regions are represented by capital letters. It is recognized that conservative substitutions can be made in the conserved regions below without altering function. In addition, one of skill will understand that functional variants of the Ethylene signaling associated sequence of the invention can have minor non-conserved amino acid alterations in the conserved domain.

Artificial protein sequences are then created that are different from the original in the intervals of 80-85%, 85-90%, 90-95% and 95-100% identity. Midpoints of these intervals are targeted, with liberal latitude of plus or minus 1%, for example. The amino acids substitutions will be effected by a custom Perl script. The substitution table is provided below in Table 4.

TABLE 4

Substitution Table

| Amino Acid | Strongly Similar and Optimal Substitution | Rank of Order to Change | Comment |
| --- | --- | --- | --- |
| I | L, V | 1 | 50:50 substitution |
| L | I, V | 2 | 50:50 substitution |
| V | I, L | 3 | 50:50 substitution |
| A | G | 4 | |
| G | A | 5 | |
| D | E | 6 | |
| E | D | 7 | |
| W | Y | 8 | |
| Y | W | 9 | |
| S | T | 10 | |
| T | S | 11 | |
| K | R | 12 | |
| R | K | 13 | |
| N | Q | 14 | |
| Q | N | 15 | |
| F | Y | 16 | |
| M | L | 17 | First methionine cannot change |
| H | | Na | No good substitutes |
| C | | Na | No good substitutes |
| P | | Na | No good substitutes |

First, any conserved amino acids in the protein that should not be changed is identified and "marked off" for insulation from the substitution. The start methionine will of course be added to this list automatically. Next, the changes are made. H, C, and P are not changed in any circumstance. The changes will occur with isoleucine first, sweeping N-terminal to C-terminal. Then leucine, and so on down the list until the desired target it reached. Interim number substitutions can be made so as not to cause reversal of changes. The list is ordered 1-17, so start with as many isoleucine changes as needed before leucine, and so on down to methionine. Clearly many amino acids will in this manner not need to be changed. L, I and V will involve a 50:50 substitution of the two alternate optimal substitutions.

The variant amino acid sequences are written as output. Perl script is used to calculate the percent identities. Using this procedure, variants of the Ethylene signaling associated polypeptides are generating having about 80%, 85%, 90% and 95% amino acid identity to the starting unaltered ORF nucleotide sequence of SEQ ID NOS: 1, 3, 5, 7 or 9.

EXAMPLE 13

Transgenic Maize Plants $T_0$ transgenic maize plants containing the Ethylene signaling associated construct under the control of a promoter were generated. These plants were grown in greenhouse conditions, under the FASTCORN system, as detailed in US Patent Application Publication Number 2003/0221212, U.S. patent application Ser. No. 10/367,417.

Each of the plants was analyzed for measurable alteration in one or more of the following characteristics in the following manner:

$T_1$ progeny derived from self fertilization of each $T_o$ plant containing a single copy of each Ethylene signaling associated construct that were found to segregate 1:1 for the transgenic event were analyzed for improved growth rate in low $KNO_3$. Growth was monitored up to anthesis when cumulative plant growth, growth rate and ear weight were determined for transgene positive, transgene null, and non-transformed control events. The distribution of the phenotype of individual plants was compared to the distribution of a control set and to the distribution of all the remaining treatments. Variances for each set were calculated and compared using an F test, comparing the event variance to a non-transgenic control set variance and to the pooled variance of the remaining events in the experiment. The greater the response to $KNO_3$, the greater the variance within an event set and the greater the F value. Positive results will be compared to the distribution of the transgene within the event to make sure the response segregates with the transgene.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

What is claimed is:

1. A recombinant expression cassette comprising a polynucleotide selected from the group consisting of:
   (a) a polynucleotide encoding a polypeptide which has at least 95% sequence identity, as determined by the GAP algorithm under default parameters, to a polypeptide of SEQ ID NO: 4;
   (b) a polynucleotide encoding the polypeptide of SEQ ID NO: 4;
   (c) a polynucleotide of SEQ ID NO: 3;
   (d) a polynucleotide which has at least 95% sequence identity, as determined by the GAP algorithm under default parameters, to the full length of SEQ ID NO: 3;
   (e) a polynucleotide which has at least 95% sequence identity, as determined by the GAP algorithm under default parameters, to the full length of the coding sequence of SEQ ID NO: 3; and
   (f) a polynucleotide which is fully complementary to the polynucleotide of (a), (b), (c), (d), or (e),
   wherein said polynucleotide is operably linked, in sense or anti-sense orientation, to a heterologous promoter.

2. A host cell comprising the recombinant expression cassette of claim 1.

3. A transgenic plant comprising the recombinant expression cassette of claim 1.

4. The transgenic plant of claim 3, wherein said plant is a monocot.

5. The transgenic plant of claim 3, wherein said plant is selected from the group consisting of: maize, soybean, sunflower, sorghum, canola, wheat, alfalfa, cotton, rice, barley and millet.

6. A seed from the transgenic plant of claim 3, wherein said seed comprises the recombinant expression cassette.

7. A method of modulating ethylene response in a plant, comprising:
   (a) introducing into a plant cell a recombinant expression cassette comprising a promoter operably linked to a polynucleotide which has at least 95% sequence identity, as determined by the GAP algorithm under default parameters, to the coding sequence of SEQ ID NO: 3, or to the polynucleotide of SEQ ID NO: 3, or to the complement of either;
   (b) culturing the plant cell under plant cell growing conditions;
   (c) regenerating a plant from said cultured plant cell; and
   (d) inducing expression of said polynucleotide by drought or cold for a time sufficient to modulate the level of EBF1 in said plant.

8. The method of claim 7, wherein the level or activity of EBF1 in aerial portions of the plant is increased relative to a control.

9. The method of claim 7, wherein the plant is selected from the group consisting of: maize, soybean, sorghum, canola, wheat, alfalfa, cotton, rice, barley, millet, peanut and cocoa.

10. The method of claim 7, wherein said plant cell is from a monocot.

11. A transgenic plant produced by the method of claim 7, wherein the plant has decreased ethylene sensitivity when compared to a control plant.

* * * * *

SEQUENCE LISTING

<160> NUMBER OF SEQ ID NOS: 11

<210> SEQ ID NO 1
<211> LENGTH: 2597
<212> TYPE: DNA

```
<213> ORGANISM: Zea mays
<220> FEATURE:
<221> NAME/KEY: CDS
<222> LOCATION: (287)..(2230)

<400> SEQUENCE: 1
ggcgctaccc ccgttcttat ccccacctcg tgcctcccct cctcccccct tcccctctct      60
cgcccctcct ccctccgtct cgtctcccag gtcatggcaa aagctggagc accgggaaaa    120
ataacaagtg ggagataaac aggaagagct aggtgaatac ttggagaaaa aggtccccca    180 cacccccac gcaggtgaat actacaagta gcagtacaag gaagagagcc aatctgcccg     240
tgactgccag tgagttgctc gggtgtggtg gttagttgag gtcacg atg atg gga       295
                                                    Met Met Gly
                                                     1 ggc ggg ctg atg atg gat cag agc gtg gtg ttc cct ggc gtc cac aac     343
Gly Gly Leu Met Met Asp Gln Ser Val Val Phe Pro Gly Val His Asn
        5               10                  15 ttc gtg gat ctc ctg cag cag aac ggc gac aag aac ctg ggc ttc gcc     391
Phe Val Asp Leu Leu Gln Gln Asn Gly Asp Lys Asn Leu Gly Phe Ala
 20              25                  30                  35 tca ctc atg ccg cag acg tcc tcc ggc gac cag tgc gtg atg ggg gag     439
Ser Leu Met Pro Gln Thr Ser Ser Gly Asp Gln Cys Val Met Gly Glu
            40                  45                  50 ggt gat ctc gtg gac cca ccg cca gac agc ttc ccg gac gcc gtg gag     487
Gly Asp Leu Val Asp Pro Pro Pro Asp Ser Phe Pro Asp Ala Val Glu
        55                  60                  65 gac gac agc gat gac gac gtt gag gac atc gag gag ctg gag cgc cgc     535
Asp Asp Ser Asp Asp Asp Val Glu Asp Ile Glu Glu Leu Glu Arg Arg
 70                  75                  80 atg tgg cgc gac cgc atg aag ctg aag cgg ctc agg gag ctg cag cag     583
Met Trp Arg Asp Arg Met Lys Leu Lys Arg Leu Arg Glu Leu Gln Gln
 85                  90                  95 agc cgc ggc aag gat ccc atg gct agc ggt ggg ggc ctg gcc gac ggc     631
Ser Arg Gly Lys Asp Pro Met Ala Ser Gly Gly Gly Leu Ala Asp Gly
100                 105                 110                 115 tca tcc aag cca agg cag tcg cag gag cag gcc cgg cgc aag aag atg     679
Ser Ser Lys Pro Arg Gln Ser Gln Glu Gln Ala Arg Arg Lys Lys Met
                120                 125                 130 tcg cgc gcg cag gac ggc atc ctc aag tac atg ctc aag atg atg gag     727
Ser Arg Ala Gln Asp Gly Ile Leu Lys Tyr Met Leu Lys Met Met Glu
            135                 140                 145 gtg tgc cgc gcg cag ggg ttt gtg tac ggg atc att ccg gag aag ggc     775
Val Cys Arg Ala Gln Gly Phe Val Tyr Gly Ile Ile Pro Glu Lys Gly
        150                 155                 160 aag ccg gtg agc ggc gcc tcc gac aac ctc cgt gcc tgg tgg aag gag     823
Lys Pro Val Ser Gly Ala Ser Asp Asn Leu Arg Ala Trp Trp Lys Glu
165                 170                 175 aag gtc cgc ttc gac cgc aac ggc ccg gcc gcc atc gcc aag tat cag     871
Lys Val Arg Phe Asp Arg Asn Gly Pro Ala Ala Ile Ala Lys Tyr Gln
180                 185                 190                 195 gcc gac aac gcc gtc ccg ggc gcc gag aat gag ctc gcc tcg ggc gct     919
Ala Asp Asn Ala Val Pro Gly Ala Glu Asn Glu Leu Ala Ser Gly Ala
                200                 205                 210 gcc agc cct cat tcc ttg cag gag ctg cag gac acc aca ctc ggc tcg     967
Ala Ser Pro His Ser Leu Gln Glu Leu Gln Asp Thr Thr Leu Gly Ser
            215                 220                 225 ctg ctc tca gca ctc atg cag cac tgc gac ccc cca cag cgg cgc tac    1015
Leu Leu Ser Ala Leu Met Gln His Cys Asp Pro Pro Gln Arg Arg Tyr
        230                 235                 240
```

-continued

| | | |
|---|---|---|
| ccg ctg gag aag ggc gtt cct cca ccg tgg tgg cct acc ggc gac gag<br>Pro Leu Glu Lys Gly Val Pro Pro Pro Trp Trp Pro Thr Gly Asp Glu<br>245 250 255 | 1063 | |
| gag tgg tgg ccg gag ctt ggc att ccc aag gac cag ggc cca cct ccc<br>Glu Trp Trp Pro Glu Leu Gly Ile Pro Lys Asp Gln Gly Pro Pro Pro<br>260 265 270 275 | 1111 | |
| tac aag aag ccc cat gac ctt aag aag gcc tgg aag gtg agc gtc ctc<br>Tyr Lys Lys Pro His Asp Leu Lys Lys Ala Trp Lys Val Ser Val Leu<br>280 285 290 | 1159 | |
| acc gct gtc atc aag cac atg tca cca gac ata gag aag acc cga cgc<br>Thr Ala Val Ile Lys His Met Ser Pro Asp Ile Glu Lys Thr Arg Arg<br>295 300 305 | 1207 | |
| ctc gtt cgc cag tcc aag tgc ctc cag gac aag atg act gcc aag gag<br>Leu Val Arg Gln Ser Lys Cys Leu Gln Asp Lys Met Thr Ala Lys Glu<br>310 315 320 | 1255 | |
| atc tcg acc tgg ctg gcg gtc gtc aag cag gaa gag gag ctg tac ctg<br>Ile Ser Thr Trp Leu Ala Val Val Lys Gln Glu Glu Glu Leu Tyr Leu<br>325 330 335 | 1303 | |
| aag atg cac cct ggc gca cgc ccg ccg gca tcc act ggt ggc atc gcc<br>Lys Met His Pro Gly Ala Arg Pro Pro Ala Ser Thr Gly Gly Ile Ala<br>340 345 350 355 | 1351 | |
| agt gcc ata tct ttc aac acc acc tca agc gag tac gac gtg gac atc<br>Ser Ala Ile Ser Phe Asn Thr Thr Ser Ser Glu Tyr Asp Val Asp Ile<br>360 365 370 | 1399 | |
| gtt gat gag tgc aag ggg gat gag gct ggc aac cag aag aca gca gtc<br>Val Asp Glu Cys Lys Gly Asp Glu Ala Gly Asn Gln Lys Thr Ala Val<br>375 380 385 | 1447 | |
| act gac cca acc tcc ttc aac ctt ggt gcg gct atc cta agt gac aag<br>Thr Asp Pro Thr Ser Phe Asn Leu Gly Ala Ala Ile Leu Ser Asp Lys<br>390 395 400 | 1495 | |
| ttc ctc atg ccg acg ccg atg aag gag gag acc gct gac gtc gag ttc<br>Phe Leu Met Pro Thr Pro Met Lys Glu Glu Thr Ala Asp Val Glu Phe<br>405 410 415 | 1543 | |
| atc cag aag agg aac gcc ccc gct cct gct gag cca gag cta atg cta<br>Ile Gln Lys Arg Asn Ala Pro Ala Pro Ala Glu Pro Glu Leu Met Leu<br>420 425 430 435 | 1591 | |
| aac aac cgg gtg tac acc tgc aac aac gtc cag tgc ccg cac agt gac<br>Asn Asn Arg Val Tyr Thr Cys Asn Asn Val Gln Cys Pro His Ser Asp<br>440 445 450 | 1639 | |
| tac agc tat gga ttc ctt gac cgg aat gcc cgc aac agc cac cag tac<br>Tyr Ser Tyr Gly Phe Leu Asp Arg Asn Ala Arg Asn Ser His Gln Tyr<br>455 460 465 | 1687 | |
| acc tgt aag tac aac gat ccg atc act cag agc gcc gag aac aag cct<br>Thr Cys Lys Tyr Asn Asp Pro Ile Thr Gln Ser Ala Glu Asn Lys Pro<br>470 475 480 | 1735 | |
| ctg cca gca ccg ccg caa cca caa gcc ttc cag ccg gcc ttc agc caa<br>Leu Pro Ala Pro Pro Gln Pro Gln Ala Phe Gln Pro Ala Phe Ser Gln<br>485 490 495 | 1783 | |
| gcc aat cag gca gcg aac aat ctg gac ttc agc ctg cct atg gac ggg<br>Ala Asn Gln Ala Ala Asn Asn Leu Asp Phe Ser Leu Pro Met Asp Gly<br>500 505 510 515 | 1831 | |
| cag agg tcc atc gcc gag ctg atg aac atg tac gac acc aac ttc atg<br>Gln Arg Ser Ile Ala Glu Leu Met Asn Met Tyr Asp Thr Asn Phe Met<br>520 525 530 | 1879 | |
| acg agc aag acc atg agc agt agt gac agc gtc acc atc atg gag agg<br>Thr Ser Lys Thr Met Ser Ser Ser Asp Ser Val Thr Ile Met Glu Arg<br>535 540 545 | 1927 | |
| ccg aac gcg atg ccc cag agg atc cag atg gac gag ggc ttc ttc gga<br>Pro Asn Ala Met Pro Gln Arg Ile Gln Met Asp Glu Gly Phe Phe Gly<br>550 555 560 | 1975 | |

```
cag ggc aac gga gtc ttc gac gac gtc aat agc atg atg cag caa caa    2023
Gln Gly Asn Gly Val Phe Asp Asp Val Asn Ser Met Met Gln Gln Gln
565                 570                 575 cag cag cag gca cca ccc gtg gtg cag cag cag cag cag cag ttc        2071
Gln Gln Gln Ala Pro Pro Val Val Gln Gln Gln Gln Gln Gln Phe
580                 585                 590                 595 ttc atc cgc gac gac acg cca ttc atg agc cag atg ggc gac atc acc    2119
Phe Ile Arg Asp Asp Thr Pro Phe Met Ser Gln Met Gly Asp Ile Thr
                600                 605                 610 agc acg gcg gag ttc agg ttc ggc tct ggt ttc aac atg tct agc acc    2167
Ser Thr Ala Glu Phe Arg Phe Gly Ser Gly Phe Asn Met Ser Ser Thr
            615                 620                 625 gcc gcc gcc gct gat tac cca ggc gcg gcg cag aag aac gac ggg acc    2215
Ala Ala Ala Ala Asp Tyr Pro Gly Ala Ala Gln Lys Asn Asp Gly Thr
        630                 635                 640 aat tgg ttc tac tga agaataaaac ttgtagggct cctcgttata agcttcggat    2270
Asn Trp Phe Tyr
    645 tcctccatgg atctcccaag ttgtcaagtc ttataggtct tcgttatata ggttttgcag  2330 tagctgcaag acggctggaa cctggaactg gtttatactt gtatgtccgg ccagccataa  2390 acctctctta tttgcaaact taatgttatt cctagcttta agttgttagt ctcagtctgc  2450 tgtccatgta tatggctgtt aaaatgcttg tgcttgtttc tgtactacct gctgtttggt  2510 gtctgaatga agtgttttct tcagtggttc aaaaaaaaaa aaaaaaaaa aaaaaaaaa    2570 aaaaaaaaaa aaaaaaaaaa aaaaaag                                     2597

<210> SEQ ID NO 2
<211> LENGTH: 647
<212> TYPE: PRT
<213> ORGANISM: Zea mays

<400> SEQUENCE: 2

Met Met Gly Gly Gly Leu Met Met Asp Gln Ser Val Val Phe Pro Gly
1               5                   10                  15

Val His Asn Phe Val Asp Leu Leu Gln Gln Asn Gly Asp Lys Asn Leu
            20                  25                  30

Gly Phe Ala Ser Leu Met Pro Gln Thr Ser Ser Gly Asp Gln Cys Val
        35                  40                  45

Met Gly Glu Gly Asp Leu Val Asp Pro Pro Asp Ser Phe Pro Asp
    50                  55                  60

Ala Val Glu Asp Asp Ser Asp Asp Val Glu Asp Ile Glu Glu Leu
65                  70                  75                  80

Glu Arg Arg Met Trp Arg Asp Arg Met Lys Leu Lys Arg Leu Arg Glu
                85                  90                  95

Leu Gln Gln Ser Arg Gly Lys Asp Pro Met Ala Ser Gly Gly Leu
            100                 105                 110

Ala Asp Gly Ser Ser Lys Pro Arg Gln Ser Gln Glu Gln Ala Arg Arg
        115                 120                 125

Lys Lys Met Ser Arg Ala Gln Asp Gly Ile Leu Lys Tyr Met Leu Lys
    130                 135                 140

Met Met Glu Val Cys Arg Ala Gln Gly Phe Val Tyr Gly Ile Ile Pro
145                 150                 155                 160

Glu Lys Gly Lys Pro Val Ser Gly Ala Ser Asp Asn Leu Arg Ala Trp
                165                 170                 175

Trp Lys Glu Lys Val Arg Phe Asp Arg Asn Gly Pro Ala Ala Ile Ala
```

```
                180                 185                 190
Lys Tyr Gln Ala Asp Asn Ala Val Pro Gly Ala Glu Asn Glu Leu Ala
            195                 200                 205

Ser Gly Ala Ala Ser Pro His Ser Leu Gln Glu Leu Gln Asp Thr Thr
            210                 215                 220

Leu Gly Ser Leu Leu Ser Ala Leu Met Gln His Cys Asp Pro Pro Gln
225                 230                 235                 240

Arg Arg Tyr Pro Leu Glu Lys Gly Val Pro Pro Trp Trp Pro Thr
                245                 250                 255

Gly Asp Glu Glu Trp Trp Pro Glu Leu Gly Ile Pro Lys Asp Gln Gly
                260                 265                 270

Pro Pro Pro Tyr Lys Lys Pro His Asp Leu Lys Lys Ala Trp Lys Val
            275                 280                 285

Ser Val Leu Thr Ala Val Ile Lys His Met Ser Pro Asp Ile Glu Lys
            290                 295                 300

Thr Arg Arg Leu Val Arg Gln Ser Lys Cys Leu Gln Asp Lys Met Thr
305                 310                 315                 320

Ala Lys Glu Ile Ser Thr Trp Leu Ala Val Val Lys Gln Glu Glu Glu
                325                 330                 335

Leu Tyr Leu Lys Met His Pro Gly Ala Arg Pro Pro Ala Ser Thr Gly
                340                 345                 350

Gly Ile Ala Ser Ala Ile Ser Phe Asn Thr Thr Ser Ser Glu Tyr Asp
            355                 360                 365

Val Asp Ile Val Asp Glu Cys Lys Gly Asp Glu Ala Gly Asn Gln Lys
            370                 375                 380

Thr Ala Val Thr Asp Pro Thr Ser Phe Asn Leu Gly Ala Ala Ile Leu
385                 390                 395                 400

Ser Asp Lys Phe Leu Met Pro Thr Pro Met Lys Glu Glu Thr Ala Asp
                405                 410                 415

Val Glu Phe Ile Gln Lys Arg Asn Ala Pro Ala Pro Ala Glu Pro Glu
                420                 425                 430

Leu Met Leu Asn Asn Arg Val Tyr Thr Cys Asn Asn Val Gln Cys Pro
            435                 440                 445

His Ser Asp Tyr Ser Tyr Gly Phe Leu Asp Arg Asn Ala Arg Asn Ser
            450                 455                 460

His Gln Tyr Thr Cys Lys Tyr Asn Asp Pro Ile Thr Gln Ser Ala Glu
465                 470                 475                 480

Asn Lys Pro Leu Pro Ala Pro Gln Pro Gln Ala Phe Gln Pro Ala
                485                 490                 495

Phe Ser Gln Ala Asn Gln Ala Ala Asn Asn Leu Asp Phe Ser Leu Pro
            500                 505                 510

Met Asp Gly Gln Arg Ser Ile Ala Glu Leu Met Asn Met Tyr Asp Thr
            515                 520                 525

Asn Phe Met Thr Ser Lys Thr Met Ser Ser Ser Asp Ser Val Thr Ile
            530                 535                 540

Met Glu Arg Pro Asn Ala Met Pro Gln Arg Ile Gln Met Asp Glu Gly
545                 550                 555                 560

Phe Phe Gly Gln Gly Asn Gly Val Phe Asp Asp Val Asn Ser Met Met
                565                 570                 575

Gln Gln Gln Gln Gln Gln Ala Pro Pro Val Val Gln Gln Gln Gln Gln
            580                 585                 590

Gln Gln Phe Phe Ile Arg Asp Asp Thr Pro Phe Met Ser Gln Met Gly
            595                 600                 605
```

Asp Ile Thr Ser Thr Ala Glu Phe Arg Phe Gly Ser Gly Phe Asn Met
         610                 615                 620

Ser Ser Thr Ala Ala Ala Ala Asp Tyr Pro Gly Ala Ala Gln Lys Asn
625                 630                 635                 640

Asp Gly Thr Asn Trp Phe Tyr
            645

<210> SEQ ID NO 3
<211> LENGTH: 4159
<212> TYPE: DNA
<213> ORGANISM: Zea mays
<220> FEATURE:
<221> NAME/KEY: CDS
<222> LOCATION: (1465)..(3408)

<400> SEQUENCE: 3

```
cggcgactcc accgccgccg ggaggatccg cgcctccacc tctgccccca ccggccggat      60
ccgcgcctcc tccactgccc ccaccggccg gatccgcgcc tccaccaccg ccggcgggat     120
ccgccactgc gccgccaccg gtgtctccag ccccgtcgcg cacctcatcc ccgtcgagcc     180
cctactctcc acctccgcat gatgaggtcc tcggcgcgcc cagtgcagtg gcgagctgtt     240
catcgcagga ggccacggcg gcgagctctg atgggcggat ccagctacag gagggaaagg     300
tgttcgtgca gctcggcgcg aaggagcagc gggaccctac gtcctggatc tgcgacaccg     360 ggccacgaa ccacatgacg gggtctcggg cggcgttcgc ggatctggac acggcggtgt     420
ctgggtcggt gtggttcggc gatgactcca tggcggagat tgaagggcgc gggaccgtgc     480
tgttcaagtg caagaatggc gagcatcgct ctttcaccgg cgtttactac atcccgcgac     540
tcacggcgaa tatcgtgagc ctcggccagt tggaggaggc cgactacgac gtccacctcc     600
ggcgcggtgg catggagatt cgggagcctg aggggcgact gctggcaagg atcccacgcg     660
caggcaaccg gctgtatgtg ctcaacgtcg acgtggcacg gccggtgtgc ctggcagcgc     720
gcggcgaaga aagtgcctgg cggtggcatg ccaggctcgg ccacatcaac atgctggcgc     780
tgaggaagat ggcgcgggag gagctcgttc gtggactgcc atccatcgag caggtggacc     840
aactttgtga ggagaaaatt ggaattctgc cattatcaaa cctaggattc gctcaaatgc     900
cattatgaaa acacgcttcg ttaatacgcc attctcaaac actagcttac agacaaaatg     960
ccatttaggg ggttatttaa aagatcaacg ttttactgt gctgtgagca attgatcgga    1020 cagtttacc cctagaacca aaagcgccat tcactagcat ccacctttc ttatcctctg     1080 tctctcgctc gtatctcctc tctggacgaa cagaaaggtt accagcagca ccacgccaag    1140 atctccctt ggcgggccaa aaccgacggc gagctccacc ggcgttggtc agctcccttc    1200
tcttcgccgt tttattttcc tcccaggtcg gtctcctcca ctatccccac agaggttccc    1260
cttctccttc cttccttcgc ttcctttttt tccctgtcg ccggcggcga tagggtcccg    1320
tttttcttgc ttcggcgggc tgtaaatgct tccggtcctc tccggcggtc cagatccggc    1380
ggtgaccgtg ctcctgttcg ttctcctggt cttgattcga gtgggagggg aagggggtccc    1440 ttcggtcttg ggaaactcga agac atg cct gcg ctc tac gct tat tac gga       1491
                            Met Pro Ala Leu Tyr Ala Tyr Tyr Gly
                              1               5 gat gac ggg tgc ctc gtc tcg gcg ccg gct gag ctg gcc gga ctc ttc      1539
Asp Asp Gly Cys Leu Val Ser Ala Pro Ala Glu Leu Ala Gly Leu Phe
 10                  15                  20                  25 tgc cgc ggc gcc gtg cag cag cgg aag cgc acg cta gtg acc gcg tcc      1587
Cys Arg Gly Ala Val Gln Gln Arg Lys Arg Thr Leu Val Thr Ala Ser
```

-continued

|     |     |     |     | 30  |     |     |     |     | 35  |     |     |     |     | 40  |     |      |
| --- | --- | --- | --- | --- | --- | --- | --- | --- | --- | --- | --- | --- | --- | --- | --- | ---- |
| gcg | gtc | gcc | gcc | gcg | gcc | gcc | gag | tgc | gtg | agg | gcg | gcc | aag | aag | cag | 1635 |
| Ala | Val | Ala | Ala | Ala | Ala | Ala | Glu | Cys | Val | Arg | Ala | Ala | Lys | Lys | Gln |      |
|     |     |     |     | 45  |     |     |     |     | 50  |     |     |     |     | 55  |     |      |
| agg | cag | ctg | ccg | ctg | ccg | tcg | ctc | gac | gcg | ctc | cca | gac | gag | tgc | ctc | 1683 |
| Arg | Gln | Leu | Pro | Leu | Pro | Ser | Leu | Asp | Ala | Leu | Pro | Asp | Glu | Cys | Leu |      |
|     |     |     |     | 60  |     |     |     |     | 65  |     |     |     |     | 70  |     |      |
| ttc | gag | atc | ctg | cgc | cgc | gtg | ccc | ggc | cgt | cgc | ggc | gcc | gct | gcc | tgc | 1731 |
| Phe | Glu | Ile | Leu | Arg | Arg | Val | Pro | Gly | Arg | Arg | Gly | Ala | Ala | Ala | Cys |      |
|     |     |     |     | 75  |     |     |     |     | 80  |     |     |     |     | 85  |     |      |
| gtc | tcc | cgc | cgc | tgg | ctc | gcg | ctc | ctc | ggc | agc | atc | cgg | gtc | tcc | gag | 1779 |
| Val | Ser | Arg | Arg | Trp | Leu | Ala | Leu | Leu | Gly | Ser | Ile | Arg | Val | Ser | Glu |      |
| 90  |     |     |     |     | 95  |     |     |     |     | 100 |     |     |     |     | 105 |      |
| ttc | ggc | cag | gcc | gcc | gcg | gcg | gcg | gac | acc | ccg | tcg | ctg | ccg | gac | ctg | 1827 |
| Phe | Gly | Gln | Ala | Ala | Ala | Ala | Ala | Asp | Thr | Pro | Ser | Leu | Pro | Asp | Leu |      |
|     |     |     |     | 110 |     |     |     |     | 115 |     |     |     |     | 120 |     |      |
| aac | gag | gag | ttc | gtc | atg | gag | gag | gat | aag | gag | gag | gtc | ccc | gcg | gat | 1875 |
| Asn | Glu | Glu | Phe | Val | Met | Glu | Glu | Asp | Lys | Glu | Glu | Val | Pro | Ala | Asp |      |
|     |     |     |     | 125 |     |     |     |     | 130 |     |     |     |     | 135 |     |      |
| cgg | tgc | gtt | gac | agg | gtc | ctc | gag | ggc | aag | gag | gcc | acc | gac | gtc | cgc | 1923 |
| Arg | Cys | Val | Asp | Arg | Val | Leu | Glu | Gly | Lys | Glu | Ala | Thr | Asp | Val | Arg |      |
|     |     |     |     | 140 |     |     |     |     | 145 |     |     |     |     | 150 |     |      |
| ctg | gcc | gcc | atg | gcc | gtc | gtc | gcc | gga | tcc | tgt | ggc | ggg | ctg | gag | aag | 1971 |
| Leu | Ala | Ala | Met | Ala | Val | Val | Ala | Gly | Ser | Cys | Gly | Gly | Leu | Glu | Lys |      |
| 155 |     |     |     |     | 160 |     |     |     |     | 165 |     |     |     |     |     |      |
| ctc | tcc | gtc | cgt | gga | agc | cac | ccg | gcc | cgt | ggc | gtc | aca | gac | caa | gga | 2019 |
| Leu | Ser | Val | Arg | Gly | Ser | His | Pro | Ala | Arg | Gly | Val | Thr | Asp | Gln | Gly |      |
| 170 |     |     |     |     | 175 |     |     |     |     | 180 |     |     |     |     | 185 |      |
| ctc | tcg | gcg | gtt | gca | cgc | ggc | agc | ccc | aac | ctc | agc | tcg | ctc | gcg | ctc | 2067 |
| Leu | Ser | Ala | Val | Ala | Arg | Gly | Ser | Pro | Asn | Leu | Ser | Ser | Leu | Ala | Leu |      |
|     |     |     |     | 190 |     |     |     |     | 195 |     |     |     |     | 200 |     |      |
| tgg | gac | gtg | cct | ctt | atc | acc | gac | gct | gga | ctt | gtg | gag | atc | gcc | gcc | 2115 |
| Trp | Asp | Val | Pro | Leu | Ile | Thr | Asp | Ala | Gly | Leu | Val | Glu | Ile | Ala | Ala |      |
|     |     |     |     | 205 |     |     |     |     | 210 |     |     |     |     | 215 |     |      |
| ggg | tgc | ccc | ttg | ctg | gag | cgt | ctg | gat | att | tct | cga | tgc | ccc | ctc | atc | 2163 |
| Gly | Cys | Pro | Leu | Leu | Glu | Arg | Leu | Asp | Ile | Ser | Arg | Cys | Pro | Leu | Ile |      |
|     |     |     |     | 220 |     |     |     |     | 225 |     |     |     |     | 230 |     |      |
| aca | gac | aag | ggc | ctc | gcc | gct | ttt | gcg | cag | ggg | tgc | ccc | gac | ttg | gtg | 2211 |
| Thr | Asp | Lys | Gly | Leu | Ala | Ala | Phe | Ala | Gln | Gly | Cys | Pro | Asp | Leu | Val |      |
|     |     |     |     | 235 |     |     |     |     | 240 |     |     |     |     | 245 |     |      |
| tct | ctg | acc | atc | gag | gca | tgc | tct | agt | gtt | ggc | gat | gag | ggc | ctg | agg | 2259 |
| Ser | Leu | Thr | Ile | Glu | Ala | Cys | Ser | Ser | Val | Gly | Asp | Glu | Gly | Leu | Arg |      |
| 250 |     |     |     |     | 255 |     |     |     |     | 260 |     |     |     |     | 265 |      |
| gca | att | ggc | cgc | agc | tgc | atg | aaa | ctg | caa | gct | ggg | aac | atc | aag | aac | 2307 |
| Ala | Ile | Gly | Arg | Ser | Cys | Met | Lys | Leu | Gln | Ala | Gly | Asn | Ile | Lys | Asn |      |
|     |     |     |     | 270 |     |     |     |     | 275 |     |     |     |     | 280 |     |      |
| tgc | cct | ctt | ggt | ggt | gac | caa | ggc | atc | tcc | agc | ctg | gtg | tgc | tct | gcc | 2355 |
| Cys | Pro | Leu | Gly | Gly | Asp | Gln | Gly | Ile | Ser | Ser | Leu | Val | Cys | Ser | Ala |      |
|     |     |     |     | 285 |     |     |     |     | 290 |     |     |     |     | 295 |     |      |
| acc | gct | gcg | ctt | aca | aag | atc | cgg | ctc | cag | gga | ctg | aac | ata | act | gat | 2403 |
| Thr | Ala | Ala | Leu | Thr | Lys | Ile | Arg | Leu | Gln | Gly | Leu | Asn | Ile | Thr | Asp |      |
|     |     |     |     | 300 |     |     |     |     | 305 |     |     |     |     | 310 |     |      |
| gct | tca | ctt | gct | gtg | att | gga | tac | tac | ggg | aaa | gcc | atc | act | gac | ctt | 2451 |
| Ala | Ser | Leu | Ala | Val | Ile | Gly | Tyr | Tyr | Gly | Lys | Ala | Ile | Thr | Asp | Leu |      |
|     |     |     |     | 315 |     |     |     |     | 320 |     |     |     |     | 325 |     |      |
| aca | ctt | act | cgt | ctc | gct | act | gtt | ggt | gag | agg | ggt | ttc | tgg | gtg | atg | 2499 |
| Thr | Leu | Thr | Arg | Leu | Ala | Thr | Val | Gly | Glu | Arg | Gly | Phe | Trp | Val | Met |      |
| 330 |     |     |     |     | 335 |     |     |     |     | 340 |     |     |     |     | 345 |      |
| gct | aat | gct | gct | ggc | ctg | cag | aat | ctc | agg | tgc | atg | agt | ggt | acc | tct | 2547 |

```
Ala Asn Ala Ala Gly Leu Gln Asn Leu Arg Cys Met Ser Gly Thr Ser
            350                 355                 360 tgc cct gga gtc acc gat ctt gcg ctc gct tct att gcc aag ttc tgc     2595
Cys Pro Gly Val Thr Asp Leu Ala Leu Ala Ser Ile Ala Lys Phe Cys
        365                 370                 375 cca aac ttg aag aag ctt tac ctc agg aag tgc gga cat gtg tca gat     2643
Pro Asn Leu Lys Lys Leu Tyr Leu Arg Lys Cys Gly His Val Ser Asp
            380                 385                 390 gct ggc ctc aag gcc ttc aca gaa tca gca aag gtg ttt gag aac tta     2691
Ala Gly Leu Lys Ala Phe Thr Glu Ser Ala Lys Val Phe Glu Asn Leu
        395                 400                 405 cag ctt gag gaa tgc aac cgg gtt tct ctt gtc ggt att ctt gct ttc     2739
Gln Leu Glu Glu Cys Asn Arg Val Ser Leu Val Gly Ile Leu Ala Phe
410                 415                 420                 425 ctc aac tgc aga gag aag ttc agg gct cta tcg ttg gtg aaa tgc atg     2787
Leu Asn Cys Arg Glu Lys Phe Arg Ala Leu Ser Leu Val Lys Cys Met
                430                 435                 440 ggg atc aag gat atc tgc tct gcg cct gca caa ctt cct ttt tgc cga     2835
Gly Ile Lys Asp Ile Cys Ser Ala Pro Ala Gln Leu Pro Phe Cys Arg
            445                 450                 455 tca ctt cgt ttc ctt aca atc aag gat tgc cca ggt ttc acc gat gca     2883
Ser Leu Arg Phe Leu Thr Ile Lys Asp Cys Pro Gly Phe Thr Asp Ala
        460                 465                 470 agc ttg gct gcg gtg ggg atg att tgc cct cag ttg gag cag gtt gac     2931
Ser Leu Ala Ala Val Gly Met Ile Cys Pro Gln Leu Glu Gln Val Asp
    475                 480                 485 ctg agt ggt ctt ggt gag gtc act gac aac ggg ctt ctt cca ttg atc     2979
Leu Ser Gly Leu Gly Glu Val Thr Asp Asn Gly Leu Leu Pro Leu Ile
490                 495                 500                 505 cag tct tct gaa tct ggt ctg atc aag gtt gac ttg agt ggt tgc aag     3027
Gln Ser Ser Glu Ser Gly Leu Ile Lys Val Asp Leu Ser Gly Cys Lys
                510                 515                 520 aac atc aca gat gtg gct gtc tcc tct ctg gtg aag cga cat gga aaa     3075
Asn Ile Thr Asp Val Ala Val Ser Ser Leu Val Lys Arg His Gly Lys
            525                 530                 535 tct ctg aag aaa gtc agc ctt gag ggt tgc agc aag ata aca gat gct     3123
Ser Leu Lys Lys Val Ser Leu Glu Gly Cys Ser Lys Ile Thr Asp Ala
        540                 545                 550 agc ctc ttc acc atg tct gag agc tgc acc gag ctt gcc gag ctt gat     3171
Ser Leu Phe Thr Met Ser Glu Ser Cys Thr Glu Leu Ala Glu Leu Asp
    555                 560                 565 ctt tca aac tgc atg gtt agt gac tat ggt gtt gcc atg ctg gca tct     3219
Leu Ser Asn Cys Met Val Ser Asp Tyr Gly Val Ala Met Leu Ala Ser
570                 575                 580                 585 gca agg cac ctc aag ctc cgt gtt ctc tca ctg tca ggc tgc tct aag     3267
Ala Arg His Leu Lys Leu Arg Val Leu Ser Leu Ser Gly Cys Ser Lys
                590                 595                 600 gtt act cag aag agc gtg ccg ttc ttg ggc aac ctt ggc cag tct ata     3315
Val Thr Gln Lys Ser Val Pro Phe Leu Gly Asn Leu Gly Gln Ser Ile
            605                 610                 615 gag ggc ctc aat ctt cag ttc tgc aac atg att ggc aac cac aac atc     3363
Glu Gly Leu Asn Leu Gln Phe Cys Asn Met Ile Gly Asn His Asn Ile
        620                 625                 630 gca tcc ctg gag aaa aag ctc tgg tgg tgc gac atc ctt gca tag         3408
Ala Ser Leu Glu Lys Lys Leu Trp Trp Cys Asp Ile Leu Ala
    635                 640                 645 gcagcagaca agatgagcca ttgctggaag gggctcatgt ctagtctact gggagccacc   3468
tccagatgca gatatacgac cttagcagta gcacaaccag acggtcttca ggttttggc    3528
```

```
tcgcatgccg gtcattatgg tgggcttcca cattgttcaa ggaccagttg tttaggggg      3588 cgctttctag cggagtgctc gttttcaca gatcacctct caggggttt atctgtttt        3648 tgagcctcgg ctgccatcac tggcatcctg cccctagatc cagacactgg tccttgccct    3708
tacagtcata agttctttt aggttgccat agtgtccagg tcctctttcg ttttactgtt     3768
gcaggcgttg gtgatccatt gacagctctg gactatcaca gttctaactc aactgccaga    3828
tgctgctggt gctggagcgt ctgtggactt gtgcggtgtg tttggttgtc atgtttagag    3888
tcttgatgtg ttgtgtgtgt gtgctgttct ccatggtgtg taagggtcat gtagggttgc    3948
atctttttta cagtctctct gggatgcctg gtgttcatgg tgatcgtggc cattgcgagg    4008
cgcttactag aagccttgcc ttgacagcct tgtatggttg ttttttttg ccagatccct     4068 gttttacag gcagattgtt gagtgctgta agcttggcga ccctctatga ataaatgaaa     4128
tatgtgttta ggtcgaaaaa aaaaaaaaaa a                                   4159
```

<210> SEQ ID NO 4
<211> LENGTH: 647
<212> TYPE: PRT
<213> ORGANISM: Zea mays

<400> SEQUENCE: 4

```
Met Pro Ala Leu Tyr Ala Tyr Tyr Gly Asp Asp Gly Cys Leu Val Ser
1               5                   10                  15

Ala Pro Ala Glu Leu Ala Gly Leu Phe Cys Arg Gly Ala Val Gln Gln
                20                  25                  30

Arg Lys Arg Thr Leu Val Thr Ala Ser Ala Val Ala Ala Ala Ala Ala
            35                  40                  45

Glu Cys Val Arg Ala Ala Lys Lys Gln Arg Gln Leu Pro Leu Pro Ser
        50                  55                  60

Leu Asp Ala Leu Pro Asp Glu Cys Leu Phe Glu Ile Leu Arg Arg Val
65                  70                  75                  80

Pro Gly Arg Arg Gly Ala Ala Cys Val Ser Arg Arg Trp Leu Ala
                85                  90                  95

Leu Leu Gly Ser Ile Arg Val Ser Glu Phe Gly Gln Ala Ala Ala Ala
                100                 105                 110

Ala Asp Thr Pro Ser Leu Pro Asp Leu Asn Glu Glu Phe Val Met Glu
            115                 120                 125

Glu Asp Lys Glu Glu Val Pro Ala Asp Arg Cys Val Asp Arg Val Leu
        130                 135                 140

Glu Gly Lys Glu Ala Thr Asp Val Arg Leu Ala Ala Met Ala Val Val
145                 150                 155                 160

Ala Gly Ser Cys Gly Gly Leu Glu Lys Leu Ser Val Arg Gly Ser His
                165                 170                 175

Pro Ala Arg Gly Val Thr Asp Gln Gly Leu Ser Ala Val Ala Arg Gly
            180                 185                 190

Ser Pro Asn Leu Ser Ser Leu Ala Leu Trp Asp Val Pro Leu Ile Thr
        195                 200                 205

Asp Ala Gly Leu Val Glu Ile Ala Ala Gly Cys Pro Leu Leu Glu Arg
    210                 215                 220

Leu Asp Ile Ser Arg Cys Pro Leu Ile Thr Asp Lys Gly Leu Ala Ala
225                 230                 235                 240

Phe Ala Gln Gly Cys Pro Asp Leu Val Ser Leu Thr Ile Glu Ala Cys
                245                 250                 255

Ser Ser Val Gly Asp Glu Gly Leu Arg Ala Ile Gly Arg Ser Cys Met
```

```
                260                 265                 270
Lys Leu Gln Ala Gly Asn Ile Lys Asn Cys Pro Leu Gly Gly Asp Gln
            275                 280                 285
Gly Ile Ser Ser Leu Val Cys Ser Ala Thr Ala Leu Thr Lys Ile
        290                 295                 300
Arg Leu Gln Gly Leu Asn Ile Thr Asp Ala Ser Leu Ala Val Ile Gly
305                 310                 315                 320
Tyr Tyr Gly Lys Ala Ile Thr Asp Leu Thr Leu Thr Arg Leu Ala Thr
                325                 330                 335
Val Gly Glu Arg Gly Phe Trp Val Met Ala Asn Ala Ala Gly Leu Gln
            340                 345                 350
Asn Leu Arg Cys Met Ser Gly Thr Ser Cys Pro Gly Val Thr Asp Leu
        355                 360                 365
Ala Leu Ala Ser Ile Ala Lys Phe Cys Pro Asn Leu Lys Lys Leu Tyr
        370                 375                 380
Leu Arg Lys Cys Gly His Val Ser Asp Ala Gly Leu Lys Ala Phe Thr
385                 390                 395                 400
Glu Ser Ala Lys Val Phe Glu Asn Leu Gln Leu Glu Glu Cys Asn Arg
                405                 410                 415
Val Ser Leu Val Gly Ile Leu Ala Phe Leu Asn Cys Arg Glu Lys Phe
            420                 425                 430
Arg Ala Leu Ser Leu Val Lys Cys Met Gly Ile Lys Asp Ile Cys Ser
        435                 440                 445
Ala Pro Ala Gln Leu Pro Phe Cys Arg Ser Leu Arg Phe Leu Thr Ile
        450                 455                 460
Lys Asp Cys Pro Gly Phe Thr Asp Ala Ser Leu Ala Ala Val Gly Met
465                 470                 475                 480
Ile Cys Pro Gln Leu Glu Gln Val Asp Leu Ser Gly Leu Gly Glu Val
                485                 490                 495
Thr Asp Asn Gly Leu Leu Pro Leu Ile Gln Ser Ser Glu Ser Gly Leu
            500                 505                 510
Ile Lys Val Asp Leu Ser Gly Cys Lys Asn Ile Thr Asp Val Ala Val
        515                 520                 525
Ser Ser Leu Val Lys Arg His Gly Lys Ser Leu Lys Lys Val Ser Leu
        530                 535                 540
Glu Gly Cys Ser Lys Ile Thr Asp Ala Ser Leu Phe Thr Met Ser Glu
545                 550                 555                 560
Ser Cys Thr Glu Leu Ala Glu Leu Asp Leu Ser Asn Cys Met Val Ser
                565                 570                 575
Asp Tyr Gly Val Ala Met Leu Ala Ser Ala Arg His Leu Lys Leu Arg
            580                 585                 590
Val Leu Ser Leu Ser Gly Cys Ser Lys Val Thr Gln Lys Ser Val Pro
        595                 600                 605
Phe Leu Gly Asn Leu Gly Gln Ser Ile Glu Gly Leu Asn Leu Gln Phe
        610                 615                 620
Cys Asn Met Ile Gly Asn His Asn Ile Ala Ser Leu Glu Lys Lys Leu
625                 630                 635                 640
Trp Trp Cys Asp Ile Leu Ala
                645

<210> SEQ ID NO 5
<211> LENGTH: 2693
<212> TYPE: DNA
<213> ORGANISM: Zea mays
```

```
<220> FEATURE:
<221> NAME/KEY: CDS
<222> LOCATION: (97)..(1938)

<400> SEQUENCE: 5
tcttctaaat ccgccttct tcgtttcgat ttttccggcg ttctgggagc aagcttcggc      60
ttcatcgacg gcgttcttgg tcttttgcgg ctcgac atg tct ccg ttc cag gga     114
                                        Met Ser Pro Phe Gln Gly
                                         1               5 tac aga ggc gat gcg gtt ctc tcc ggc gtc cgg tcg cgg aag cgc gtg    162
Tyr Arg Gly Asp Ala Val Leu Ser Gly Val Arg Ser Arg Lys Arg Val
             10                  15                  20 ttc gcg acg gcg gcc gcg gag ccc gtg acg gcg gcc ccc aag agg cag    210
Phe Ala Thr Ala Ala Ala Glu Pro Val Thr Ala Ala Pro Lys Arg Gln
         25                  30                  35 aag cgc ggg gat gag atg ccc ctg gac gcg ctg ccg gac gag tgc ctc    258
Lys Arg Gly Asp Glu Met Pro Leu Asp Ala Leu Pro Asp Glu Cys Leu
 40                  45                  50 ttc gag gtc ctg cgc cgc gtg cag ggc acc cgc gcg cgc tgc gcg tcg    306
Phe Glu Val Leu Arg Arg Val Gln Gly Thr Arg Ala Arg Cys Ala Ser
 55                  60                  65                  70 gcc tgc gtc tcc cgc cgc tgg ctc gcg ctc ctc gcc ggc atc cgc gcc    354
Ala Cys Val Ser Arg Arg Trp Leu Ala Leu Leu Ala Gly Ile Arg Ala
             75                  80                  85 tct gag gcc gtg ctg gcc ccg gcc gcc ccc gcc gtg ccg gac ctc aac    402
Ser Glu Ala Val Leu Ala Pro Ala Ala Pro Ala Val Pro Asp Leu Asn
         90                  95                 100 cag gag tac ctc agc gag gac gac gag gcc gat ctg atg gac ctg gac    450
Gln Glu Tyr Leu Ser Glu Asp Asp Glu Ala Asp Leu Met Asp Leu Asp
     105                 110                 115 ggc gac gcc cgc gag agg acc ctc gag ggc atg gag gcc acg gac gcg    498
Gly Asp Ala Arg Glu Arg Thr Leu Glu Gly Met Glu Ala Thr Asp Ala
120                 125                 130 cgc ctc acg gcg gcg gcc gtg gcc ggc cgt ctg gct gcc gtc tcc gtc    546
Arg Leu Thr Ala Ala Ala Val Ala Gly Arg Leu Ala Ala Val Ser Val
135                 140                 145                 150 cgc ggg agc cac ccc cgc ggc tgc cca gag ctc cgc tcc ctt acc ctg    594
Arg Gly Ser His Pro Arg Gly Cys Pro Glu Leu Arg Ser Leu Thr Leu
             155                 160                 165 tgg gat gtc ccg cag gtg acg gac gcc ggg ctc gcc gag gtc gcg gcc    642
Trp Asp Val Pro Gln Val Thr Asp Ala Gly Leu Ala Glu Val Ala Ala
         170                 175                 180 gag tgc cac tcg ctg gag cgg ctt gac atc tct ggc tgc cct atg atc    690
Glu Cys His Ser Leu Glu Arg Leu Asp Ile Ser Gly Cys Pro Met Ile
     185                 190                 195 acg gac aag ggc ctc gcc gcg gtt gct cag ggt tgc ccg gaa ctg aag    738
Thr Asp Lys Gly Leu Ala Ala Val Ala Gln Gly Cys Pro Glu Leu Lys
200                 205                 210 tcg ctc acc atc gag gga tgc tcc ggt gtg gcc aac gag ggt ctc aag    786
Ser Leu Thr Ile Glu Gly Cys Ser Gly Val Ala Asn Glu Gly Leu Lys
215                 220                 225                 230 gct gta ggt cgt ttc tgc gcc aag cta cag gcg gtt agc atc aag aat    834
Ala Val Gly Arg Phe Cys Ala Lys Leu Gln Ala Val Ser Ile Lys Asn
             235                 240                 245 tgc gca ctc gtc gat gac cag ggt gtg tct ggc ctc gtc tgc tct gcg    882
Cys Ala Leu Val Asp Asp Gln Gly Val Ser Gly Leu Val Cys Ser Ala
         250                 255                 260 acc gcc tct tcg ttg aca aag gtc cgg ctt cag ggt ttg aac att act    930
Thr Ala Ser Ser Leu Thr Lys Val Arg Leu Gln Gly Leu Asn Ile Thr
     265                 270                 275
```

-continued

| | | |
|---|---|---|
| gat gct tcc ctt gct gtg atc ggg tac tac ggg aag tca atc aaa gac<br>Asp Ala Ser Leu Ala Val Ile Gly Tyr Tyr Gly Lys Ser Ile Lys Asp<br>280                        285                         290 | | 978 |
| ctg acc ctt tct cgc ctc cct gct gtc ggt gag agg gga ttc tgg gtg<br>Leu Thr Leu Ser Arg Leu Pro Ala Val Gly Glu Arg Gly Phe Trp Val<br>295                        300                        305                         310 | | 1026 |
| atg gcc aat gcc ctg ggc ctg cag aag ctc agg cga atg act gtt gtc<br>Met Ala Asn Ala Leu Gly Leu Gln Lys Leu Arg Arg Met Thr Val Val<br>                        315                         320                         325 | | 1074 |
| tcc tgc ccg gga ctc acg gat ctt gct ctt gca tct gtc gcc aag ttc<br>Ser Cys Pro Gly Leu Thr Asp Leu Ala Leu Ala Ser Val Ala Lys Phe<br>                        330                        335                        340 | | 1122 |
| agc cca agt ttg agg ctt gtt aac ctc aag agg tgc agc aag gtc tca<br>Ser Pro Ser Leu Arg Leu Val Asn Leu Lys Arg Cys Ser Lys Val Ser<br>     345                        350                        355 | | 1170 |
| gat gga tgt ctc aag gaa ttt gca gaa tca tct aag gtc ctg gag aac<br>Asp Gly Cys Leu Lys Glu Phe Ala Glu Ser Ser Lys Val Leu Glu Asn<br>360                        365                        370 | | 1218 |
| ttg cag atc gag gaa tgc agc agg gtt act ctt acg ggc att ctt gcg<br>Leu Gln Ile Glu Glu Cys Ser Arg Val Thr Leu Thr Gly Ile Leu Ala<br>375                        380                        385                        390 | | 1266 |
| ttc ctc ctc aac tgc ggc cca aag ttt aag tct ctc tcc ctg tcc aag<br>Phe Leu Leu Asn Cys Gly Pro Lys Phe Lys Ser Leu Ser Leu Ser Lys<br>                        395                        400                        405 | | 1314 |
| tgc gtc ggg atc aag gac atc tgc tcc gca cct gca caa ctt ccg gta<br>Cys Val Gly Ile Lys Asp Ile Cys Ser Ala Pro Ala Gln Leu Pro Val<br>                        410                        415                        420 | | 1362 |
| tgc aaa tca cta cgt tcc ctg gcc atc aag gat tgc cca ggc ttc acc<br>Cys Lys Ser Leu Arg Ser Leu Ala Ile Lys Asp Cys Pro Gly Phe Thr<br>     425                        430                        435 | | 1410 |
| gac gcc agc ctt gcc gtg gtg ggc atg atc tgc cct cag ctg gag aac<br>Asp Ala Ser Leu Ala Val Val Gly Met Ile Cys Pro Gln Leu Glu Asn<br>440                        445                        450 | | 1458 |
| gtc aat ttg agt ggc ctt agt gca gtc acc gac agc ggc ttc ctt cca<br>Val Asn Leu Ser Gly Leu Ser Ala Val Thr Asp Ser Gly Phe Leu Pro<br>455                        460                        465                        470 | | 1506 |
| ctg ata aag agt tca aac agt ggg ctg gtc aac gtc gat ttg aac ggt<br>Leu Ile Lys Ser Ser Asn Ser Gly Leu Val Asn Val Asp Leu Asn Gly<br>                        475                        480                        485 | | 1554 |
| tgc gag aat ctc acg gat gca gct gtt tcc gcc ttg gtt aag gcc cac<br>Cys Glu Asn Leu Thr Asp Ala Ala Val Ser Ala Leu Val Lys Ala His<br>                        490                        495                        500 | | 1602 |
| ggc gct tcc ctt gcg cac ctc agt ctc gag gga tgc agc aag att acc<br>Gly Ala Ser Leu Ala His Leu Ser Leu Glu Gly Cys Ser Lys Ile Thr<br>     505                        510                        515 | | 1650 |
| gat gca agc ctg ttc gcc atc tct gag agc tgc agc cag ctc gcc gag<br>Asp Ala Ser Leu Phe Ala Ile Ser Glu Ser Cys Ser Gln Leu Ala Glu<br>520                        525                        530 | | 1698 |
| ctc gac ctt tcg aac tgc atg gtc agc gac tac ggc gtc gcg gtc ttg<br>Leu Asp Leu Ser Asn Cys Met Val Ser Asp Tyr Gly Val Ala Val Leu<br>535                        540                        545                        550 | | 1746 |
| gca gcg gca aag cag ctc agg ctg cgc gtc ctc tcg ctg tcc ggc tgt<br>Ala Ala Ala Lys Gln Leu Arg Leu Arg Val Leu Ser Leu Ser Gly Cys<br>                        555                        560                        565 | | 1794 |
| atg aag gtc acc cag aag agc gtc cct ttc cta ggc agc atg tct tcg<br>Met Lys Val Thr Gln Lys Ser Val Pro Phe Leu Gly Ser Met Ser Ser<br>                        570                        575                        580 | | 1842 |
| tcc ttg gag ggg ctg aat ctc cag ttc aac ttc att ggc aac cac aac<br>Ser Leu Glu Gly Leu Asn Leu Gln Phe Asn Phe Ile Gly Asn His Asn | | 1890 |

```
                585                 590                 595
atc gcg tcc ctg gag aag cag ctc tgg cgg tgc gac atc ctt gct tag      1938
Ile Ala Ser Leu Glu Lys Gln Leu Trp Arg Cys Asp Ile Leu Ala
        600                 605                 610 aggaacacgg cggttattcg tcgctggaga tgctaggtca accttctccg gatgcaaata    1998
cacgaccgaa gcagtagttt agtactcaag tctatgctct gtagttgagt ctggtttccg    2058
gctcgtgttt gtgtcatggt gggtcttctg ttcgtcgtcg tcctagggcc agttgttttc    2118 cgagggggt gttttttcc ggaagctcat ttttttgcag gaatcctcct gtgaggatct      2178
ctgtttcttg agcctttggc agccattgct atggcactct gccccctcc ataccaaact     2238 aagccctcgt gatcagtcat tccaccatgc agtttctctc aagtcagtgt ttgaaaccca    2298
agtatctctg tcaagtgcgc gttcttttcc ggtattcctg gttatagagc tgcagacatc    2358
aacactcttt tgattgcaat gtagcaagt ccagttgtcg gtggttgcaa ctctccatcc     2418
agaattgcag acatcaacat tcttttgagt gcaattgtat caagtcccaa ctgtcggtgt    2478
ctccattcag agaaacttag ctccatgtct ttgatgtctg ggtgcctgca atcttgccga    2538
gtgcagtgtg ttgttggcca tgggcggaag tgtcggtatg gtttgcctat gtgcttgggg   2598
atctggcctt tgcaaggttc attctacaga gccttttgcc ttcacagccc tgtgtggttg    2658
tttttcttct gcagagacct gattttgaca ggcag                               2693
```

<210> SEQ ID NO 6
<211> LENGTH: 613
<212> TYPE: PRT
<213> ORGANISM: Zea mays

<400> SEQUENCE: 6

```
Met Ser Pro Phe Gln Gly Tyr Arg Gly Asp Ala Val Leu Ser Gly Val
1               5                   10                  15

Arg Ser Arg Lys Arg Val Phe Ala Thr Ala Ala Ala Glu Pro Val Thr
                20                  25                  30

Ala Ala Pro Lys Arg Gln Lys Arg Gly Asp Glu Met Pro Leu Asp Ala
            35                  40                  45

Leu Pro Asp Glu Cys Leu Phe Glu Val Leu Arg Val Gln Gly Thr
    50                  55                  60

Arg Ala Arg Cys Ala Ser Ala Cys Val Ser Arg Arg Trp Leu Ala Leu
65                  70                  75                  80

Leu Ala Gly Ile Arg Ala Ser Glu Ala Val Leu Ala Pro Ala Ala Pro
                85                  90                  95

Ala Val Pro Asp Leu Asn Gln Glu Tyr Leu Ser Glu Asp Glu Ala
            100                 105                 110

Asp Leu Met Asp Leu Asp Gly Asp Ala Arg Glu Arg Thr Leu Glu Gly
        115                 120                 125

Met Glu Ala Thr Asp Ala Arg Leu Thr Ala Ala Val Ala Gly Arg
    130                 135                 140

Leu Ala Ala Val Ser Val Arg Gly Ser His Pro Arg Gly Cys Pro Glu
145                 150                 155                 160

Leu Arg Ser Leu Thr Leu Trp Asp Val Pro Gln Val Thr Asp Ala Gly
                165                 170                 175

Leu Ala Glu Val Ala Ala Glu Cys His Ser Leu Glu Arg Leu Asp Ile
            180                 185                 190

Ser Gly Cys Pro Met Ile Thr Asp Lys Gly Leu Ala Ala Val Ala Gln
        195                 200                 205
```

```
Gly Cys Pro Glu Leu Lys Ser Leu Thr Ile Glu Gly Cys Ser Gly Val
    210                 215                 220
Ala Asn Glu Gly Leu Lys Ala Val Gly Arg Phe Cys Ala Lys Leu Gln
225                 230                 235                 240
Ala Val Ser Ile Lys Asn Cys Ala Leu Val Asp Asp Gln Gly Val Ser
                245                 250                 255
Gly Leu Val Cys Ser Ala Thr Ala Ser Ser Leu Thr Lys Val Arg Leu
                260                 265                 270
Gln Gly Leu Asn Ile Thr Asp Ala Ser Leu Ala Val Ile Gly Tyr Tyr
            275                 280                 285
Gly Lys Ser Ile Lys Asp Leu Thr Leu Ser Arg Leu Pro Ala Val Gly
290                 295                 300
Glu Arg Gly Phe Trp Val Met Ala Asn Ala Leu Gly Leu Gln Lys Leu
305                 310                 315                 320
Arg Arg Met Thr Val Val Ser Cys Pro Gly Leu Thr Asp Leu Ala Leu
                325                 330                 335
Ala Ser Val Ala Lys Phe Ser Pro Ser Leu Arg Leu Val Asn Leu Lys
                340                 345                 350
Arg Cys Ser Lys Val Ser Asp Gly Cys Leu Lys Glu Phe Ala Glu Ser
                355                 360                 365
Ser Lys Val Leu Glu Asn Leu Gln Ile Glu Glu Cys Ser Arg Val Thr
    370                 375                 380
Leu Thr Gly Ile Leu Ala Phe Leu Leu Asn Cys Gly Pro Lys Phe Lys
385                 390                 395                 400
Ser Leu Ser Leu Ser Lys Cys Val Gly Ile Lys Asp Ile Cys Ser Ala
                405                 410                 415
Pro Ala Gln Leu Pro Val Cys Lys Ser Leu Arg Ser Leu Ala Ile Lys
                420                 425                 430
Asp Cys Pro Gly Phe Thr Asp Ala Ser Leu Ala Val Val Gly Met Ile
                435                 440                 445
Cys Pro Gln Leu Glu Asn Val Asn Leu Ser Gly Leu Ser Ala Val Thr
    450                 455                 460
Asp Ser Gly Phe Leu Pro Leu Ile Lys Ser Ser Asn Ser Gly Leu Val
465                 470                 475                 480
Asn Val Asp Leu Asn Gly Cys Glu Asn Leu Thr Asp Ala Ala Val Ser
                485                 490                 495
Ala Leu Val Lys Ala His Gly Ala Ser Leu Ala His Leu Ser Leu Glu
                500                 505                 510
Gly Cys Ser Lys Ile Thr Asp Ala Ser Leu Phe Ala Ile Ser Glu Ser
                515                 520                 525
Cys Ser Gln Leu Ala Glu Leu Asp Leu Ser Asn Cys Met Val Ser Asp
    530                 535                 540
Tyr Gly Val Ala Val Leu Ala Ala Ala Lys Gln Leu Arg Leu Arg Val
545                 550                 555                 560
Leu Ser Leu Ser Gly Cys Met Lys Val Thr Gln Lys Ser Val Pro Phe
                565                 570                 575
Leu Gly Ser Met Ser Ser Ser Leu Glu Gly Leu Asn Leu Gln Phe Asn
                580                 585                 590
Phe Ile Gly Asn His Asn Ile Ala Ser Leu Glu Lys Gln Leu Trp Arg
            595                 600                 605
Cys Asp Ile Leu Ala
    610
```

-continued

```
<210> SEQ ID NO 7
<211> LENGTH: 3715
<212> TYPE: DNA
<213> ORGANISM: Zea mays
<220> FEATURE:
<221> NAME/KEY: CDS
<222> LOCATION: (118)..(3090)

<400> SEQUENCE: 7
caaggaggca gcaaccagcg cacgccactg cggcgctagg agctcgcaga agcgccgccc      60
cacgagaggg agtccagagc aaggaagaga tccggtggca gagtaggtcg gtcggag        117 atg gga gta ccg gcg ttc tac cgg tgg ctg gcg gac cgc tac ccg ctg      165
Met Gly Val Pro Ala Phe Tyr Arg Trp Leu Ala Asp Arg Tyr Pro Leu
1               5                   10                  15 acg gtg tct gac gcg gag gag gag gag ccc gtg gag ctc gag ccc ggc      213
Thr Val Ser Asp Ala Glu Glu Glu Glu Pro Val Glu Leu Glu Pro Gly
            20                  25                  30 gcc ttc gtc ccc gtt gac ctc cgc cgc ccc aat ccc aac ggc ctc gag      261
Ala Phe Val Pro Val Asp Leu Arg Arg Pro Asn Pro Asn Gly Leu Glu
        35                  40                  45 ttt gac aac ctc tac ctc gac atg aat ggt atc atc cac cca tgc ttc      309
Phe Asp Asn Leu Tyr Leu Asp Met Asn Gly Ile Ile His Pro Cys Phe
    50                  55                  60 cac ccc gag ggc cgg ccg gcg ccc acc acc tac gac gag gtg ttc aag      357
His Pro Glu Gly Arg Pro Ala Pro Thr Thr Tyr Asp Glu Val Phe Lys
65                  70                  75                  80 tcg att ttt gat tac atc gac cac ctc ttc ggc ctc atc cgc ccc agg      405
Ser Ile Phe Asp Tyr Ile Asp His Leu Phe Gly Leu Ile Arg Pro Arg
                85                  90                  95 aag ctt ctc tac atg gcc att gat ggt gtt gct cca agg gca aaa atg      453
Lys Leu Leu Tyr Met Ala Ile Asp Gly Val Ala Pro Arg Ala Lys Met
            100                 105                 110 aac cag cag agg tcc agg cga ttc cgg gct gct aag gac gcg gct gat      501
Asn Gln Gln Arg Ser Arg Arg Phe Arg Ala Ala Lys Asp Ala Ala Asp
        115                 120                 125 gcg gca gcg gag gaa gag agg ctg agg aag gag ttt gag gca gag ggt      549
Ala Ala Ala Glu Glu Glu Arg Leu Arg Lys Glu Phe Glu Ala Glu Gly
    130                 135                 140 agg act cta gcc cag aaa gag aag tcg gag gca att gac tcc aat gtc      597
Arg Thr Leu Ala Gln Lys Glu Lys Ser Glu Ala Ile Asp Ser Asn Val
145                 150                 155                 160 att act cca ggg acg gag ttc atg ttt gta cta tct acg gcg ctt cag      645
Ile Thr Pro Gly Thr Glu Phe Met Phe Val Leu Ser Thr Ala Leu Gln
                165                 170                 175 tac tac ata cag ctg agg ctg aat cac acg ctt gga tgg cag tct gta      693
Tyr Tyr Ile Gln Leu Arg Leu Asn His Thr Leu Gly Trp Gln Ser Val
            180                 185                 190 aag ata ata ctg tct gat tcc aat gtc cct gga gag gga gag cac aaa      741
Lys Ile Ile Leu Ser Asp Ser Asn Val Pro Gly Glu Gly Glu His Lys
        195                 200                 205 att atg tca tac atc cgc ctg cag cgc aat ctt cct ggc ttt gat ccc      789
Ile Met Ser Tyr Ile Arg Leu Gln Arg Asn Leu Pro Gly Phe Asp Pro
    210                 215                 220 aat aca cgc cat tgc tta tat ggc ctg gac gct gat ttg att atg ctt      837
Asn Thr Arg His Cys Leu Tyr Gly Leu Asp Ala Asp Leu Ile Met Leu
225                 230                 235                 240 gct cta gcg act cac gag gtt cac ttc tca att tta aga gag gtg atc      885
Ala Leu Ala Thr His Glu Val His Phe Ser Ile Leu Arg Glu Val Ile
                245                 250                 255 tcc atg cca ggg caa cat gaa aaa tgt ttt ctt tgt ggt caa gtt ggg      933
```

```
            Ser Met Pro Gly Gln His Glu Lys Cys Phe Leu Cys Gly Gln Val Gly
                        260             265                 270 cat ttg gct gct gaa tgc aga ggt cct agt cag cct gat aat tct gtg        981
His Leu Ala Ala Glu Cys Arg Gly Pro Ser Gln Pro Asp Asn Ser Val
            275                 280                 285 gag cta cct cct att cat aaa aag aaa tac cag ttt ctt aac ata tgg       1029
Glu Leu Pro Pro Ile His Lys Lys Lys Tyr Gln Phe Leu Asn Ile Trp
            290                 295                 300 gtg ttg cgt gaa tac ctg gca aag gat ttg gaa att ata gat gct ccc       1077
Val Leu Arg Glu Tyr Leu Ala Lys Asp Leu Glu Ile Ile Asp Ala Pro
305                 310                 315                 320 ttc aag ata aac ttt gaa cgt ctt att gat gat ttt gtg ttt atg tgt       1125
Phe Lys Ile Asn Phe Glu Arg Leu Ile Asp Asp Phe Val Phe Met Cys
                325                 330                 335 ttc ttt gtt ggc aat gac ttt ctt cct cat atg cca act ttg gaa att       1173
Phe Phe Val Gly Asn Asp Phe Leu Pro His Met Pro Thr Leu Glu Ile
            340                 345                 350 cgt gag ggt gcc att aat ctt ctc atg agt atc tac agg tcg gag ttc       1221
Arg Glu Gly Ala Ile Asn Leu Leu Met Ser Ile Tyr Arg Ser Glu Phe
            355                 360                 365 aca tca atg ggt ggt tac cta act gat gtg ggt gag gtt ata ttg gac       1269
Thr Ser Met Gly Gly Tyr Leu Thr Asp Val Gly Glu Val Ile Leu Asp
370                 375                 380 cga gtg gaa cat ttc atc cag tct gtt gcg gtc aat gaa gaa cag att       1317
Arg Val Glu His Phe Ile Gln Ser Val Ala Val Asn Glu Glu Gln Ile
385                 390                 395                 400 ttc cag aaa cgg gca cgc att caa cag gca cgt gag aat aat gaa gag       1365
Phe Gln Lys Arg Ala Arg Ile Gln Gln Ala Arg Glu Asn Asn Glu Glu
                405                 410                 415 aaa cat aaa atg cag aga gag aat tct gag gag gat caa tat gtg gat       1413
Lys His Lys Met Gln Arg Glu Asn Ser Glu Glu Asp Gln Tyr Val Asp
            420                 425                 430 aag gtg aag tta gga gag cca gga tac agg gag cgt tat tat gct gat       1461
Lys Val Lys Leu Gly Glu Pro Gly Tyr Arg Glu Arg Tyr Tyr Ala Asp
            435                 440                 445 aag ttt aaa gaa gag gca gaa tca aaa ccc att gtt caa gtt cgg aga       1509
Lys Phe Lys Glu Glu Ala Glu Ser Lys Pro Ile Val Gln Val Arg Arg
450                 455                 460 gat gtt gtc cag aaa tac gtg gaa ggt ctt tgt tgg gtt atg aga tac       1557
Asp Val Val Gln Lys Tyr Val Glu Gly Leu Cys Trp Val Met Arg Tyr
465                 470                 475                 480 tac tat caa ggt gtt tgt tca tgg cag tgg ttt tat ccc tat cat tat       1605
Tyr Tyr Gln Gly Val Cys Ser Trp Gln Trp Phe Tyr Pro Tyr His Tyr
                485                 490                 495 gcg cct ttc gca tct gat cta aaa ggc ttg gct gaa ttg gaa ata acc       1653
Ala Pro Phe Ala Ser Asp Leu Lys Gly Leu Ala Glu Leu Glu Ile Thr
            500                 505                 510 ttt ttt ttg ggt caa cct ttc aag cca ttt gat caa cta atg gga acc       1701
Phe Phe Leu Gly Gln Pro Phe Lys Pro Phe Asp Gln Leu Met Gly Thr
            515                 520                 525 cta cca gct gca agc tcc aat gca ctg cca aaa tac tat ggg gat ttg       1749
Leu Pro Ala Ala Ser Ser Asn Ala Leu Pro Lys Tyr Tyr Gly Asp Leu
            530                 535                 540 atg agt gat cca gat tca ccg ttg aag tct ttc tac cca aaa gat ttt       1797
Met Ser Asp Pro Asp Ser Pro Leu Lys Ser Phe Tyr Pro Lys Asp Phe
545                 550                 555                 560 gag ata gac atg aat ggg aaa cgt ttt gca tgg cag ggt gtt gca aaa       1845
Glu Ile Asp Met Asn Gly Lys Arg Phe Ala Trp Gln Gly Val Ala Lys
                565                 570                 575
```

```
ttg cct ttt att gat gaa agg cgt ctg ctt gcg gaa aca aga aaa ctt    1893
Leu Pro Phe Ile Asp Glu Arg Arg Leu Leu Ala Glu Thr Arg Lys Leu
            580                 585                 590 gaa gat act ttg aca gaa gaa gag aaa ttc agg aat agg act atg ctt    1941
Glu Asp Thr Leu Thr Glu Glu Glu Lys Phe Arg Asn Arg Thr Met Leu
        595                 600                 605 gac ata att tac gtt aga gat act cat cca ttg atc act cag att atc    1989
Asp Ile Ile Tyr Val Arg Asp Thr His Pro Leu Ile Thr Gln Ile Ile
    610                 615                 620 ttc ctg tat cag aac tat tac cat cta tca aga aca gac cct tat gtt    2037
Phe Leu Tyr Gln Asn Tyr Tyr His Leu Ser Arg Thr Asp Pro Tyr Val
625                 630                 635                 640 att ccc att gag cct gct gct agt ggt gga atg aat gga ttc cta tgt    2085
Ile Pro Ile Glu Pro Ala Ala Ser Gly Gly Met Asn Gly Phe Leu Cys
            645                 650                 655 tta tct gaa agg aac tgg tat agt gtc act gtc act tct cca gtt aag    2133
Leu Ser Glu Arg Asn Trp Tyr Ser Val Thr Val Thr Ser Pro Val Lys
        660                 665                 670 ggg ttc aat ggc att gct cag aac aga gtt ttg aat gct gcc tat ctc    2181
Gly Phe Asn Gly Ile Ala Gln Asn Arg Val Leu Asn Ala Ala Tyr Leu
    675                 680                 685 aat cct cag tat cac aaa cac atc cca gag cct cca gcg ggg gtc atc    2229
Asn Pro Gln Tyr His Lys His Ile Pro Glu Pro Pro Ala Gly Val Ile
690                 695                 700 ata cct gcg aag ata ctg aag cct agt gat ttc aaa ccc ttt cct gtg    2277
Ile Pro Ala Lys Ile Leu Lys Pro Ser Asp Phe Lys Pro Phe Pro Val
705                 710                 715                 720 ttg tgg cat caa gat aat agt cgt cga caa gta aga gaa agg cct cag    2325
Leu Trp His Gln Asp Asn Ser Arg Arg Gln Val Arg Glu Arg Pro Gln
            725                 730                 735 gtt tct gga gcc ctg tcc ggt tct ctc tta gga gaa gct gca cac cga    2373
Val Ser Gly Ala Leu Ser Gly Ser Leu Leu Gly Glu Ala Ala His Arg
        740                 745                 750 ctg gtg aaa aac tcc ctc cag atc aga tct ggc aat gct gct ggg tta    2421
Leu Val Lys Asn Ser Leu Gln Ile Arg Ser Gly Asn Ala Ala Gly Leu
    755                 760                 765 ctt tat atg cca tac aga ggt gca ccc tat ggc cct gga aac aga cca    2469
Leu Tyr Met Pro Tyr Arg Gly Ala Pro Tyr Gly Pro Gly Asn Arg Pro
770                 775                 780 agg cct gct ggg cca ttg ggg tat gag agg ggt ttt gtg gat aat cca    2517
Arg Pro Ala Gly Pro Leu Gly Tyr Glu Arg Gly Phe Val Asp Asn Pro
785                 790                 795                 800 tac cat gca cac atg tct aga agt gtt cca aac cct cac gct caa ttc    2565
Tyr His Ala His Met Ser Arg Ser Val Pro Asn Pro His Ala Gln Phe
            805                 810                 815 ttt ggt gat tct caa gct aac aga cag ccc atg cgg ata cta gaa cgg    2613
Phe Gly Asp Ser Gln Ala Asn Arg Gln Pro Met Arg Ile Leu Glu Arg
        820                 825                 830 cca gac tcc cga agt cat gat gct ggt atc cgt gca tca atg tct aaa    2661
Pro Asp Ser Arg Ser His Asp Ala Gly Ile Arg Ala Ser Met Ser Lys
    835                 840                 845 ctg aca atc caa gaa ggg cca agg cct cat caa aat aac agg atg cag    2709
Leu Thr Ile Gln Glu Gly Pro Arg Pro His Gln Asn Asn Arg Met Gln
850                 855                 860 aat tcc ggg tac tgg ccc aat caa cca cat cct act cac ttt act gga    2757
Asn Ser Gly Tyr Trp Pro Asn Gln Pro His Pro Thr His Phe Thr Gly
865                 870                 875                 880 ccc cca gcc cag cgg cct atg cag aac atc agt ttt aca cct cag cga    2805
Pro Pro Ala Gln Arg Pro Met Gln Asn Ile Ser Phe Thr Pro Gln Arg
            885                 890                 895
```

```
cct ttc caa acc ggg gga ttt ccg cag cag aga cct gta aat ggg gct    2853
Pro Phe Gln Thr Gly Gly Phe Pro Gln Gln Arg Pro Val Asn Gly Ala
        900                 905                 910 cca cca cca tta cct ccc agt aac tgg att ggt aag caa cca agt gga    2901
Pro Pro Pro Leu Pro Pro Ser Asn Trp Ile Gly Lys Gln Pro Ser Gly
    915                 920                 925 tgc cac atg agt gta tca cct gca aaa ctc gat cca agg aca gct cca    2949
Cys His Met Ser Val Ser Pro Ala Lys Leu Asp Pro Arg Thr Ala Pro
930                 935                 940 gac aga cag ccc aag cag gat aac cca aga tct caa cag gat aag agg    2997
Asp Arg Gln Pro Lys Gln Asp Asn Pro Arg Ser Gln Gln Asp Lys Arg
945                 950                 955                 960 cag cag gcg acc aag gta tac cgt gtc aaa act caa gct act aat gtt    3045
Gln Gln Ala Thr Lys Val Tyr Arg Val Lys Thr Gln Ala Thr Asn Val
            965                 970                 975 aat ggt ttg tca gag cca ggt aaa cag gaa gaa cct gaa ggg taa        3090
Asn Gly Leu Ser Glu Pro Gly Lys Gln Glu Glu Pro Glu Gly
        980                 985                 990 ctgggttgct gcaaatccac acgccaagtt taatgtgcgt ggagagaata cgctggctct    3150
tggtgatagc agcagagggt ttccatgtat ccctcccata atttaccttt cgatgttgaa    3210
ttgtttgttg tattacccgg aaaggagtcg gctaaatttt aggtcagggg atttagacac    3270
agcttttgtt tagttgatag acatggtat gggcattcac tgcttgttgt aaagctgtta     3330
gttggatagc tgaaactgtt ttgtgctggc tgactgctgc atattcaaca tagacccgtg    3390
cggaggctgg ctcaactgcc ctgctcctgc tctatctcat ggaagttggg ggcagatgtg    3450
cttgtggtct tcaaactgag cagtttgtgt ctctgagaaa ggaggaagca ttccgaattt    3510
ttcattgtac cgttgaacca agttgagtct ttaacactga aaagaacatg ttcctctcga    3570
gcttaacgag tgccataatt aggacatgga ataatatata tattttctt  ttctgggatg    3630 caaaaaaaaa aaaaaaaaaa aaaaaaaaaa aaaaaaaaaa aaaaaaaaaa aaaaaaaaaa    3690
aaaaaaaaaa aaaaaaaaaa aaaaa                                         3715

<210> SEQ ID NO 8
<211> LENGTH: 990
<212> TYPE: PRT
<213> ORGANISM: Zea mays

<400> SEQUENCE: 8

Met Gly Val Pro Ala Phe Tyr Arg Trp Leu Ala Asp Arg Tyr Pro Leu
1               5                   10                  15

Thr Val Ser Asp Ala Glu Glu Glu Pro Val Glu Leu Glu Pro Gly
            20                  25                  30

Ala Phe Val Pro Val Asp Leu Arg Arg Pro Asn Pro Asn Gly Leu Glu
        35                  40                  45

Phe Asp Asn Leu Tyr Leu Asp Met Asn Gly Ile Ile His Pro Cys Phe
    50                  55                  60

His Pro Glu Gly Arg Pro Ala Pro Thr Thr Tyr Asp Glu Val Phe Lys
65                  70                  75                  80

Ser Ile Phe Asp Tyr Ile Asp His Leu Phe Gly Leu Ile Arg Pro Arg
                85                  90                  95

Lys Leu Leu Tyr Met Ala Ile Asp Gly Val Ala Pro Arg Ala Lys Met
            100                 105                 110

Asn Gln Gln Arg Ser Arg Arg Phe Arg Ala Ala Lys Asp Ala Ala Asp
        115                 120                 125
```

-continued

```
Ala Ala Ala Glu Glu Glu Arg Leu Arg Lys Glu Phe Glu Ala Glu Gly
        130                 135                 140

Arg Thr Leu Ala Gln Lys Glu Lys Ser Glu Ala Ile Asp Ser Asn Val
145                 150                 155                 160

Ile Thr Pro Gly Thr Glu Phe Met Phe Val Leu Ser Thr Ala Leu Gln
                165                 170                 175

Tyr Tyr Ile Gln Leu Arg Leu Asn His Thr Leu Gly Trp Gln Ser Val
            180                 185                 190

Lys Ile Ile Leu Ser Asp Ser Asn Val Pro Gly Glu Gly Glu His Lys
        195                 200                 205

Ile Met Ser Tyr Ile Arg Leu Gln Arg Asn Leu Pro Gly Phe Asp Pro
210                 215                 220

Asn Thr Arg His Cys Leu Tyr Gly Leu Asp Ala Asp Leu Ile Met Leu
225                 230                 235                 240

Ala Leu Ala Thr His Glu Val His Phe Ser Ile Leu Arg Glu Val Ile
                245                 250                 255

Ser Met Pro Gly Gln His Glu Lys Cys Phe Leu Cys Gly Gln Val Gly
                260                 265                 270

His Leu Ala Ala Glu Cys Arg Gly Pro Ser Gln Pro Asp Asn Ser Val
            275                 280                 285

Glu Leu Pro Pro Ile His Lys Lys Lys Tyr Gln Phe Leu Asn Ile Trp
290                 295                 300

Val Leu Arg Glu Tyr Leu Ala Lys Asp Leu Glu Ile Ile Asp Ala Pro
305                 310                 315                 320

Phe Lys Ile Asn Phe Glu Arg Leu Ile Asp Asp Phe Val Phe Met Cys
                325                 330                 335

Phe Phe Val Gly Asn Asp Phe Leu Pro His Met Pro Thr Leu Glu Ile
                340                 345                 350

Arg Glu Gly Ala Ile Asn Leu Leu Met Ser Ile Tyr Arg Ser Glu Phe
            355                 360                 365

Thr Ser Met Gly Gly Tyr Leu Thr Asp Val Gly Glu Val Ile Leu Asp
370                 375                 380

Arg Val Glu His Phe Ile Gln Ser Val Ala Val Asn Glu Gly Gln Ile
385                 390                 395                 400

Phe Gln Lys Arg Ala Arg Ile Gln Gln Ala Arg Glu Asn Asn Glu Glu
                405                 410                 415

Lys His Lys Met Gln Arg Glu Asn Ser Glu Glu Asp Gln Tyr Val Asp
            420                 425                 430

Lys Val Lys Leu Gly Glu Pro Gly Tyr Arg Glu Arg Tyr Tyr Ala Asp
        435                 440                 445

Lys Phe Lys Glu Glu Ala Glu Ser Lys Pro Ile Val Gln Val Arg Arg
450                 455                 460

Asp Val Val Gln Lys Tyr Val Glu Gly Leu Cys Trp Val Met Arg Tyr
465                 470                 475                 480

Tyr Tyr Gln Gly Val Cys Ser Trp Gln Trp Phe Tyr Pro Tyr His Tyr
                485                 490                 495

Ala Pro Phe Ala Ser Asp Leu Lys Gly Leu Ala Glu Leu Glu Ile Thr
                500                 505                 510

Phe Phe Leu Gly Gln Pro Phe Lys Pro Phe Asp Gln Leu Met Gly Thr
            515                 520                 525

Leu Pro Ala Ala Ser Ser Asn Ala Leu Pro Lys Tyr Tyr Gly Asp Leu
530                 535                 540

Met Ser Asp Pro Asp Ser Pro Leu Lys Ser Phe Tyr Pro Lys Asp Phe
```

```
545                 550                 555                 560
Glu Ile Asp Met Asn Gly Lys Arg Phe Ala Trp Gln Gly Val Ala Lys
                565                 570                 575
Leu Pro Phe Ile Asp Glu Arg Arg Leu Leu Ala Glu Thr Arg Lys Leu
                580                 585                 590
Glu Asp Thr Leu Thr Glu Glu Lys Phe Arg Asn Arg Thr Met Leu
                595                 600                 605
Asp Ile Ile Tyr Val Arg Asp Thr His Pro Leu Ile Thr Gln Ile Ile
        610                 615                 620
Phe Leu Tyr Gln Asn Tyr Tyr His Leu Ser Arg Thr Asp Pro Tyr Val
625                 630                 635                 640
Ile Pro Ile Glu Pro Ala Ala Ser Gly Gly Met Asn Gly Phe Leu Cys
                645                 650                 655
Leu Ser Glu Arg Asn Trp Tyr Ser Val Thr Val Thr Ser Pro Val Lys
                660                 665                 670
Gly Phe Asn Gly Ile Ala Gln Asn Arg Val Leu Asn Ala Ala Tyr Leu
                675                 680                 685
Asn Pro Gln Tyr His Lys His Ile Pro Glu Pro Pro Ala Gly Val Ile
        690                 695                 700
Ile Pro Ala Lys Ile Leu Lys Pro Ser Asp Phe Lys Pro Phe Pro Val
705                 710                 715                 720
Leu Trp His Gln Asp Asn Ser Arg Arg Gln Val Arg Glu Arg Pro Gln
                725                 730                 735
Val Ser Gly Ala Leu Ser Gly Ser Leu Leu Gly Glu Ala Ala His Arg
                740                 745                 750
Leu Val Lys Asn Ser Leu Gln Ile Arg Ser Gly Asn Ala Ala Gly Leu
                755                 760                 765
Leu Tyr Met Pro Tyr Arg Gly Ala Pro Tyr Gly Pro Gly Asn Arg Pro
                770                 775                 780
Arg Pro Ala Gly Pro Leu Gly Tyr Glu Arg Gly Phe Val Asp Asn Pro
785                 790                 795                 800
Tyr His Ala His Met Ser Arg Ser Val Pro Asn Pro His Ala Gln Phe
                805                 810                 815
Phe Gly Asp Ser Gln Ala Asn Arg Gln Pro Met Arg Ile Leu Glu Arg
                820                 825                 830
Pro Asp Ser Arg Ser His Asp Ala Gly Ile Arg Ala Ser Met Ser Lys
                835                 840                 845
Leu Thr Ile Gln Glu Gly Pro Arg Pro His Gln Asn Asn Arg Met Gln
        850                 855                 860
Asn Ser Gly Tyr Trp Pro Asn Gln Pro His Pro Thr His Phe Thr Gly
865                 870                 875                 880
Pro Pro Ala Gln Arg Pro Met Gln Asn Ile Ser Phe Thr Pro Gln Arg
                885                 890                 895
Pro Phe Gln Thr Gly Gly Phe Pro Gln Gln Arg Pro Val Asn Gly Ala
                900                 905                 910
Pro Pro Pro Leu Pro Pro Ser Asn Trp Ile Gly Lys Gln Pro Ser Gly
                915                 920                 925
Cys His Met Ser Val Ser Pro Ala Lys Leu Asp Pro Arg Thr Ala Pro
                930                 935                 940
Asp Arg Gln Pro Lys Gln Asp Asn Pro Arg Ser Gln Gln Asp Lys Arg
945                 950                 955                 960
Gln Gln Ala Thr Lys Val Tyr Arg Val Lys Thr Gln Ala Thr Asn Val
                965                 970                 975
```

```
Asn Gly Leu Ser Glu Pro Gly Lys Gln Glu Glu Pro Glu Gly
            980                 985                 990

<210> SEQ ID NO 9
<211> LENGTH: 991
<212> TYPE: DNA
<213> ORGANISM: Zea mays
<220> FEATURE:
<221> NAME/KEY: CDS
<222> LOCATION: (253)..(783)

<400> SEQUENCE: 9
ccaccaccag gccttcttct accccatcc caacgcccag gccacaccag cgcagcgagc      60
tctctcctcg tagcggagtc ccagcccctc acgccctccc gatcgcgctc gtcggcgccc    120
ttgtcgactc gagcccgctt ctgggccgat cgacagcgag agcgagagca gcggcgcgcc    180
gaggagagct ctttcggtgc tgctgtataa cgacgacgac agcaggcggc agataacaca    240
taaaggcgcg cg atg tgc gac gcg gcg gcc gtg gcg gct ccg cgg tac agg   291
             Met Cys Asp Ala Ala Ala Val Ala Ala Pro Arg Tyr Arg
               1               5                  10 ggc gtg cgg aag cgg ccg tgg ggc cgg ttc gcg gcg gag atc cgg gac    339
Gly Val Arg Lys Arg Pro Trp Gly Arg Phe Ala Ala Glu Ile Arg Asp
         15                  20                  25 ccg gcg aag cgc gcg cgc gtc tgg ctc ggc acc ttc gac tcc gcc gag    387
Pro Ala Lys Arg Ala Arg Val Trp Leu Gly Thr Phe Asp Ser Ala Glu
 30                  35                  40                  45 gcc gcg gcg cgc gcc tac gac gtg gcc gcg cgg gcc ctg cgc ggc ccg    435
Ala Ala Ala Arg Ala Tyr Asp Val Ala Ala Arg Ala Leu Arg Gly Pro
                 50                  55                  60 ctc gcc agg acc aac ttc ccc gcg ctc acc tcc cgc cct cct gcc aac    483
Leu Ala Arg Thr Asn Phe Pro Ala Leu Thr Ser Arg Pro Pro Ala Asn
             65                  70                  75 ctg ccc gcg ccc acg ccc acg tgc agc tca agc tcc acc gtc gag tcc    531
Leu Pro Ala Pro Thr Pro Thr Cys Ser Ser Ser Ser Thr Val Glu Ser
         80                  85                  90 tcc agc ggg ccc cgg gcc ggg gtg ccc agg gcg ggc agg cgc gct gct    579
Ser Ser Gly Pro Arg Ala Gly Val Pro Arg Ala Gly Arg Arg Ala Ala
     95                 100                 105 ggg aag ccg cgt gcc ccg cgg cag gcg gcc gcg ccc gcc gac gcc gac    627
Gly Lys Pro Arg Ala Pro Arg Gln Ala Ala Ala Pro Ala Asp Ala Asp
110                 115                 120                 125 tgc cgt agc gac tgc gcc tcg tcg gcc tcc gtc gtg gac gac ggc gac    675
Cys Arg Ser Asp Cys Ala Ser Ser Ala Ser Val Val Asp Asp Gly Asp
                130                 135                 140 gac gcc tcc acg gtc cgg tcg cgc ccg gcg ctc gac ctc aat ctc ccc    723
Asp Ala Ser Thr Val Arg Ser Arg Pro Ala Leu Asp Leu Asn Leu Pro
            145                 150                 155 gcg ccg ctc gac gtc gac gat ggt cat gac ctc gag ctt tgc acg gac    771
Ala Pro Leu Asp Val Asp Asp Gly His Asp Leu Glu Leu Cys Thr Asp
        160                 165                 170 ctg cgg ctc tga ataggcgacc ggatccacgg acggatcggg acgaagggag       823
Leu Arg Leu
    175 agaaggcggt ttttgctttg gtcttctttt cttgatcaga ttctgccttg ctttgacttg    883 tcgtgctcga gggagcttgt accagtgctg cactgtacta ctcgatacga atggcaatag    943 aattggatga cgattcctgc aaaaaaaaaa aaaaaaaaa aaaaaaaa                991

<210> SEQ ID NO 10
```

```
<211> LENGTH: 176
<212> TYPE: PRT
<213> ORGANISM: Zea mays

<400> SEQUENCE: 10

Met Cys Asp Ala Ala Ala Val Ala Ala Pro Arg Tyr Arg Gly Val Arg
1               5                   10                  15

Lys Arg Pro Trp Gly Arg Phe Ala Ala Glu Ile Arg Asp Pro Ala Lys
            20                  25                  30

Arg Ala Arg Val Trp Leu Gly Thr Phe Asp Ser Ala Glu Ala Ala Ala
        35                  40                  45

Arg Ala Tyr Asp Val Ala Ala Arg Ala Leu Arg Gly Pro Leu Ala Arg
    50                  55                  60

Thr Asn Phe Pro Ala Leu Thr Ser Arg Pro Pro Ala Asn Leu Pro Ala
65                  70                  75                  80

Pro Thr Pro Thr Cys Ser Ser Ser Ser Thr Val Glu Ser Ser Ser Gly
                85                  90                  95

Pro Arg Ala Gly Val Pro Arg Ala Gly Arg Arg Ala Ala Gly Lys Pro
            100                 105                 110

Arg Ala Pro Arg Gln Ala Ala Ala Pro Ala Asp Ala Asp Cys Arg Ser
        115                 120                 125

Asp Cys Ala Ser Ser Ala Ser Val Val Asp Asp Gly Asp Asp Ala Ser
    130                 135                 140

Thr Val Arg Ser Arg Pro Ala Leu Asp Leu Asn Leu Pro Ala Pro Leu
145                 150                 155                 160

Asp Val Asp Asp Gly His Asp Leu Glu Leu Cys Thr Asp Leu Arg Leu
                165                 170                 175

<210> SEQ ID NO 11
<211> LENGTH: 36
<212> TYPE: DNA
<213> ORGANISM: Zea mays

<400> SEQUENCE: 11
tcgacccacg cgtccgaaaa aaaaaaaaaa aaaaaa                         36
```